United States Patent
Siegel et al.

(10) Patent No.: US 8,436,003 B2
(45) Date of Patent: May 7, 2013

(54) SUBSTITUTED IMIDAZO- AND TRIAZOLOPYRIMIDINES, IMIDAZO- AND PYRAZOLOPYRAZINES AND IMIDAZOTRIAZINES

(75) Inventors: Stephan Siegel, Berlin (DE); Andreas Wilmen, Köln (DE); Niels Svenstrup, Velbert (DE); Mark Jean Gnoth, Mettmann (DE); Adrian Tersteegen, Wuppertal (DE); Ulrich Rester, Wuppertal (DE)

(73) Assignee: Bayer Intellectual Property GmbH, Monehim (DE)

( * ) Notice: Subject to any disclaimer, the term of this patent is extended or adjusted under 35 U.S.C. 154(b) by 22 days.

(21) Appl. No.: 12/992,715

(22) PCT Filed: May 2, 2009

(86) PCT No.: PCT/EP2009/003167
§ 371 (c)(1),
(2), (4) Date: Feb. 10, 2011

(87) PCT Pub. No.: WO2009/138176
PCT Pub. Date: Nov. 19, 2009

(65) Prior Publication Data
US 2011/0144131 A1 Jun. 16, 2011

(30) Foreign Application Priority Data
May 15, 2008 (DE) .......................... 10 2008 023 801

(51) Int. Cl.
*A01N 43/90* (2006.01)
*A61K 31/519* (2006.01)
*C07D 487/00* (2006.01)

(52) U.S. Cl.
USPC ...................................... 514/259.31; 544/263

(58) Field of Classification Search ........................ None
See application file for complete search history.

(56) References Cited

U.S. PATENT DOCUMENTS

| | | | |
|---|---|---|---|
| 2002/0115635 A1 | 8/2002 | Fishman et al. | |
| 2004/0249148 A1 | 12/2004 | Erguden | |
| 2006/0106023 A1 | 5/2006 | Guzi | |
| 2006/0183746 A1 | 8/2006 | Currie | |
| 2010/0113441 A1 | 5/2010 | Siegel | |

FOREIGN PATENT DOCUMENTS

| | | | |
|---|---|---|---|
| WO | 9964401 A1 | 12/1999 | |
| WO | 0183485 A1 | 11/2001 | |
| WO | 2004026877 A1 | 4/2004 | |
| WO | 2005035532 A1 | 4/2005 | |
| WO | 2005044793 A1 | 5/2005 | |
| WO | 2006044687 A1 | 4/2006 | |
| WO | 2007058873 A2 | 5/2007 | |
| WO | 2007138072 A1 | 12/2007 | |
| WO | 2007145921 A1 | 12/2007 | |

OTHER PUBLICATIONS

Vippagunta et. al. Advanced Drug Delivery Reviews 48 (2001) 3-26.*
Woodgett JR., Trends Biochem. Sci. (1991), 16(5), 177-81.
Woodarz A., Nusse R., Annu. Rev. Cell Dev. Biol. (1998), 14, 59-88.
Kirsetter et al., Nat Immunol. (2006), 7(10), 1048-56.
O'Brien et al., British Journal of Cancer (2006), 95, 1632-1636.
Chemical Abstracts Service, Fishman, et al. Adenosine receptor ligands for the modulation of glycogen activity, and therapeutic uses, XP002536566, STN Database accession No. 2002:638281 (abstract), (accessed in 2002).

* cited by examiner

*Primary Examiner* — Jeffrey Murray

(57) ABSTRACT

The invention relates to substituted triazolopyrimidines of the formula

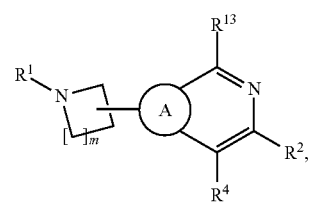

processes for their preparation, and their use for the treatment of hematological disorders.

7 Claims, No Drawings

SUBSTITUTED IMIDAZO- AND TRIAZOLOPYRIMIDINES, IMIDAZO- AND PYRAZOLOPYRAZINES AND IMIDAZOTRIAZINES

The invention relates to substituted imidazo- and triazolopyrimidines, imidazo- and pyrazolopyrazines and imidazotriazines and processes for their preparation, and their use for the manufacture of medicaments for the treatment and/or prophylaxis of diseases, in particular of hematological disorders, preferably of leukopenias and neutropenias.

Glycogen synthase kinase 3 (GSK3) belongs to the families of serine/threonin kinases. Specific substrates are inter alia cytoskeletal proteins and transcription factors. Two isoforms, GSK3α and GSK3β, have been identified to date (Woodgett J R., Trends Biochem. Sci. (1991), 16(5), 177-81). Both isoforms are constitutively active in chiefly resting, non-proliferating cells.

GSK3β is of central importance within the Wnt/Wingless signal transduction pathway. The latter is one of the most important, evolutionarily conserved signalling systems. Wnt signals control very early patterning processes during embryogenesis, they induce mesoderm formation and many organs, and they control the proliferation and differentiation of stem cells (Wodarz A., Nusse R., Annu. Rev. Cell Dev. Biol. (1998), 14, 59-88; Kirstetter et al., Nat Immunol. (2006), 7(10), 1048-56). There is intracellular compartmentalization of the Wnt signalling pathway, thus making it possible to control a wide variety of processes. Within the Wnt cascade, glycogen synthase kinase 3 forms part of a multi-protein complex to which belong inter alia the structural molecules axin, the tumor suppressor protein APC and the transcription cofactor β-catenin. In this connection, β-catenin is the principal substrate of GSK3β. The consequence of this GSK3β-mediated phosphorylation is the proteasomal degradation of β-catenin Inhibition of GSK3 activity leads to an accumulation of β-catenin in the cell with subsequent translocation into the cell nucleus. There, β-catenin acts as a cofactor in transcription complexes and thus is partly responsible for the expression of defined target genes.

Radiotherapies or chemotherapies are among the standard approaches to controlling cancer. Both types of therapy are nonspecific in relation to their target cells, i.e. not only tumor cells but also untransformed, proliferating cells are affected. These untransformed, proliferating cells also include hematopoietic progenitor cells which develop inter alia into neutrophilic granulocytes. A significant reduction in the number of neutrophiles is referred to as neutropenia. A neutropenia induced by chemotherapy or radiotherapy results clinically in an increased susceptibility to infection. If the neutropenia is substantial there is an increase in the morbidity and, in some circumstances, also the mortality of a therapy (O'Brien et al., British Journal of Cancer (2006), 95, 1632-1636).

Inhibition of GSK3 activity leads to an increased rate of proliferation and differentiation of hematopoietic stem cells and can accordingly be utilized for therapeutic intervention in relation to a therapy-induced neutropenia.

WO2006/044687 describes the use of imidazopyrimidinylamines, pyrazolo- and imidazopyrazines as kinase inhibitors for the treatment of cancer and WO01/083485 discloses imidazo- and triazolopyrimidines inter alia for the treatment of asthma and cancer. WO2005/044793 discloses inter alia the use of imidazopyrimidinylamines as CRF (corticotropin releasing factor) receptor antagonists for treating depressions. WO2007/138072 describes the use of 6-alkyl-substituted triazolopyrazines for the treatment of degenerative and inflammatory disorders. WO99/064401 describes inter alia imidazopyrazines as somatostatin receptor ligands for the treatment of diabetes. WO2004/026877, US2006/0183746, US2006/0106023 and WO2007/058873 describe the use of imidazopyrazinylamines for the treatment of cancer. WO 2007/145921 describes imidazopyrazines as protein kinase inhibitors for the treatment of cancer. WO03/000693 claims imidazotriazines as PDE10 inhibitors for treating neurodegenerative diseases.

One object of the present invention is therefore to provide novel compounds as GSK3β inhibitors for the treatment of hematological disorders, preferably of neutropenia in humans and animals.

The invention provides compounds of the formula

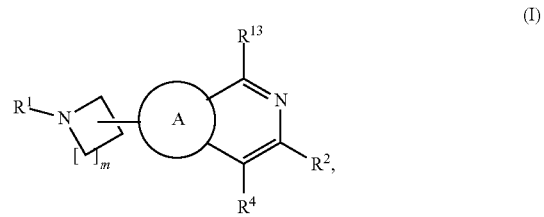

(I)

in which
A represents a group of the formula

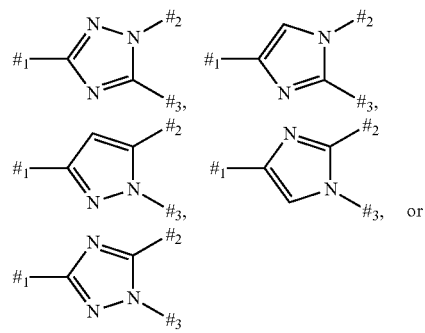

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached,
m represents the number 1, 2, 3 or 4,
$R^1$ represents hydrogen, $C_1$-$C_6$-alkyl, $C_3$-$C_6$-cycloalkyl, $C_3$-$C_6$-cycloalkylmethyl or hydroxycarbonylmethyl,
$R^2$ represents phenyl,
where phenyl may be substituted by 1 to 3 substituents, where the substituents are independently of one another selected from the group consisting of hydroxyl, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonyl, $C_1$-$C_4$-alkylsulfonylamino, $C_1$-$C_4$-alkylaminosulfonyl, phenyl, pyrrolidinyl, piperidinyl, morpholinyl, piperazinyl, pyrrolidinylmethyl, piperidinylmethyl, morpholinylmethyl and piperazinylmethyl, where phenyl, pyrrolidinyl, piperidinyl, morpholinyl, piperazinyl, pyrrolidinylmethyl, piperidinylmethyl, morpholinylmethyl and piperazinylmethyl may be substituted by 1 to 3 substituents, where the substituents are independently of one another selected from the group consisting of halogen, cyano, trifluoromethyl, trifluoromethoxy and $C_1$-$C_4$-alkyl, $R^4$ represents hydrogen, chlorine or fluorine,
$R^{13}$ represents a group of the formula

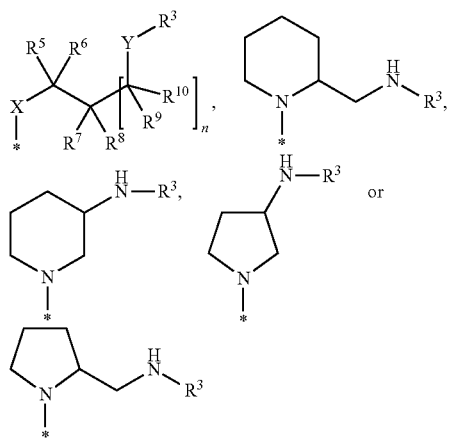

where
* represents the point of attachment to the heterocycle,
n represents the number 0 or 1,
X represents $NR^{11}$, S or O,
where
$R^{11}$ represents hydrogen, $C_1$-$C_3$-alkyl or cyclopropyl,
Y represents $NR^{12}$, S or O,
where
$R^{12}$ represents hydrogen, $C_1$-$C_3$-alkyl or cyclopropyl,
$R^3$ represents 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl,
where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are independently of one another selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl
where alkyl, alkoxy, alkylamino, alkylcarbonyl, alkoxycarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl,
$R^5$ represents hydrogen, $C_1$-$C_3$-alkyl or cyclopropyl,
$R^6$ represents hydrogen or $C_1$-$C_3$-alkyl,
$R^7$ represents hydrogen, $C_1$-$C_3$-alkyl or cyclopropyl,
$R^8$ represents hydrogen or $C_1$-$C_3$-alkyl,
$R^9$ represents hydrogen, $C_1$-$C_3$-alkyl or cyclopropyl,
$R^{10}$ represents hydrogen or $C_1$-$C_3$-alkyl,
and their salts, their solvates and the solvates of their salts.

Compounds according to the invention are the compounds of the formula (I) and the salts, solvates and solvates of the salts thereof, as well as the compounds encompassed by the formula (I) and mentioned below as exemplary embodiment(s), and the salts, solvates and solvates of the salts thereof, insofar as the compounds encompassed by formula (I) and mentioned below are not already salts, solvates and solvates of the salts.

The compounds of the invention may, depending on their structure, exist in stereoisomeric forms (enantiomers, diastereomers). The invention therefore encompasses the enantiomers or diastereomers and respective mixtures thereof. The stereoisomerically pure constituents can be isolated in a known manner from such mixtures of enantiomers and/or diastereomers.

Where the compounds of the invention can occur in tautomeric forms, the present invention encompasses all tautomeric forms.

Salts preferred for the purposes of the present invention are physiologically acceptable salts of the compounds of the invention. However, salts which are themselves unsuitable for pharmaceutical applications but can be used for example for isolating or purifying the compounds of the invention are also encompassed.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates refer for the purposes of the invention to those forms of the compounds of the invention which form a complex in the solid or liquid state through coordination with solvent molecules. Hydrates are a specific form of solvates in which the coordination takes place with water.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

For the purposes of the present invention, the substituents have, unless specified otherwise, the following meaning.

Alkyl per se and "alk" and "alkyl" in alkoxy, alkylamino, alkylcarbonyl, alkoxycarbonyl, alkylaminocarbonyl, alkylcarbonylamino, alkylsulfonyl, alkylsulfonylamino and alkylaminosulfonyl stand for a linear or branched alkyl radical having 1 to 6, preferably 1 to 4, carbon atoms, by way of example and preferably for methyl, ethyl, n-propyl, isopropyl, n-butyl, tert-butyl, n-pentyl and n-hexyl.

Alkoxy stands by way of example and preferably for methoxy, ethoxy, n-propoxy, isopropoxy, n-butoxy and tert-butoxy.

Alkylamino stands for an alkylamino radical having one or two alkyl substituents (chosen independently of one another), by way of example and preferably for methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-alkylamino stands for example for a monoalkylamino radical having 1 to 4 carbon atoms or for a dialkylamino radical having 1 to 4 carbon atoms in each alkyl substituent in each case.

Alkylcarbonyl stands by way of example and preferably for methylcarbonyl, ethylcarbonyl, n-propyl-carbonyl, isopropylcarbonyl, n-butylcarbonyl and tert-butylcarbonyl.

Alkoxycarbonyl stands by way of example and preferably for methoxycarbonyl, ethoxycarbonyl, n-propoxycarbonyl, isopropoxycarbonyl, n-butoxycarbonyl and tert-butoxycarbonyl.

Alkylaminocarbonyl stands for an alkylaminocarbonyl radical having one or two alkyl substituents (chosen independently of one another), by way of example and preferably for methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl stands for example for a monoalkylaminocarbonyl radical having 1 to 4 carbon atoms or for a dialkylaminocarbonyl radical having 1 to 4 carbon atoms in each alkyl substituent in each case.

Alkylcarbonylamino stands by way of example and preferably for methylcarbonylamino, ethyl-carbonylamino, n-propylcarbonylamino, isopropylcarbonylamino, n-butylcarbonylamino and tert-butylcarbonylamino.

Alkylsulfonyl stands by way of example and preferably for methylsulfonyl, ethylsulfonyl, n-propylsulfonyl, isopropylsulfonyl, n-butylsulfonyl and tert-butylsulfonyl.

Alkylaminosulfonyl stands for an alkylaminosulfonyl radical having one or two alkyl substituents (chosen independently of one another), by way of example and preferably for methylaminosulfonyl, ethylaminosulfonyl, n-propylaminosulfonyl, isopropylaminosulfonyl, tert-butylaminosulfonyl, N,N-dimethylaminosulfonyl, N,N-diethylaminosulfonyl, N-ethyl-N-methylaminosulfonyl, N-methyl-N-n-propylaminosulfonyl, N-isopropyl-N-n-propylaminosulfonyl and N-tert-butyl-N-methylaminosulfonyl. $C_1$-$C_4$-Alkylaminosulfonyl stands for example for a monoalkylaminosulfonyl radical having 1 to 4 carbon atoms or for a dialkylaminosulfonyl radical having 1 to 4 carbon atoms in each alkyl substituent in each case.

Alkylsulfonylamino stands by way of example and preferably for methylsulfonylamino, ethyl-sulfonylamino, n-propylsulfonylamino, isopropylsulfonylamino, n-butylsulfonylamino and tert-butylsulfonylamino.

Cycloalkyl stands for a monocyclic cycloalkyl group usually having 3 to 6 carbon atoms, and mention may be made by way of example and preferably of cyclopropyl, cyclobutyl, cyclopentyl and cyclohexyl for cycloalkyl.

Halogen stands for fluorine, chlorine, bromine and iodine, preferably for fluorine and chlorine.

In the formulae of the group which can stand for A, the end point of the line, besides which a $\#_1$, $\#_2$ or $\#_3$ stands in each case, does not stand for a carbon atom or a $CH_2$ group but forms part of the bond to the atom to which A is bonded.

In the formulae of the group which can stand for $R^{13}$, the end point of the line, besides which a * stands in each case, does not stand for a carbon atom or a $CH_2$ group but forms part of the bond to the atom to which $R^{13}$ is bonded.

The heterocycle of the formula

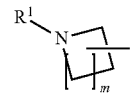

may be attached via any position of the heterocycle to A, the position of attachment not being limited to the two positions which are located immediately adjacent to the bond drawn.

Preference is given to compounds of the formula (I) in which

A represents a group of the formula

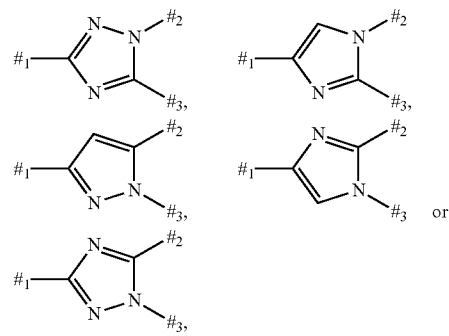

where $\#_1$ represents the point of attachment to the heterocycle substituted by $R^1$, $\#_2$ represents the point of attachment to the carbon atom to which $R^{13}$ is attached, $\#_3$ represents the point of attachment to the carbon atom to which $R^4$ is attached, m represents the number 1, 2, 3 or 4, $R^1$ represents hydrogen, $C_1$-$C_6$-alkyl, $C_3$-$C_6$-cycloalkyl, $C_3$-$C_6$-cycloalkylmethyl or hydroxycarbonylmethyl, $R^2$ represents phenyl, where phenyl may be substituted by 1 to 3 substituents, where the substituents are independently of one another selected from the group consisting of hydroxyl, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonyl, $C_1$-$C_4$-alkylsulfonylamino, $C_1$-$C_4$-alkylaminosulfonyl, phenyl, pyrrolidinyl, piperidinyl, morpholinyl, piperazinyl, pyrrolidinylmethyl, piperidinylmethyl, morpholinylmethyl and piperazinylmethyl, where phenyl, pyrrolidinyl, piperidinyl, morpholinyl, piperazinyl, pyrrolidinylmethyl, piperidinylmethyl, porpholinylmethyl and piperazinylmethyl may be substituted by 1 to 3 substituents, where the substituents are independently of one another selected from the group consisting of halogen, cyano, trifluoromethyl, trifluoromethoxy and $C_1$-$C_4$-alkyl, $R^4$ represents hydrogen, chlorine or fluorine, $R^{13}$ represents a group of the formula

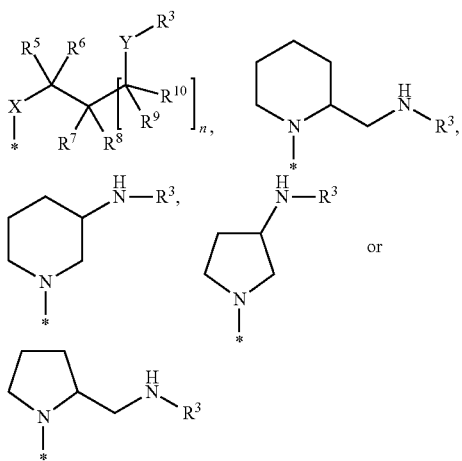

where

* represents the point of attachment to the heterocycle, n represents the number 0 or 1, X represents $NR^{11}$ or O, where $R^{11}$ represents hydrogen or methyl, Y represents $NR^{12}$, where $R^{12}$ represents hydrogen or methyl, $R^3$ represents 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl, where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are independently of one another selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, where alkyl, alkoxy, alkylamino, alkylcarbonyl, alkoxycarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl, $R^5$ represents hydrogen or methyl, $R^6$ represents hydrogen or methyl, $R^7$ represents hydrogen or methyl, $R^8$ represents hydrogen or methyl, $R^9$ represents hydrogen or methyl, $R^{10}$ represents hydrogen or methyl, and their salts, their solvates and the solvates of their salts.

Preference is also given to compounds of the formula (I), in which

A represents a group of the formula

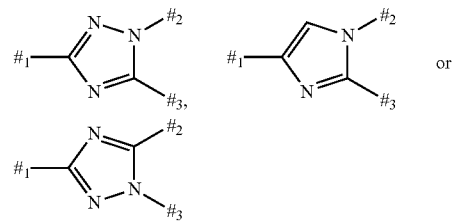

where $\#_1$ represents the point of attachment to the heterocycle substituted by $R^1$, $\#_2$ represents the point of attachment to the carbon atom to which $R^{13}$ is attached, $\#_3$ represents the point of attachment to the carbon atom to which $R^4$ is attached, m represents the number 1, 2, 3 or 4, $R^1$ represents hydrogen, $C_1$-$C_6$-alkyl, $C_3$-$C_6$-cycloalkyl, $C_3$-$C_6$-cycloalkylmethyl or hydroxycarbonylmethyl, $R^2$ represents phenyl, where phenyl may be substituted by 1 to 3 substituents, where the substituents are independently of one another selected from the group consisting of hydroxyl, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonyl, $C_1$-$C_4$-alkylsulfonylamino, $C_1$-$C_4$-alkylaminosulfonyl, phenyl, pyrrolidinyl, piperidinyl, morpholinyl, piperazinyl, pyrrolidinylmethyl, piperidinylmethyl, morpholinylmethyl and piperazinylmethyl, where phenyl, pyrrolidinyl, piperidinyl, morpholinyl, piperazinyl, pyrrolidinylmethyl, piperidinylmethyl, morpholinylmethyl and piperazinylmethyl may be substituted by 1 to 3 substituents, where the substituents are independently of one another selected from the group consisting of halogen, cyano, trifluoromethyl, trifluoromethoxy and $C_1$-$C_4$-alkyl, $R^4$ represents hydrogen or chlorine, $R^{13}$ represents a group of the formula

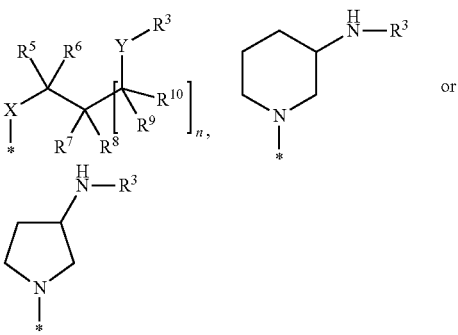

where
* represents the point of attachment to the heterocycle,
n represents the number 0,
X represents $NR^{11}$,
  where
  $R^{11}$ represents hydrogen or methyl,
Y represents $NR^{12}$,
  where
  $R^{12}$ represents hydrogen or methyl,
$R^3$ represents 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl,
  where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are independently of one another selected from the group consisting of halogen, cyano, nitro, amino, trifluoromethyl, trifluoromethoxy, aminocarbonyl, trifluoromethylcarbonyl, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
    where alkylamino, alkylcarbonyl, alkoxycarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl,
$R^5$ represents hydrogen or methyl,
$R^6$ represents hydrogen,
$R^7$ represents hydrogen or methyl,
$R^8$ represents hydrogen,
$R^9$ represents hydrogen,
$R^{10}$ represents hydrogen,
and their salts, their solvates and the solvates of their salts.

Preference is also given to compounds of the formula (I) in which
A represents a group of the formula

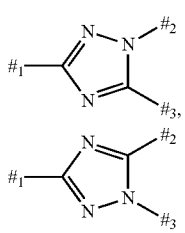  or  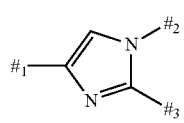

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached,
m represents the number 1, 2, 3 or 4,
$R^1$ represents hydrogen, $C_1$-$C_6$-alkyl, $C_3$-$C_6$-cycloalkyl, $C_3$-$C_6$-cycloalkylmethyl or hydroxycarbonylmethyl,
$R^2$ represents phenyl,
  where phenyl may be substituted by 1 to 3 substituents, where the substituents are independently of one another selected from the group consisting of chlorine, fluorine, trifluoromethyl, trifluoromethoxy and methyl,
$R^4$ represents hydrogen,
$R^{13}$ represents a group of the formula

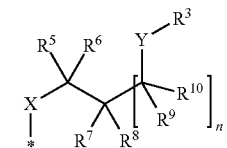  or  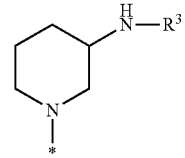

where
* represents the point of attachment to the heterocycle,
n represents the number 0,
X represents $NR^{11}$,
  where
  $R^{11}$ represents hydrogen,
Y represents $NR^{12}$,
  where
  $R^{12}$ represents hydrogen,
$R^3$ represents 2-pyridyl or 1,3-thiazol-2-yl,
  where 2-pyridyl and 1,3-thiazol-2-yl are substituted by 1 or 2 substituents, where the substituents are independently of one another selected from the group consisting of cyano, nitro, amino, trifluoromethylcarbonyl, ethylcarbonyl and methylcarbonyl,
$R^5$ represents hydrogen or methyl,
$R^6$ represents hydrogen,
$R^7$ represents hydrogen or methyl,
$R^8$ represents hydrogen,
$R^9$ represents hydrogen,
$R^{10}$ represents hydrogen,
and their salts, their solvates and the solvates of their salts.

Preference is also given to compounds of the formula (I) in which
A represents a group of the formula

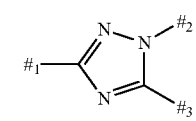

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached,
m represents the number 1, 2 or 3,
$R^1$ represents $C_1$-$C_4$-alkyl, cyclopropyl, cyclopropylmethyl or hydroxycarbonylmethyl,
$R^2$ represents phenyl,
  where phenyl may be substituted by 1 to 3 substituents, where the substituents are independently of one another selected from the group consisting of chlorine, fluorine, trifluoromethyl, trifluoromethoxy and methyl,
$R^4$ represents hydrogen, $R^{13}$ represents a group of the formula

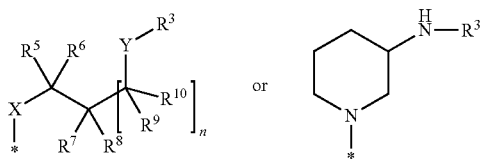

where
* represents the point of attachment to the heterocycle,
n represents the number 0,
X represents $NR^{11}$,
  where
  $R^{11}$ represents hydrogen,
Y represents $NR^{12}$,
  where
  $R^{12}$ represents hydrogen,
$R^3$ represents 2-pyridyl or 1,3-thiazol-2-yl,
  where 2-pyridyl and 1,3-thiazol-2-yl are substituted by 1 or 2 substituents, where the substituents are independently of one another selected from the group consisting of cyano, nitro, amino, trifluoromethylcarbonyl, ethylcarbonyl and methylcarbonyl,
$R^5$ represents hydrogen or methyl,
$R^6$ represents hydrogen,
$R^7$ represents hydrogen or methyl,
$R^8$ represents hydrogen,
$R^9$ represents hydrogen,
$R^{10}$ represents hydrogen,
and their salts, their solvates and the solvates of their salts.

Preference is also given to compounds of the formula (I) in which
A represents a group of the formula

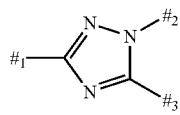

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached,
m represents the number 1, 2 or 3,
$R^1$ represents $C_1$-$C_4$-alkyl, cyclopropyl, cyclopropylmethyl or hydroxycarbonylmethyl,
$R^2$ represents phenyl,
  where phenyl may be substituted by 1 to 3 substituents, where the substituents are independently of one another selected from the group consisting of chlorine, fluorine, trifluoromethyl and methyl,
$R^4$ represents hydrogen, $R^{13}$ represents a group of the formula

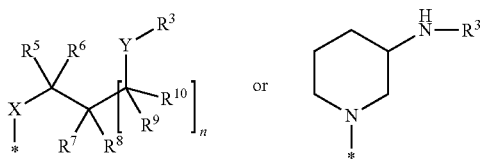

where
* represents the point of attachment to the heterocycle,
n represents the number 0,
X represents $NR^{11}$,
  where
  $R^{11}$ represents hydrogen,
Y represents $NR^{12}$,
  where
  $R^{12}$ represents hydrogen,
$R^3$ represents 2-pyridyl,
  where 2-pyridyl is substituted by 1 or 2 substituents, where the substituents are independently of one another selected from the group consisting of cyano, nitro, amino, trifluoromethylcarbonyl, ethylcarbonyl and methylcarbonyl,
$R^5$ represents hydrogen,
$R^6$ represents hydrogen,
$R^7$ represents hydrogen,
$R^8$ represents hydrogen,
$R^9$ represents hydrogen,
$R^{10}$ represents hydrogen,
and their salts, their solvates and the solvates of their salts.

Preference is also given to compounds of the formula (I) in which
A represents a group of the formula

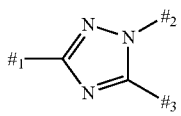

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached,
m represents the number 1, 2 or 3,
$R^1$ represents $C_1$-$C_4$-alkyl, cyclopropyl, cyclopropylmethyl or hydroxycarbonylmethyl,
$R^2$ represents phenyl,
  where phenyl may be substituted by 1 to 3 substituents, where the substituents are independently of one another selected from the group consisting of chlorine, fluorine, trifluoromethyl and methyl,
$R^4$ represents hydrogen, $R^{13}$ represents a group of the formula

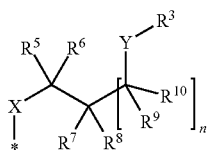

where
* represents the point of attachment to the heterocycle,
n represents the number 0,
X represents $NR^{11}$,
  where
  $R^{11}$ represents hydrogen,
Y represents $NR^{12}$,
  where
  $R^{12}$ represents hydrogen,
$R^3$ represents 2-pyridyl,
  where 2-pyridyl is substituted by 1 or 2 substituents, where the substituents are independently of one another selected from the group consisting of cyano, nitro, amino, trifluoromethylcarbonyl, ethylcarbonyl and methylcarbonyl,
$R^5$ represents hydrogen,
$R^6$ represents hydrogen,
$R^7$ represents hydrogen,
$R^8$ represents hydrogen,
$R^9$ represents hydrogen,
$R^{10}$ represents hydrogen,
and their salts, their solvates and the solvates of their salts.
Preference is also given to compounds of the formula (I) in which
A represents a group of the formula

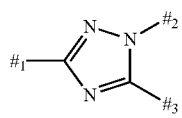

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached,
m represents the number 1, 2 or 3,
$R^1$ represents $C_1$-$C_4$-alkyl, cyclopropyl, cyclopropylmethyl or hydroxycarbonylmethyl,
$R^2$ represents phenyl,
  where phenyl may be substituted by 1 to 3 substituents, where the substituents are independently of one another selected from the group consisting of chlorine, fluorine, trifluoromethyl and methyl,
$R^4$ represents hydrogen, $R^{13}$ represents a group of the formula

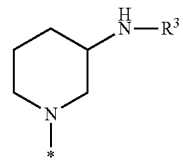

where
* represents the point of attachment to the heterocycle,
$R^3$ represents 2-pyridyl,
  where 2-pyridyl is substituted by 1 or 2 substituents, where the substituents are independently of one another selected from the group consisting of cyano, nitro, amino, trifluoromethylcarbonyl, ethylcarbonyl and methylcarbonyl,
and their salts, their solvates and the solvates of their salts.
Preference is also given to compounds of the formula (I) in which
A represents a group of the formula

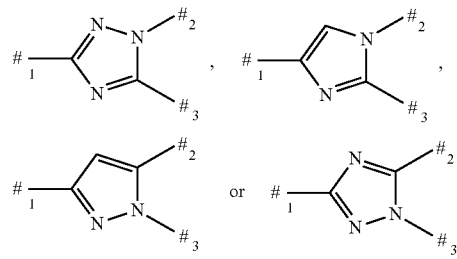

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached.
Preference is also given to compounds of the formula (I) in which
A represents a group of the formula

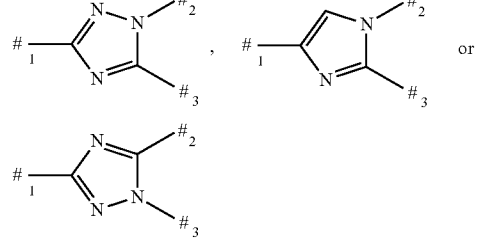

where
$\#_1$ represents the point of attachment to the heterocycle substituted by $R^1$,
$\#_2$ represents the point of attachment to the carbon atom to which $R^{13}$ is attached,
$\#_3$ represents the point of attachment to the carbon atom to which $R^4$ is attached.

Preference is also given to compounds of the formula (I) in which
A represents a group of the formula

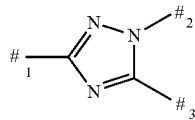

where
₁ represents the point of attachment to the heterocycle substituted by $R^1$,
₂ represents the point of attachment to the carbon atom to which $R^{13}$ is attached,
₃ represents the point of attachment to the carbon atom to which $R^4$ is attached.

Preference is also given to compounds of the formula (I) in which m represents the number 1, 2 or 3.

Preference is also given to compounds of the formula (I) in which $R^1$ represents $C_1$-$C_4$-alkyl, cyclopropyl, cyclopropylmethyl or hydroxycarbonylmethyl.

Preference is also given to compounds of the formula (I) in which $R^1$ represents $C_1$-$C_4$-alkyl, cyclopropyl or cyclopropylmethyl.

Preference is also given to compounds of the formula (I) in which
$R^2$ represents phenyl,
where phenyl may be substituted by 1 to 3 substituents, where the substituents are independently of one another selected from the group consisting of chlorine, fluorine, trifluoromethyl and methyl.

Preference is also given to compounds of the formula (I) in which $R^4$ represents hydrogen.

Preference is also given to compounds of the formula (I) in which n represents the number 0.

Preference is also given to compounds of the formula (I) in which X represents $NR^{11}$, where $R^{11}$ represents hydrogen.

Preference is also given to compounds of the formula (I) in which Y represents $NR^{12}$, where $R^{12}$ represents hydrogen.

Preference is also given to compounds of the formula (I) in which
$R^3$ represents 2-pyridyl,
where 2-pyridyl is substituted by 1 or 2 substituents, where the substituents are independently of one another selected from the group consisting of cyano, nitro, amino, trifluoromethylcarbonyl, ethylcarbonyl and methylcarbonyl.

Preference is also given to compounds of the formula (I) in which $R^5$, $R^6$, $R^7$, $R^8$, $R^9$ and $R^{10}$ represent hydrogen.

Preference is also given to compounds of the formula (I) in which
$R^{13}$ represents a group of the formula

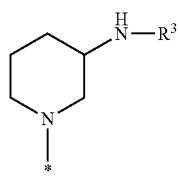

where
* represents the point of attachment to the heterocycle, $R^3$ represents 2-pyridyl,
where 2-pyridyl is substituted by 1 or 2 substituents, where the substituents are independently of one another selected from the group consisting of cyano, nitro, amino, trifluoromethylcarbonyl, ethylcarbonyl and methylcarbonyl.

Preference is also given to compounds of the formula (I) in which
$R^{13}$ represents a group of the formula

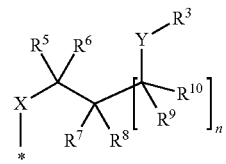

where
* represents the point of attachment to the heterocycle,
n represents the number 0,
X represents $NR^{11}$,
where
$R^{11}$ represents hydrogen,
Y represents $NR^{12}$,
where
$R^{12}$ represents hydrogen,
$R^3$ represents 2-pyridyl,
where 2-pyridyl is substituted by 1 or 2 substituents, where the substituents are independently of one another selected from the group consisting of cyano, nitro, amino, trifluoromethylcarbonyl, ethylcarbonyl and methylcarbonyl,
$R^5$ represents hydrogen,
$R^6$ represents hydrogen,
$R^7$ represents hydrogen,
$R^8$ represents hydrogen,
$R^9$ represents hydrogen,
$R^{10}$ represents hydrogen.

The invention furthermore provides a process for preparing the compounds of the formula (I), or their salts, their solvates or the solvates of their salts, where

[A] the compounds of the formula

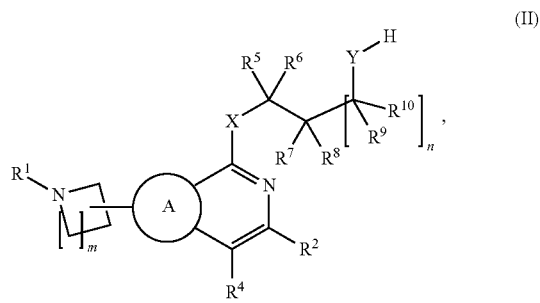

in which
A, m, X, Y, $R^1$, $R^2$, $R^4$, $R^5$, $R^6$, $R^7$, $R^8$, $R^9$ and $R^{10}$ have the meaning given above,
are reacted with compounds of the formula $$R^3-X^1 \qquad (III),$$

in which
$R^3$ has the meaning given above, and $X^1$ represents halogen, preferably chlorine or fluorine,
or
[B] the compounds of the formula

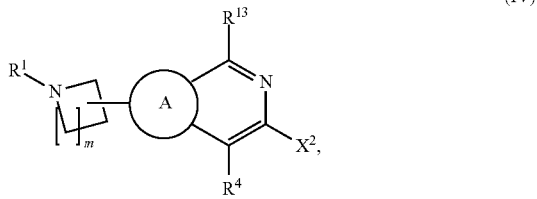

in which
A, m, $R^1$, $R^4$ and $R^{13}$ have the meaning given above, and
$X^2$ represents iodine, bromine, chlorine or trifluoromethanesulfonyl, preferably iodine or bromine,
are reacted with compounds of the formula

$$Q\text{-}R^2 \quad (V),$$

in which
$R^2$ has the meaning given above, and
Q represents —B(OH)$_2$, a boronic acid ester, preferably boronic acid pinacol ester, or —BF$_3^-$K, under Suzuki coupling conditions,
or
[C] the compounds of the formula

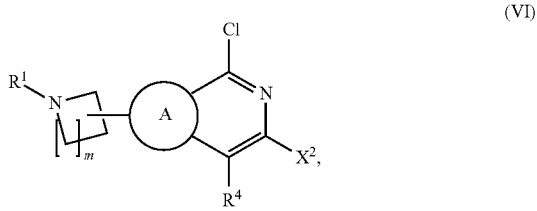

in which
A, m, $R^1$, $R^2$ and $R^4$ have the meaning given above,
are reacted with compounds of the formula

$$H\text{—}R^{13} \quad (IX),$$

in which
$R^{13}$ has the meaning given above.

The reaction according to process [A] is generally carried out in inert solvents, where appropriate in the presence of a base, where appropriate in a microwave, preferably in a temperature range from 50° C. to 200° C. under atmospheric pressure up to 3 bar.

Examples of bases are alkali metal carbonates, such as, for example, sodium carbonate, potassium carbonate or cesium carbonate, or organic bases, such as trialkylamines, for example triethylamine, N-methylmorpholine, N-methylpiperidine, 4-dimethylaminopyridine or diisopropylethylamine, or other bases, such as, for example, sodium hydride or potassium tert-butoxide; preference is given to diisopropylethylamine or sodium hydride.

Examples of inert solvents are halogenated hydrocarbons, such as methylene chloride or trichloromethane, alcohols, such as methanol, ethanol, n-propanol or isopropanol, or ethers, such as dioxane or tetrahydrofuran, or other solvents, such as, for example, dimethyl sulfoxide, dimethylformamide or N-methylpyrrolidone, or mixtures of these solvents; preference is given to isopropanol or dimethyl sulfoxide.

The reaction according to process [B] is generally carried out in inert solvents, in the presence of a catalyst, where appropriate in the presence of an additive, where appropriate in a microwave, preferably in a temperature range from room temperature to 150° C. under atmospheric pressure up to 3 bar.

Examples of catalysts for Suzuki reaction conditions are customary palladium catalysts; preference is given to catalysts such as, for example, dichlorobis(triphenylphosphine)palladium, tetrakistriphenylphosphinepalladium(0), palladium(II) acetate/triscyclohexylphosphine, bis(diphenylphosphaneferrocenyl)palladium(II) chloride, 1,3-bis(2,6-diisopropylphenyl)imidazol-2-ylidene(1,4-naphthtoquinone)palladium dimer, allyl(chloro)(1,3-dimesityl-1,3-dihydro-2H-imidazol-2-ylidene)palladium or palladium(II) acetate/dicyclohexyl-(2',4',6'-triisopropylbiphenyl-2-yl)phosphine. Another suitable source of palladium is tris(dibenzylideneacetone)dipalladium.

Examples of additives are potassium acetate, cesium carbonate, potassium carbonate or sodium carbonate, potassium tert-butoxide, cesium fluoride or potassium phosphate; preference is given to additives such as, for example, potassium acetate and/or saturated sodium carbonate solution.

Examples of inert solvents are ethers, such as dioxane, tetrahydrofuran or 1,2-dimethoxyethane, hydrocarbons, such as benzene, xylene or toluene, or carboxamides, such as dimethylformamide or dimethylacetamide, alkyl sulfoxides, such as dimethyl sulfoxide, or N-methylpyrrolidone or acetonitrile, or mixtures of the solvents with alcohols, such as methanol or ethanol, and/or water; preference is given to dioxane or acetonitrile or a mixture of one of these solvents with water.

The reaction according to process [C] is carried out under the reaction conditions stated under process [A].

The compounds of the formulae (III), (V) and (IX) are known or can be prepared by known processes from appropriate starting materials.

The compounds of the formula (VI) are known, they can be synthesized by known processes from the appropriate starting materials or they can be prepared analogously to the processes described in the example section (Examples 30A to 55A).

The compounds of the formula (II) are known or can be prepared by reacting compounds of the formula

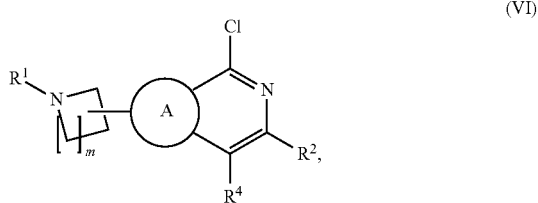

in which

A, m, $R^1$, $R^2$ and $R^4$ have the meaning given above, with compounds of the formula

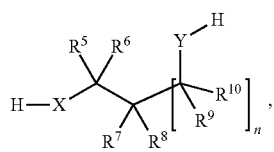

(VII)

in which n, X, Y, $R^5$, $R^6$, $R^7$, $R^8$, $R^9$ and $R^{10}$ have the meaning given above.

The reaction is carried out under the reaction conditions stated under process [A].

During the reaction, the radical Y is optionally protected by a protective group known to the person skilled in the art which is removed by standard processes after the reaction.

The compounds of the formula (VII) are known or can be synthesized by known processes from the appropriate starting materials.

The compounds of the formula (IV) are known or can be prepared by reacting compounds of the formula

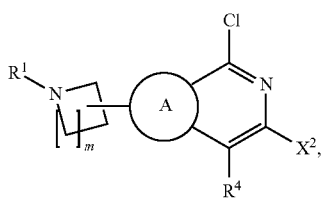

(VIII)

in which

A, m, $R^1$, $R^4$ and $X^2$ have the meaning given above, with compounds of the formula $$H\text{—}R^{13} \qquad (IX),$$

in which $R^{13}$ has the meaning given above.

The reaction is carried out under the reaction conditions mentioned under process [A].

The compounds of the formula (VIII) are known, they can be synthesized by known processes from the appropriate starting materials or they can be prepared analogously to the processes described in the example section (Examples 9A to 11A and Examples 50A to 53A).

The preparation of the starting materials and the compounds of the formula (I) can be illustrated by the synthesis schemes below.

Scheme 1:

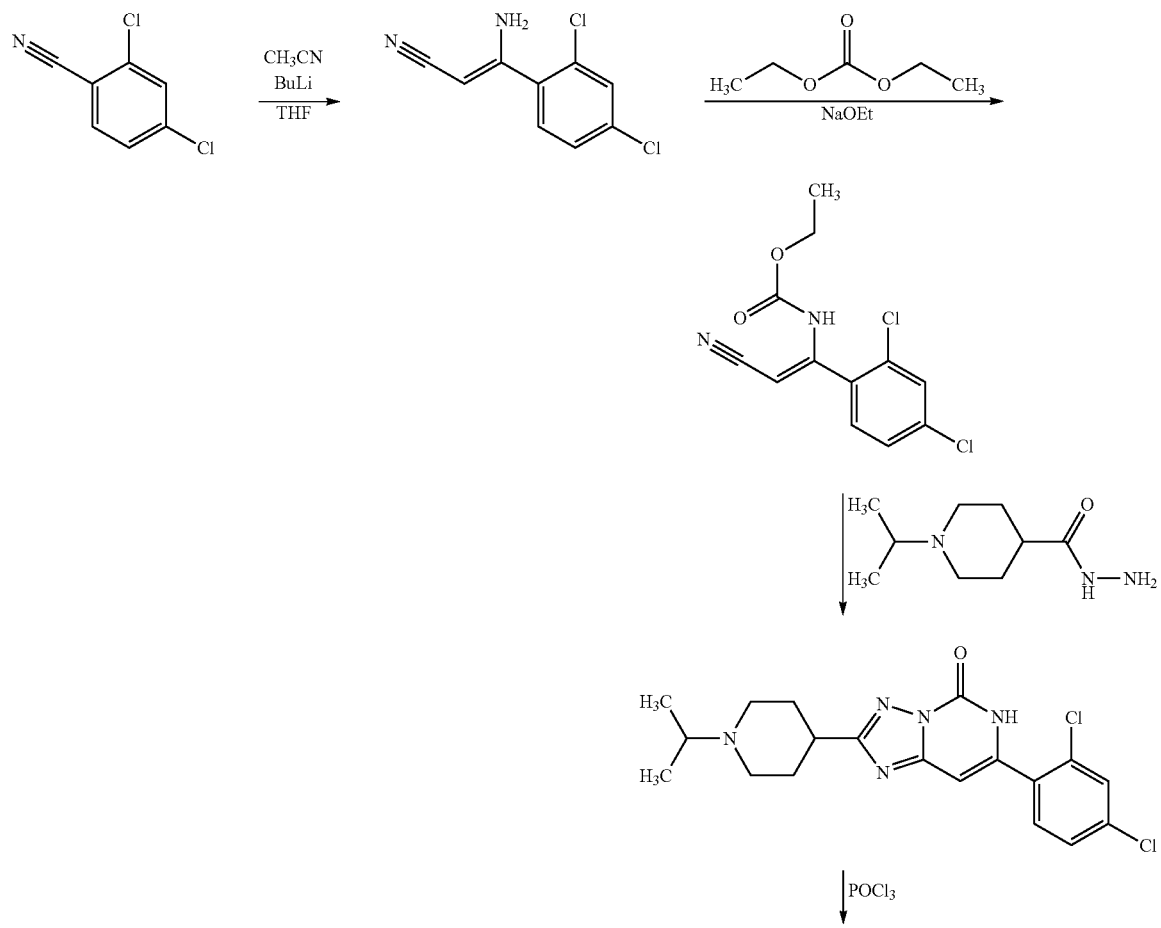

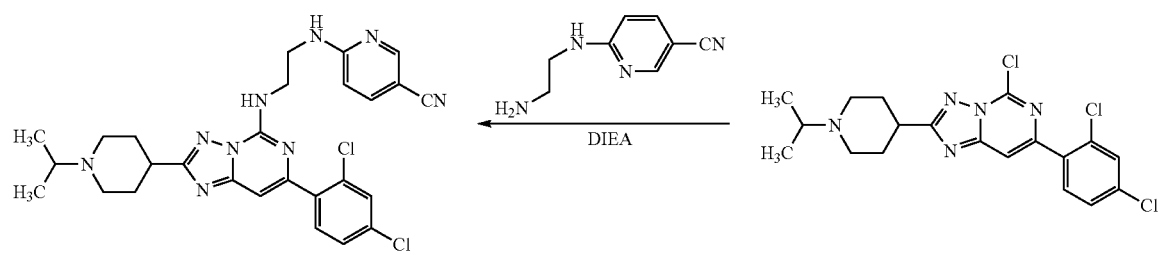
Scheme 2:
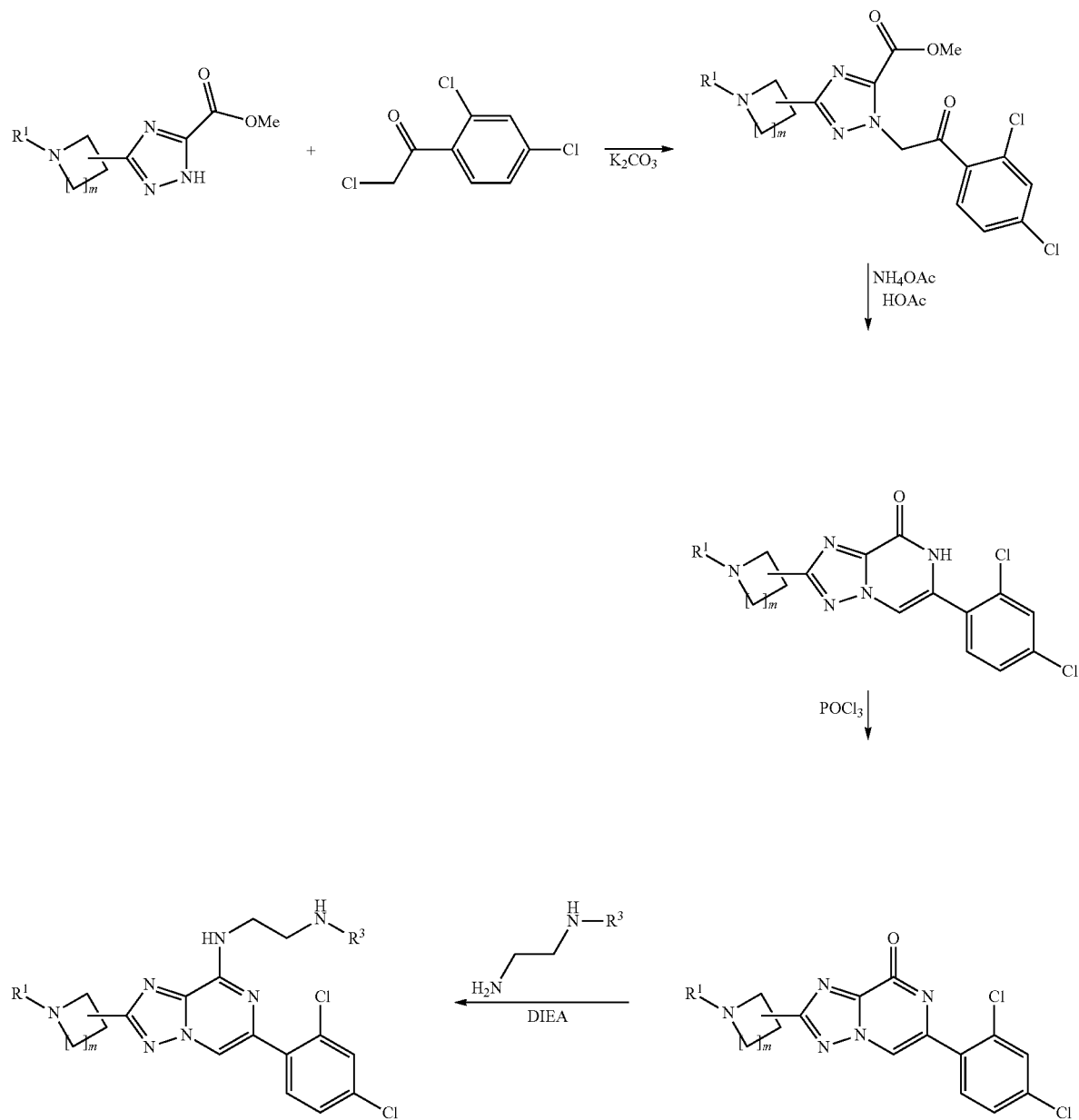

Scheme 3:
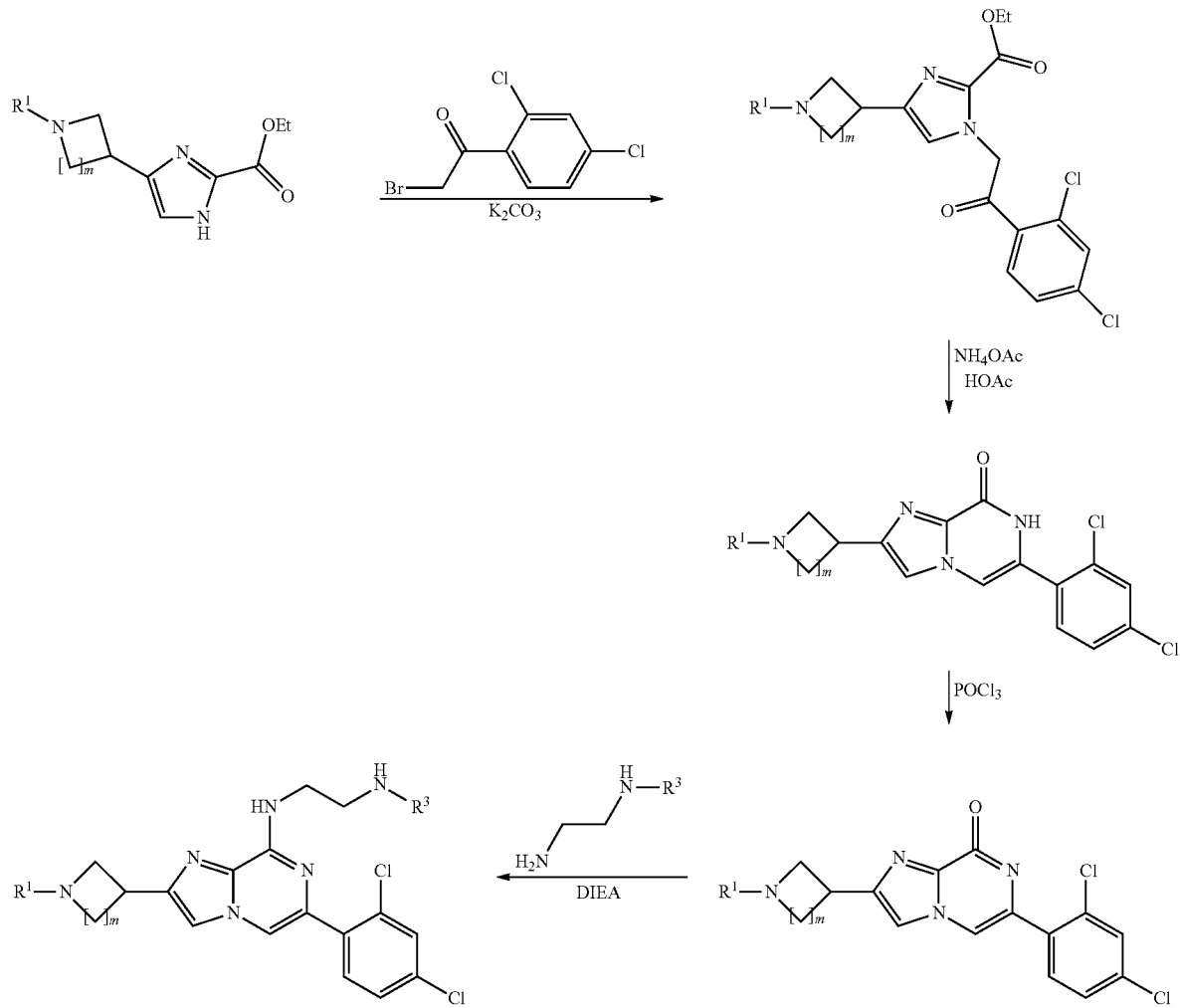
Scheme 4:
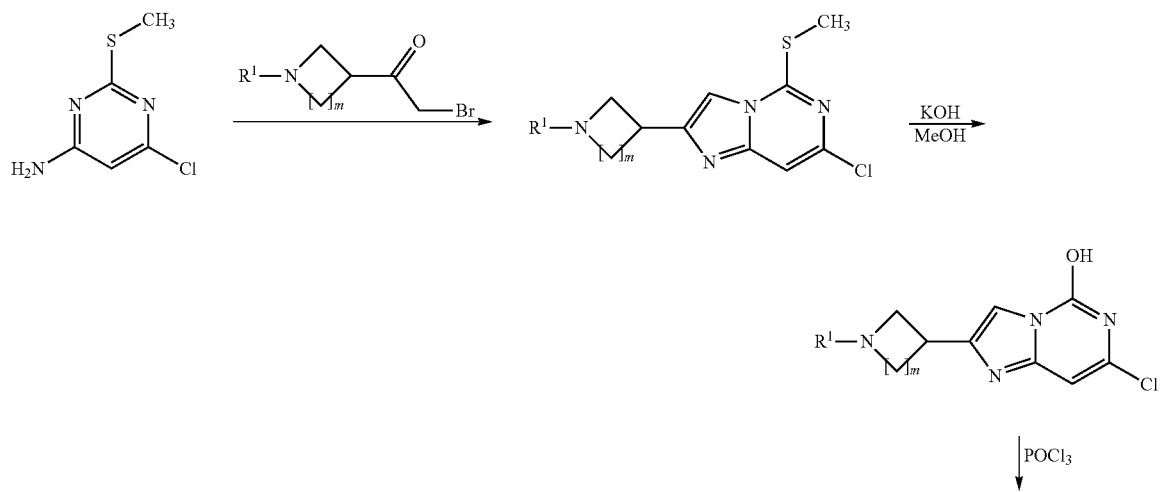

25 26
-continued
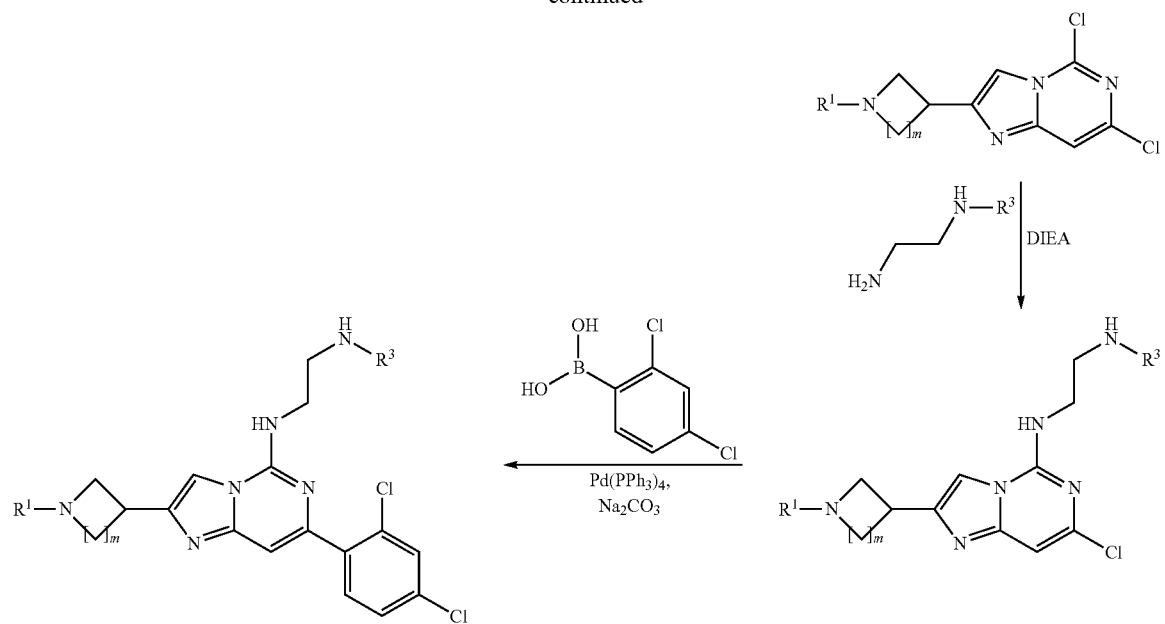
Scheme 5:
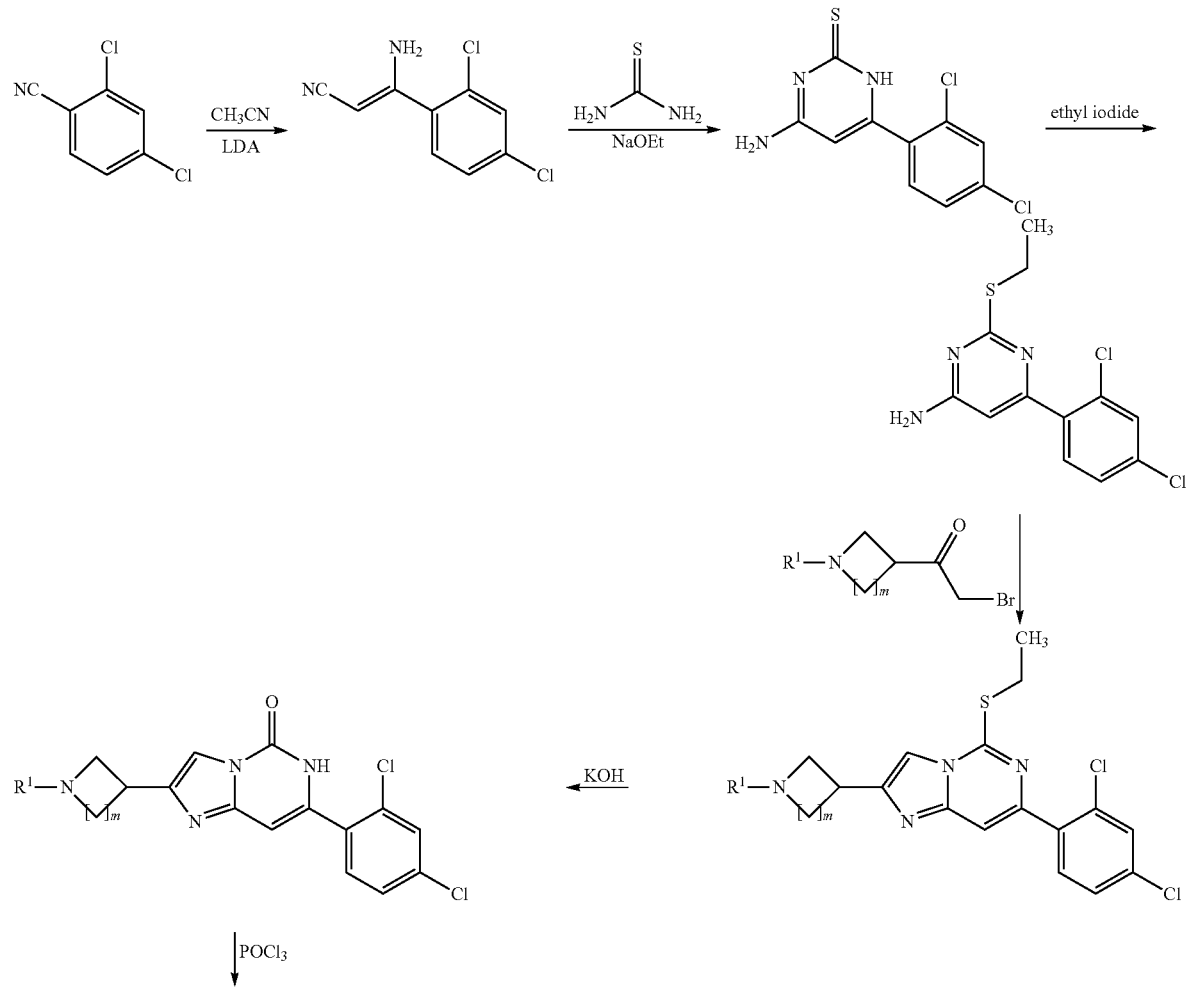

27 28
-continued
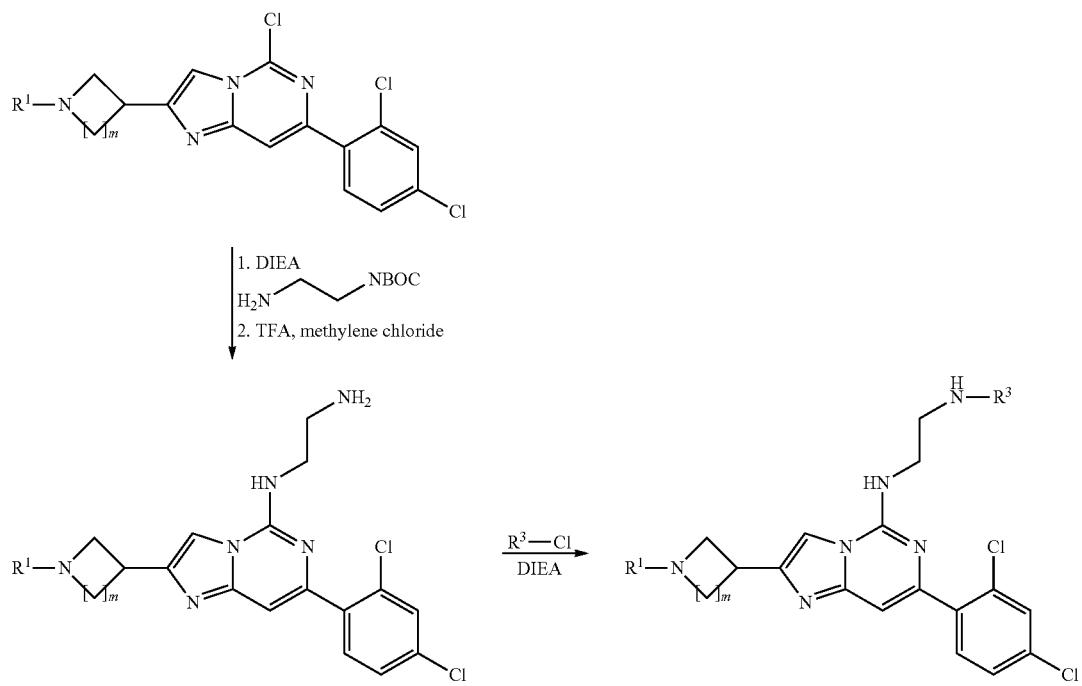
Scheme 6:
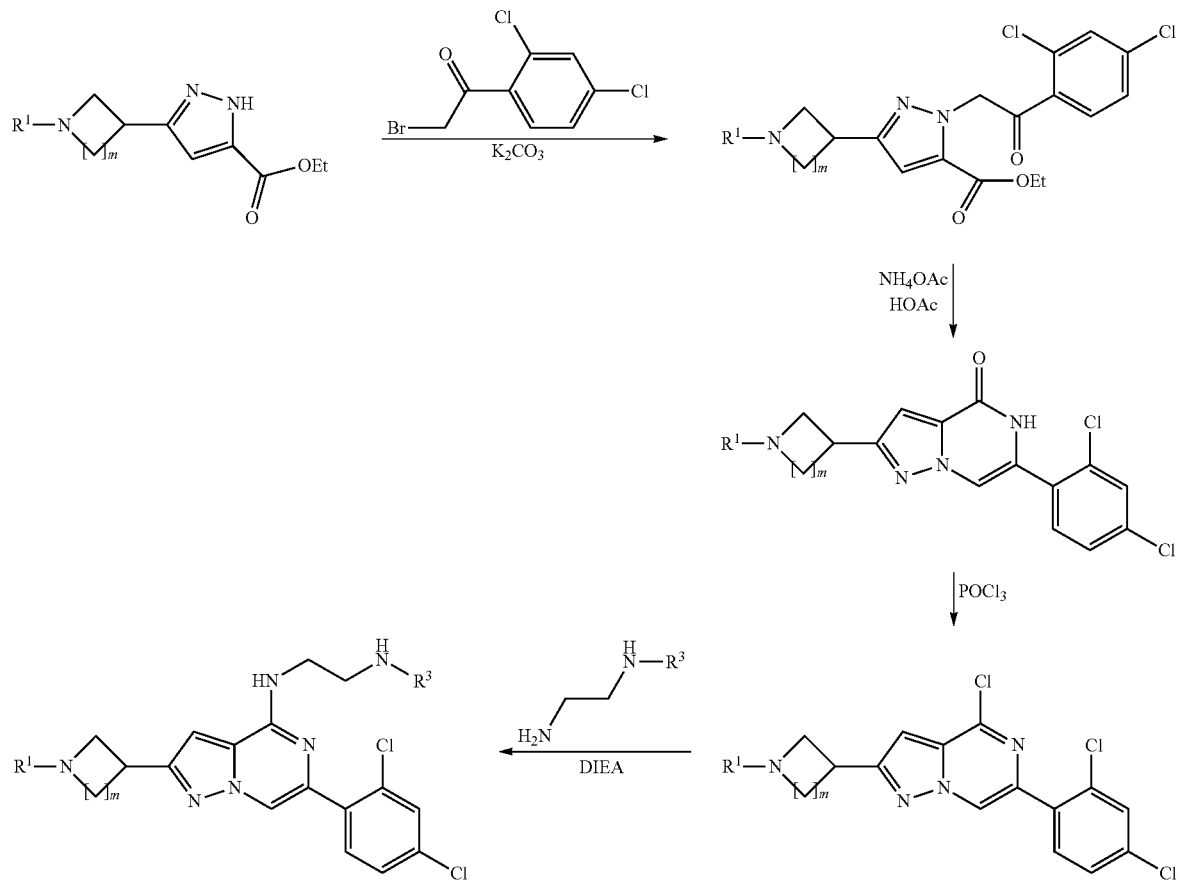

The compounds according to the invention show a valuable range of pharmacological and pharmacokinetic effects which could not have been predicted.

They are therefore suitable for use as medicaments for the treatment and/or prophylaxis of diseases in humans and animals.

The present invention further relates to the use of the compounds according to the invention for the treatment and/or prophylaxis of disorders, preferably hematological disorders, especially of leukopenias and neutropenia.

The compounds according to the invention are therefore suitable for the prophylaxis and/or treatment of neurodegenerative disorders such as, for example, Alzheimer's, Parkinson's, schizophrenia, degeneration, dementia, depression, aggression, cerebrovascular ischemia, sleep disorders, Huntington's chorea, neurotraumatic disorders such as, for example, stroke; type 2 diabetes mellitus and associated disorders such as, for example, the metabolic syndrome or obesity, type 1 diabetes mellitus, diabetic nephropathy, diabetic neuropathy, diabetic retinopathy, glomerulonephritis, hypercalcemia, hyperglycemia, hyperlipidemia, glucose-galactose malabsorption, general endocrine dysfunctions such as, for example, pancreatitis; hematological disorders such as, for example, acquired and congenital neutropenia, medicament-induced neutropenia, parasite-induced neutropenia, chemotherapy-induced neutropenia, granulocytopenia, acquired and congenital leukopenia, acquired and congenital anemia, hemolytic anemia, sickle cell anemia, acquired and congenital thrombocytopenia, leukocyte dysfunctions, impairments of blood coagulation, ex vivo expansion of embryonic and adult stem cells, ex vivo differentiation of embryonic and adult stem cells, bone marrow, graft-versus-host reaction; cancer such as, for example, glaucoma, breast carcinoma, colon tumor, gastrointestinal tumors, Hodgkin's lymphoma, non-Hodgkin's lymphoma, Kaposi sarcoma, liver tumor, pancreatic tumor, skin tumor, bone marrow tumor, leukemias such as, for example, acute lymphatic leukemia, acute myeloid leukemia, chronic myeloid leukemia, chronic lymphatic leukemia, prostate tumors, lung cancer, renal tumors; asthma, progressive, not completely reversible obstruction of the respiratory tract, pneumonia, pulmonary dysfunction; inflammatory disorders such as, for example, autoimmune diseases such as multiple sclerosis, rheumatoid arthritis, infections by gram-negative and gram-positive bacteria, viral infections, fungal infections such as, for example, by Candida albicans, HIV infections and HIV-associated infections, hepatitis of types A, B and C, parasitic infections; hair loss; reduced sperm mobility; wound healing; osteoporosis, bone marrow disorders, bone and joint disorders; cardiovascular disorders such as, for example, cardiac defects, heart failure, cardiac fibrosis, cardiac arrhythmias, myocardial infarction, medicament- or substance-induced cardiotoxicity, atherosclerosis, high blood pressure; sepsis; inflammatory disorders; pemphigus vulgaris.

The compounds according to the invention are particularly suitable for the prophylaxis and/or treatment of neurodegenerative disorders such as, for example, Alzheimer disease and schizophrenia, of type 2 diabetes mellitus and associated disorders, of cancer, of leukopenias and/or of neutropenias.

The compounds according to the invention are particularly suitable for the prophylaxis and/or treatment of leukopenias and/or of neutropenias.

The compounds according to the invention can additionally be employed also for efficient ex vivo expansion of adult haematopoietic stem cells from the bone marrow and/or from peripheral blood and/or for ex vivo expansion of embryonal stem cells from umbilical cord blood.

The compounds according to the invention can additionally be employed also for ex vivo expansion of embryonal and/or adult stem cells and for ex vivo differentiation of embryonal and/or adult stem cells.

These cells expanded in this way can then be used to curtail the cytopenias induced by myeloablative therapies or within the framework of therapeutic transplantation methods or for haematological systemic disorders such as, for example, leukaemias, or with cells which have been genetically manipulated after expansion for gene therapies.

The present invention further relates to the use of the compounds according to the invention for the treatment and/or prophylaxis of disorders, especially of the aforementioned disorders.

The present invention further relates to the compounds according to the invention for use in a method for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to a method for the treatment and/or prophylaxis of disorders, in particular of the aforementioned disorders, by use of a therapeutically effective amount of a compound according to the invention.

The present invention further relates to medicaments comprising a compound according to the invention and one or more further active ingredients, in particular for the treatment and/or prophylaxis of the aforementioned disorders. Suitable active ingredients in the combination which may be mentioned by way of example and preferably are:

A combination of the compounds according to the invention with chemotherapeutic agents used clinically may lead to a significantly improved result of treatment for various neoplastic diseases. The chemotherapeutic agents are substances which either inhibit the rate of division of tumour cells and/or prevent neovascularization of solid tumours. These include substances inter alia from the group of taxanes such as, for example, paclitaxel, or docetaxel, substances which inhibit the mitosis of tumour cells, such as, for example, vinblastine, vincristine, vindesine or vinorelbine. Substances from the class of platinum derivatives such as, for example, cisplatin, carboplatin, oxaliplatin, nedaplatin or lobaplatin. The chemotherapeutic agents further include substances from the class of alkylating agents such as, for example, cyclophosphamide, ifosfamide, melphalan, chlorambucil, pipobroman, triethylene melamine, busulphan, carmustine, lomustine, streptozin, dacarbazine or temozolomide. The chemotherapeutic agents also include antimetabolites such as, for example, folic acid antagonists, pyrimidine analogues, purine analogues or adenosine deaminase inhibitors. This class of substances includes inter alia methotrexate, 5-fluorouracil, floxuridine, cytarabine, pentostatin and gemcitabine. Also employed as chemotherapeutic agents are natural products or derivatives thereof, which include inter alia enzymes, antitumour antibodies and lymphokines. These include for example bleomycin, dactinomycin, daunorubicin, doxorubicin, epirubicin, idarubicin, ara-V, paclitaxel, mithramycin, mitomycin-C, L-asparaginase, interferons (e.g. IFN-alpha) and etoposide. Other chemotherapeutic agents with antiproliferative and/or anti-angiogenic effect are sorafenib, sunitinib, bortezomib, DAST inhibitor (BAY 73-4506) inter alia.

The present invention further relates to a method for the ex vivo expansion of adult hematopoietic stem cells from bone marrow, from peripheral blood or from umbilical cord blood, which is characterized in that an effective amount of the compound according to the invention is added.

The compounds of the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

The present invention further relates to medicaments which comprise at least one compound of the invention, preferably together with one or more inert, non-toxic, pharmaceutically suitable excipients, and to the use thereof for the aforementioned purposes.

It has generally proved advantageous on parenteral administration to administer amounts of about 5 to 1500 mg every 24 hours to achieve effective results. The amount on oral administration is about 5 to 5 to 2000 mg every 24 hours.

It may nevertheless be necessary where appropriate to deviate from the stated amounts, in particular as a function of the body weight, route of administration, individual response to the active ingredient, nature of the preparation and time or interval over which administration takes place.

The percentage data in the following tests and examples are, unless indicated otherwise, percentages by weight; parts are parts by weight. Solvent ratios, dilution ratios and concentration data of liquid/liquid solutions are in each case based on volume. The statement "w/v" means "weight/volume". Thus, for example, "10% w/v" means: 100 ml of solution or suspension comprise 10 g of substance.

A) EXAMPLES

Abbreviations:
abs. absolute
Boc tert-butoxycarbonyl
$CDCl_3$ deuterochloroform
$CO_2$ carbon dioxide
d day
DIEA N,N-diisopropylethylamine
DMAP 4-N,N-dimethylaminopyridine
DMF dimethylformamide
DMSO dimethyl sulfoxide
EDC N'-(3-dimethylaminopropyl)-N-ethylcarbodiimide×HCl
eq. equivalent
ESI electrospray ionization (in MS)
sat. saturated
h hour
HOBt 1-hydroxy-1H-benzotriazole×$H_2O$
HPLC high pressure, high performance liquid chromatography
conc. concentrated
LC-MS coupled liquid chromatography-mass spectrometry
min minutes
MS mass spectrometry
MW molecular weight [g/mol]
NMR nuclear magnetic resonance spectroscopy
PyBOP 1-benzotriazolyloxytripyrrolidinophosphonium hexafluorophosphate
$R_f$ retention index (in TLC)
RP-HPLC reverse phase HPLC
RT room temperature
$R_t$ retention time (in HPLC)
TBTU (benzotriazol-1-yloxy)bisdimethylaminomethylium fluoroborate
TFA trifluoroacetic acid
THF tetrahydrofuran
LC-MS Methods:

Method 1: Instrument: Micromass Quattro LCZ with HPLC Agilent series 1100; column: Phenomenex Synergi 2.5μ MAX-RP 100A mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 2: MS instrument type: Micromass ZQ; HPLC instrument type: Waters Alliance 2795; column: Merck Chromolith SpeedROD RP-18e 100 mm×4.6 mm; eluent A: water+500 μl of 50% formic acid/l; eluent B: acetonitrile+500

μl of 50% formic acid/l; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm Method 3: MS instrument type: Micromass ZQ; HPLC instrument type: HP 1100 Series; UV DAD; column: Phenomenex Gemini 3μ 30 mm×3.00 mm; eluent A: 1 l of water+ 0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4: Instrument: Micromass Platform LCZ with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5: MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient 0.0 min 90% A→2 min 65% A→4.5 min 5% A→6 min 5% A; flow rate: 2 ml/min; oven: 40° C.; UV detection: 210 nm.

Method 6: MS instrument type: Micromass ZQ; HPLC instrument type: Waters Alliance 2795; column: Phenomenex Synergi 2.5μ MAX-RP 100A mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 7: Instrument: Micromass Quattro LCZ with HPLC Agilent series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 8: Instrument: Micromass QuattroPremier with Waters UPLC Acquity; column: Thermo Hypersil GOLD 1.9μ 50 mm×1 mm; eluent A: 1 l of water+0.5 ml of 50% formic acid, eluent B: 1 l of acetonitrile+0.5 ml of 50% formic acid; gradient: 0.0 min 100% A→0.1 min 100% A→1.5 min 10% A→2.2 min 10% A; oven: 50° C.; flow rate: 0.33 ml/min; UV detection: 210 nm.

Method 9: Instrument: Micromass Quattro Micro MS with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A→5.00 min 100% A; flow rate: 0.0 min/3.0 min/4.0 min/4.01 min 2.5 ml/min, 5.00 min 2 ml/min; oven: 50° C.; UV detection: 210 nm.

GC-MS Methods:

Method 10: Instrument: Micromass GCT, GC6890; column: Restek RTX-35, 15 m×200 μm×0.33 μm; constant helium flow: 0.88 ml/min; oven: 70° C.; inlet: 250° C.; gradient: 70° C., 30° C./min→310° C. (maintained for 3 min)

Preparative HPLC:

Method 11: Preparative HPLC: column: Reprosil C18; gradient: acetonitrile/water.

The microwave reactor used was a single mode apparatus of the Emrys™ Optimizer type.

Starting Materials

Example 1A tert-Butyl{2-[(5-cyanopyridin-2-yl)amino]ethyl}carbamate

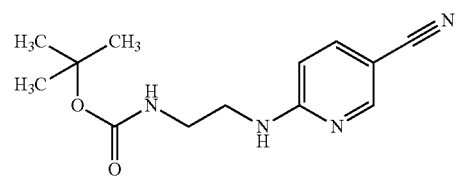 [SMILES: CC(C)(C)OC(=O)NCCNc1ccc(C#N)cn1]

5.5 g (39.7 mmol) of 6-chloronicotinonitrile were dissolved in 70 ml of DMSO, and 10.2 g (63.5 mmol) of N-Boc-ethylenediamine and 11 g (79.4 mmol) of potassium carbonate were added. The mixture was stirred at 90° C. for 12 h. The residue was taken up in a mixture of water and ethyl acetate. The organic phase was washed with saturated aqueous sodium chloride solution, dried over magnesium sulfate and concentrated on a rotary evaporator. The residue was chromatographed on silica gel 60 (mobile phase: cyclohexane/ethyl acetate 10:1 to 2:1). This gave 7.9 g (77% of theory) of the product as a solid.

LCMS (Method 6): $R_t$=1.46 min. (m/z=263 (M+H)$^+$)

$^1$H-NMR (400 MHz, DMSO-d$_6$): δ=8.37 (d, 1H), 7.66 (d, 1H) 7.6 (s, 1H), 6.87 (t, 1H), 6.53 (d, 1H), 3.32 (q, 2H), 3.09 (q, 2H), 1.37 (s, 9H).

Example 2A

6-[(2-Aminoethyl)amino]nicotinonitrile dihydrochloride

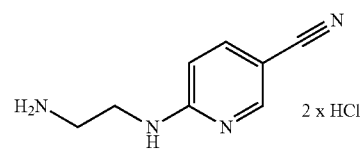 [SMILES: N#Cc1ccc(NCCN)nc1]

7.9 g (30 mmol) of tert-butyl{2-[(5-cyanopyridin-2-yl)amino]ethyl}carbamate (Example 1A) were dissolved in 100 ml of 4 N hydrogen chloride in dioxane and stirred for 30 min. The reaction mixture was concentrated to half of its original volume and the same amount of diethyl ether was added. The reaction mixture was stirred for 20 min, and the product was filtered off and washed with diethyl ether. This gave 7 g (94% of theory) of the product as a solid.

LCMS (Method 4): $R_t$=0.51 min. (m/z=162 (M+H)$^+$)

$^1$H-NMR (400 MHz, DMSO-d$_6$): δ=8.44 (s, 1H), 7.76 (d, 1H), 6.67 (d, 1H), 3.58 (t, 2H), 2.98 (q, 2H).

Example 3A tert-Butyl(6-chloropyridin-2-yl)carbamate

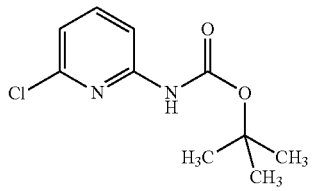

Under argon, 150 ml of THF were added to 23.4 g (181.8 mmol) of 2-chloro-5-aminopyridine, and the mixture was cooled to 0° C. 73.3 g (400 mmol) of sodium bis(trimethylsilyl)amide and 43.65 g (200 mmol) of di-tert-butyl dicarbonate, dissolved in 150 ml of THF, were added dropwise. After 15 min, the cooling bath was removed and stirring was continued at RT for 15 min. The THF was removed on a rotary evaporator, ethyl acetate and 0.5N hydrochloric acid were added to the residue and the mixture was extracted. The organic phase was separated off, dried over magnesium sulfate and concentrated on a rotary evaporator. The reaction mixture was chromatographed on silica gel (mobile phase dichloromethane/methanol 100%→100:3). This gave 36.54 g (88% of theory) of the product as a solid.

LCMS (Method 3): $R_t$=2.41 min. (m/z=175 (M+H)$^+$).
$^1$H-NMR (400 MHz, DMSO-d$_6$): δ=10.11 (s, 1H), 7.78 (d, 2H), 7.1 (t, 1H), 1.47 (s, 9H).

Example 4A tert-Butyl(6-chloro-3-formylpyridin-2-yl)carbamate

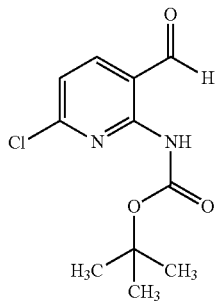 [SMILES: CC(C)(C)OC(=O)Nc1nc(Cl)ccc1C=O]

The reaction apparatus was dried by heating, and the reaction was carried out under argon and with stirring. 15 g (65.6 mmol) of tert-butyl(6-chloropyridin-2-yl)carbamate (Example 3A) and 19 g (164 mmol) of 1,2-bis(dimethylamino)ethane were initially charged in 270 ml of THF and cooled to –78° C. 102.5 ml (164 mmol) of butyllithium (1.6 N) were added dropwise. After the end of the dropwise addition, the reaction was slowly warmed to –10° C. and kept at –10° C. for 2 h. The mixture was then once more cooled to –78° C., and 10 ml (131 mmol) of DMF were added. The reaction was slowly warmed to RT, the reaction mixture was added to 1 l of ethyl acetate and 350 ml of 1 N hydrochloric acid and stirred for 15 min, and the organic phase was separated off. The organic phase was washed with water and saturated sodium bicarbonate solution, dried over magnesium sulfate and concentrated on a rotary evaporator. Diethyl ether was added to the residue and the solid was filtered off with suction and dried. This gave 12.3 g (73% of theory) of the product as a solid.

LCMS (Method 3): $R_t$=2.19 min. (m/z=255 (M+H)$^-$).
$^1$H-NMR (400 MHz, DMSO-d$_6$): δ=10.37 (s, 1H), 9.83 (s, 1H), 8.2 (d, 1H), 7.42 (d, 1H), 1.46 (s, 9H).

Example 5A tert-Butyl{6-chloro-3-[(hydroxyimino)methyl]pyridin-2-yl}carbamate

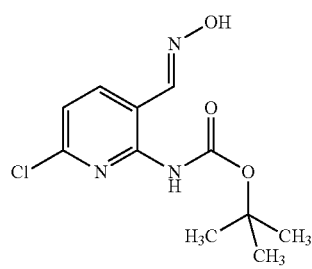 [SMILES: CC(C)(C)OC(=O)Nc1nc(Cl)ccc1/C=N/O]

15.45 g (60.2 mmol) of tert-butyl(6-chlor-3-formylpyridin-2-yl)carbamate (Example 4A) were initially charged in 750 ml of ethanol, a solution of 225 ml of water and 9.38 g (120.4 mmol) of sodium acetate was added and the mixture was stirred for 5 min. A solution of 225 ml of water and 8.36 g (114.4 mmol) of hydroxylamine hydrochloride was added, and the mixture was stirred at RT for 4 h. At 20° C., the reaction mixture was concentrated on a rotary evaporator. The residue was taken up in ethyl acetate and washed twice with saturated sodium bicarbonate solution and once with saturated sodium chloride solution. The organic phase was separated off, dried over magnesium sulfate and concentrated at 20° C. on a rotary evaporator. This gave 15.5 g (80% of theory) of the product as a solid.

LCMS (Method 3): $R_t$=2.08 min. (m/z=270 (M+H)$^-$).
$^1$H-NMR (400 MHz, DMSO-d$_6$): δ=11.71 (s, 1H), 9.91 (s, 1H), 8.14 (s, 1H), 8.02 (d, 1H), 7.3 (d, 1H), 1.49 (s, 9H).

Example 6A

2-Amino-6-chloropyridine-3-carbaldehyde oxime hydrochloride

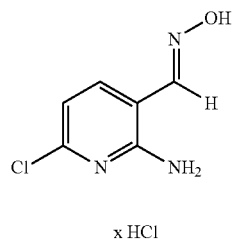 [SMILES: Nc1nc(Cl)ccc1/C=N/O]

15.5 g (57 mmol) of tert-butyl{6-chloro-3-[(hydroxyimino)methyl]pyridin-2-yl}carbamate (Example 5A) were dissolved in 285 ml of 4 N hydrogen chloride in dioxane, and the mixture was stirred for 30 min. The reaction mixture was concentrated to half of its original volume, and the same amount of diethyl ether was added. The reaction mixture was stirred for 20 min, and the product was filtered off and washed with diethyl ether. This gave 11 g (94% of theory) of the product as a solid.

LCMS (Method 6): $R_t$=1.09 min. (m/z=172 (M+H)$^+$)

$^1$H-NMR (400 MHz, DMSO-d$_6$): δ=8.27 (s, 1H), 7.61 (d, 1H), 6.65 (d, 1H).

Example 7A

2-Amino-6-chloropyridine-3-carbonitrile

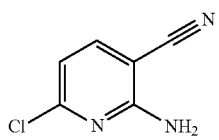

11.15 g (53.6 mmol) of 2-amino-6-chloropyridine-3-carbaldehyde oxime hydrochloride (Example 6A) were initially charged in dioxane, 13 ml (161 mmol) of pyridine were added and the mixture was cooled to 0° C. 8.3 ml (58.95 mmol) of trifluoroacetic anhydride were added, and the reaction was warmed to RT and then stirred at 60° C. for 2 h. The reaction mixture was taken up in a mixture of ethyl acetate and sodium bicarbonate solution. The organic phase was washed with saturated sodium chloride solution, dried over magnesium sulfate and concentrated on a rotary evaporator. The residue was suspended in dichloromethane:diethyl ether 3:1, and the solid was filtered off with suction and dried. This gave 5.56 g (66% of theory) of the product as a solid.

LCMS (Method 6): $R_t$=1.0 min. (m/z=154 (M+H)$^+$).

$^1$H-NMR (400 MHz, DMSO-d$_6$): δ=7.91 (d, 1H), 7.38 (s, 2H), 6.69 (d, 1H).

Example 8A tert-Butyl{2-[(6-amino-5-cyanopyridin-2-yl)amino]ethyl}carbamate

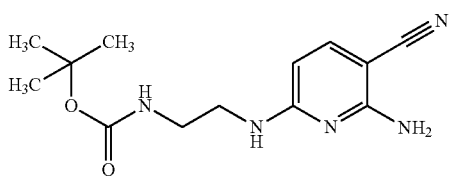 [SMILES: CC(C)(C)OC(=O)NCCNc1ccc(C#N)c(N)n1]

2 g (13 mmol) of 2-amino-6-chloropyridine-3-carbonitrile (Example 7A) were initially charged in 15 ml of DMSO, and 2.71 g (16.93 mmol) of N-Boc-ethyleneamine and 3.4 ml (19.54 mmol) of N,N-diisopropylethylamine were added. The reaction mixture was irradiated in a microwave reactor at 115° C. for 1.5 h. The reaction mixture was taken up in a mixture of ethyl acetate and water. The organic phase was washed with saturated sodium chloride solution, dried over magnesium sulfate and concentrated on a rotary evaporator. This gave 23.38 g (88% of theory) of the product as a solid.

LCMS (Method 3): $R_t$=1.7 min. (m/z=278 (M+H)$^+$).

$^1$H-NMR (400 MHz, DMSO-d$_6$): δ=7.3 (s, 1H), 7.0 (br, s, 1H), 6.83 (s, 1H), 6.25 (s, 2H), 5.78 (d, 1H), 3.25 (q, 2H), 3.06 (q, 2H), 1.36 (s, 9H).

Example 9A

2-Amino-6-[(2-aminoethyl)amino]pyridine-3-carbonitrile dihydrochloride

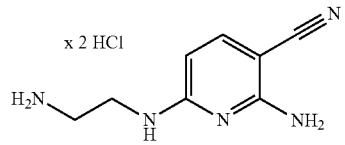 [SMILES: N#Cc1ccc(NCCN)nc1N]

6.76 g (24.38 mmol) of tert-butyl{2-[(6-amino-5-cyanopyridin-2-yl)amino]ethyl}carbamate (Example 8A) were dissolved in 122 ml of a 4 N solution of hydrogen chloride in dioxane and stirred for 30 min. The reaction mixture was concentrated to half of its original volume, and the same amount of diethyl ether was added. The reaction mixture was stirred for 20 min, and the product was filtered off and washed with diethyl ether. This gave 5.43 g (89% of theory) of the product as a solid.

LCMS (Method 6): $R_t$=0.92 min. (m/z=177 (M+H)$^+$)

$^1$H-NMR (400 MHz, DMSO-d$_6$): δ=8.1 (s, 2H), 7.5 (d, 1H), 5.96 (d, 1H), 3.53 (q, 2H), 3.0 (q, 2H).

Example 10A 4-(Trifluoroacetyl)morpholine

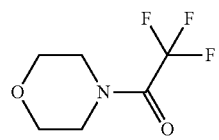 [SMILES: O=C(N1CCOCC1)C(F)(F)F]

15 g (172 mmol) of morpholine were initially charged in 750 ml of dichloromethane, and 29 ml (206 mmol) of trifluoroacetic anhydride and 119 ml (688 mmol) of N,N-diisopropylethylamine were added at 0° C. The reaction mixture was warmed to RT and stirred at RT for 3 h. The reaction mixture was concentrated and the residue was taken up in ethyl acetate and washed successively with aqueous sodium bicarbonate solution, 1N hydrochloric acid and once more with aqueous sodium bicarbonate solution. The organic phase was dried over magnesium sulfate and concentrated on a rotary evaporator. This gave 28 g (88% of theory) of the product as an oil.

LCMS (Method 9): $R_t$=1.22 min. (m/z=184 (M+H)$^+$)

$^1$H-NMR (400 MHz, DMSO-d$_6$): δ=3.65 (m, 2H), 3.56 (m, 2H).

Example 11A tert-Butyl[6-chloro-3-(trifluoroacetyl)pyridin-2-yl]carbamate

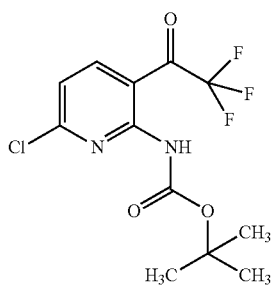 [SMILES: CC(C)(C)OC(=O)Nc1nc(Cl)ccc1C(=O)C(F)(F)F]

8 g (35 mmol) of tert-butyl(6-chloropyridin-2-yl)carbamate (Example 3A) were initially charged in 100 ml of THF and cooled to −50° C. 55 ml (87 mmol) of butyllithium (1.6 N) were added dropwise. After the dropwise addition had ended, the reaction was slowly warmed to −10° C. and stirred at 0° C. for 2 h. The mixture was then cooled again to −40° C., and 12.8 g (70 mmol) of 4-(trifluoroacetyl)morpholine (Example 10A), dissolved in 4 ml of THF, were added. The reaction solution was stirred at −40° C. for 1 h and then, at −40° C., poured into 1 l of ethyl acetate and 350 ml of ammonium chloride solution and extracted. The organic phase was separated off, dried over magnesium sulfate and concentrated on a rotary evaporator. The reaction mixture was chromatographed on silica gel (mobile phase cyclohexane/ethyl acetate 10:1). This gave 9 g (79% of theory) of the product as an oil.

$^1$H-NMR (400 MHz, DMSO-$d_6$): δ=10.96 (s, 1H), 7.99 (d, 1H), 7.4 (d, 1H), 1.43 (s, 9H).

Example 12A tert-Butyl[6-({2-[(tert-butoxycarbonyl)amino]ethyl}amino)-3-(trifluoroacetyl)pyridin-2-yl]-carbamate

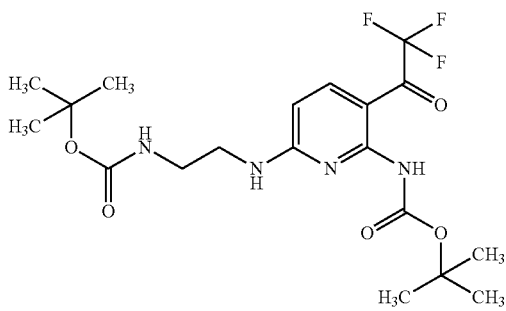 [SMILES: CC(C)(C)OC(=O)NCCNc1ccc(C(=O)C(F)(F)F)c(NC(=O)OC(C)(C)C)n1]

5 g (15.4 mmol) of tert-butyl-[6-chlor-3-(trifluoroacetyl)pyridin-2-yl]carbamate (Example 11A) were initially charged in 37.5 ml of DMSO, and 3.2 g (20 mmol) of N-Boc-ethylenediamine and 4 ml (23 mmol) of N,N-diisopropylethylamine were added. The reaction mixture was irradiated in a microwave reactor at 90° C. for 0.5 h. The reaction mixture was taken up in a mixture of ethyl acetate and water. The organic phase was washed with saturated sodium chloride solution, dried over magnesium sulfate and concentrated on a rotary evaporator. The reaction mixture was chromatographed on silica gel (mobile phase cyclohexane/ethyl acetate 5:1→1:1). This gave 2.5 g (34% of theory) of the product as a solid.

LCMS (Method 6): $R_t$=2.44 min. (m/z=449 (M+H)$^+$).

$^1$H-NMR (400 MHz, DMSO-$d_6$): δ=10.75 (s, 1H), 8.44 (s, 1H), 7.70 (d, 1H), 6.77 (s, 1H), 6.28 (d, 1H), 3.48 (br, s, 2H), 3.17 (br, s, 2H), 1.46 (s, 9H), 1.30 (s, 9H).

Example 13A

1-{2-Amino-6-[(2-aminoethyl)amino]pyridin-3-yl}-2,2,2-trifluoroethanone hydrochloride

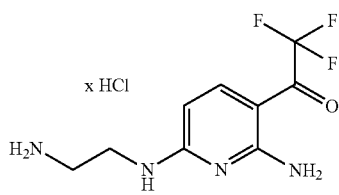 [SMILES: NCCNc1ccc(C(=O)C(F)(F)F)c(N)n1]

2.5 g (5.57 mmol) of tert-butyl-[6-({2-[(tert-butoxycarbonyl)amino]ethyl}amino)-3-(trifluoroacetyl)-pyridin-2-yl]carbamate (Example 12A) were dissolved in 15 ml of a 4 N solution of hydrogen chloride in dioxane and stirred for 20 h. The reaction mixture was concentrated to half of its original volume, and the same amount of diethyl ether was added. The reaction mixture was stirred for 20 min, and the product was filtered off and washed with diethyl ether. This gave 1.4 g (89% of theory) of the product as a solid.

LCMS (Method 6): $R_t$=0.73 min. (m/z=249 (M+H)$^+$).

Example 14A

4-Amino-2-(methylsulfonyl)-1,3-thiazole-5-carbonitrile

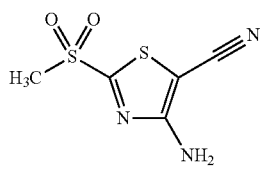

2.7 g (15.77 mmol) of 4-amino-2-(methylthio)-1,3-thiazole-5-carbonitrile were dissolved in 200 ml of dichloromethane, and 11.97 g (34.7 mmol) of 3-chloroperbenzoic acid were added. The mixture was stirred at RT for 30 min, 6 ml of DMSO and then saturated aqueous sodium bicarbonate solution were then added and the mixture was extracted three times with dichloromethane. The organic phase was dried over magnesium sulfate giving, after removal of the solvent, 2.22 g (46% of theory) of the product as an oil which was used without further purifications.

LCMS (Method 3): $R_t$=1.19 min. (m/z=204 (M+H)$^+$).

Example 15A tert-Butyl{2-[(4-amino-5-cyano-1,3-thiazol-2-yl)amino]ethyl}carbamate

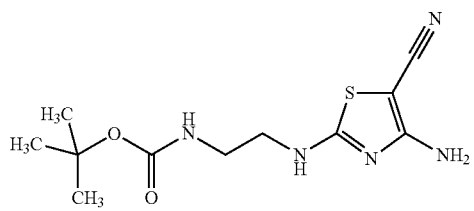 [SMILES: CC(C)(C)OC(=O)NCCNc1nc(N)c(C#N)s1]

2.2 g (7.22 mmol) of 4-amino-2-(methylsulfonyl)-1,3-thiazole-5-carbonitrile (Example 14A) were dissolved in 24 ml of DMSO, and 1.74 g (10.84 mmol) of N-Boc-ethylenediamine and 933 mg (7.22 mmol) of DIEA were added. The mixture was stirred for 16 h at 120° C., and water and ethyl acetate were added once the reaction had ended. The aqueous phase was extracted three times with ethyl acetate. The combined organic phases were dried over magnesium sulfate and purified by silica gel chromatography. This gave 633 mg (31% of theory) of the product.

LCMS (Method 6): $R_t$=1.45 min. (m/z=284 (M+H)$^+$).

$^1$H-NMR (400 MHz, DMSO-d$_6$): δ=8.35 (s, br, 1H), 6.90 (t, 1H), 6.68 (s, 2H), 3.22 (s, br, 2H), 3.07 (dd, 2H), 1.37 (s, 9H).

Example 16A

4-Amino-2-[(2-aminoethyl)amino]-1,3-thiazole-5-carbonitrile trifluoroacetate

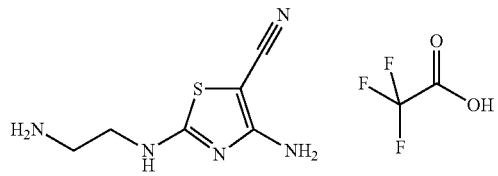 [SMILES: N#Cc1sc(NCCN)nc1N ; O=C(O)C(F)(F)F]

Analogously to the preparation of the cyanopyridine (Example 2A), 130 mg (0.46 mmol) of the Boc-protected amine (Example 15A) and 1.05 g (9.18 mmol) of trifluoroacetic acid gave, after removal of all volatile components, 130 mg (96% of theory) of the product.

LCMS (Method 4): $R_t$=0.61 min. (m/z=184 (M+H)$^+$).

$^1$H-NMR (400 MHz, DMSO-d$_6$): δ=8.45 (t, 1H), 7.84 (s, br, 2H), 6.80 (s, br, 1H), 3.93 (s, 1H), 3.43 (dd, 2H), 3.01 (dd, 2H).

Example 17A tert-Butyl 3-[(5-cyanopyridin-2-yl)amino]piperidine-1-carboxylate

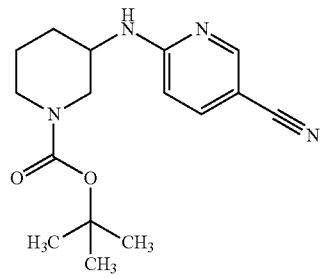 [SMILES: CC(C)(C)OC(=O)N1CCCC(Nc2ccc(C#N)cn2)C1]

1.0 g (4.99 mmol) of tert-butyl 3-aminopiperidine-1-carboxylate and 1.383 g (9.99 mmol) of 6-chloropyridine-3-carbonitrile and 1.29 g (9.99 mmol) of diisopropylethylamine were suspended in 40 ml of DMSO and heated in a microwave reactor at 140° C. for 45 min. Most of the DMSO was removed from the mixture by kugelrohr distillation, water was added and the resulting precipitate was filtered off. Drying under high vacuum gave 2.24 g (46% of theory) of the product.

LCMS (Method 3): $R_t$=2.23 min. (m/z=303 (M+H)$^+$).

Example 18A tert-Butyl 3-[(6-amino-5-cyanopyridin-2-yl)amino]piperidine-1-carboxylate

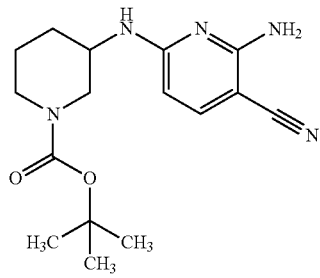 [SMILES: CC(C)(C)OC(=O)N1CCCC(Nc2ccc(C#N)c(N)n2)C1]

2.15 g (10.7 mmol) of tert-butyl 3-aminopiperidine-1-carboxylate, 1.50 g (9.77 mmol) of 2-amino-6-chloropyridine-3-carbonitrile (Example 7A) and 1.89 g (14.7 mmol) of diisopropylethylamine were suspended in 6 ml of DMSO and heated in a microwave reactor at 130° C. for 8 h. The reaction mixture was diluted with ethyl acetate (100 ml) and water (40 ml), and the organic phase was separated off and washed with saturated sodium chloride solution (50 ml), dried over magnesium sulfate and concentrated. The residue was chromatographed on silica gel (mobile phase: cyclohexane-ethyl acetate 4:1 to 1:1). This gave 2.04 g (60% of theory) of the product as a solid.

LCMS (Method 6): $R_t$=1.69 min. (m/z=318 (M+H)$^+$)

Example 19A 6-(Piperidin-3-ylamino)pyridine-3-carbonitrile hydrochloride

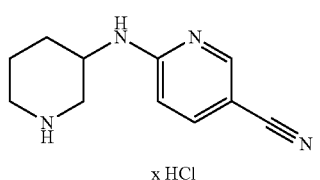 [SMILES: N#Cc1ccc(NC2CCCNC2)nc1]

2.24 g (7.4 mmol) of tert-butyl-3-[(5-cyanopyridin-2-yl)amino]piperidine-1-carboxylate (Example 17A) were dissolved in 4.3 ml of a solution of hydrochloric acid in dioxane (4 M), and the mixture was stirred at RT for 3 h. After the reaction had gone to completion, the solvent was removed completely. This gave 1.74 g (90% of theory) of the product as a solid.

LCMS (Method 8): $R_t$=0.27 min. (m/z=203 (M+H)$^+$)

$^1$H-NMR (400 MHz, DMSO-d$_6$): δ=9.13 (m, 1H), 9.0 (m, 1H), 8.44 (d, 1H), 7.89 (m, 1H), 7.74 (dd, 1H), 6.63 (d, 1H), 5.58 (s, br), 4.19 (s, br, 1H), 3.57 (s, 1H), 3.34 (d, 1H), 3.14 (d,

1H), 2.88 (m, 1H), 2.7-2.81 (m, 1H), 1.82-2.0 (m, 2H), 1.63-1.79 (m, 1H), 1.48-1.59 (m, 1H).

Example 20A

2-Amino-6-(piperidin-3-ylamino)pyridine-3-carbonitrile hydrochloride

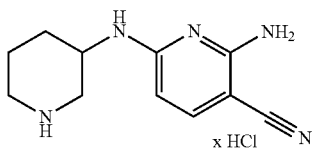 [SMILES: N#Cc1ccc(NC2CCCNC2)nc1N]

2.00 g (6.3 mmol) of tert-butyl 3-[(6-amino-5-cyanopyridin-2-yl)amino]piperidine-1-carboxylate (Example 7A) were dissolved in 40 ml of a solution of hydrochloric acid in dioxane (4 M), and the mixture was stirred at RT for 2 h. After the reaction had gone to completion, the solvent was concentrated to half of its original volume, and 20 ml of diethyl ether were added. The precipitate was filtered off and dried. This gave 1.80 g (100% of theory) of the product as a solid.

LCMS (Method 8): $R_t$=0.25 min. (m/z=218 (M+H)$^+$)

$^1$H-NMR (400 MHz, DMSO-d$_6$): δ=9.38 (br m, 1H), 8.97 (br m, 1H), 8.25 (br m, 1H), 7.53 (m, 1H), 7.40 (br s, 2H), 6.01 (d, 1H), 4.16 (br m, 1H), 3.34 (br m, 1H), 3.10 (m, 1H), 2.89 (m, 2H), 2.00-1.84 (m, 2H), 1.73 (m, 1H), 1.55 (m, 1H).

Example 21A tert-Butyl 3-({6-[(tert-butoxycarbonyl)amino]-5-(trifluoroacetyl)pyridin-2-yl}amino)piperidine-1-carboxylate

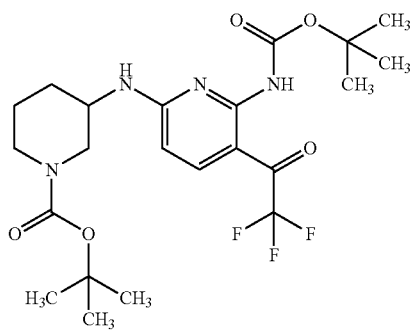 [SMILES: CC(C)(C)OC(=O)Nc1nc(NC2CCCN(C(=O)OC(C)(C)C)C2)ccc1C(=O)C(F)(F)F]

561 mg (2.8 mmol) of tert-butyl 3-aminopiperidine-1-carboxylate, 700 mg (2.16 mmol) of tert-butyl-[6-chloro-3-(trifluoroacetyl)pyridin-2-yl]carbamate (Example 11A) and 0.56 ml (3.23 mmol) of diisopropylethylamine were suspended in 14 ml of DMSO and heated in a microwave reactor at 90° C. for 45 min. The reaction mixture was diluted with ethyl acetate (100 ml) and washed with saturated aqueous ammonium chloride solution (3×40 ml) and then with saturated aqueous sodium bicarbonate solution (40 ml), and the organic phase was dried over magnesium sulfate, diluted and concentrated. The residue was chromatographed on silica gel (mobile phase: cyclohexane-ethyl acetate 5:1 to 1:1). This gave 670 mg (63% of theory) of the product.

LCMS (Method 6): $R_t$=2.70 min. (m/z=489 (M+H)$^+$)

Example 22A

1-[2-Amino-6-(piperidin-3-ylamino)pyridin-3-yl]-2,2,2-trifluoroethanone hydrochloride

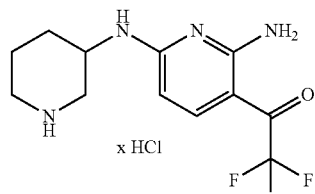

670 mg (1.37 mmol) of tert-butyl 3-({6-[(tert-butoxycarbonyl)amino]-5-(trifluoroacetyl)pyridin-2-yl}amino)piperidine-1-carboxylate (Example 21A) were dissolved in 25 ml of a solution of hydrochloric acid in dioxane (4 M), and the mixture was stirred at RT for 20 h. After the reaction had gone to completion, the reaction mixture was diluted with diethyl ether (100 ml), and the precipitate was filtered off and washed with diethyl ether (100 ml) and dried. This gave 286 mg (64% of theory) of the product as a solid.

LCMS (Method 6): $R_t$=0.81 min. (m/z=289 (M+H)$^1$)

$^1$H-NMR (400 MHz, DMSO-d$_6$): δ=9.26 (br s, 1H), 9.07 (br s, 1H), 8.8.34 (br s, 1H), 7.59 (d, 1H), 6.22 (br, 2H), 6.03 (d, 1H), 4.25 (br m, 1H), 3.36 (m, 1H), 3.13 (m, 1H), 2.93 (m, 2H), 2.00-1.85 (m, 2H), 1.73 (m, 1H), 1.56 (m, 1H).

Example 23A tert-Butyl(6-chloro-3-propanoylpyridin-2-yl)carbamate

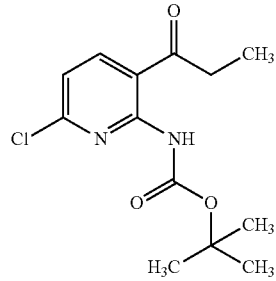 [SMILES: CCC(=O)c1ccc(Cl)nc1NC(=O)OC(C)(C)C]

Under argon, 7.00 g (30.6 mmol) of tert-butyl(6-chloropyridin-2-yl)carbamate (Example 3A) were initially charged in 90 ml of THF and cooled to −50° C. 47.8 ml (76.5 mmol) of butyllithium (1.6 M in hexane) were added dropwise. After the dropwise addition had ended, the reaction was slowly warmed to 0° C. and kept at 0° C. for 1 h. The mixture was then cooled again to −40° C., and 9.85 g (61.2 mmol) of N-propionylmorpholine dissolved in 10 ml of THF were added. The reaction solution was stirred at −40° C. for another 1 h and then, at −40° C., poured into 1 l of ethyl acetate and 350 ml of ammonium chloride solution, and the organic phase was separated off and washed with water and saturated aqueous sodium bicarbonate solution. The organic phase was dried over magnesium sulfate and concentrated on a rotary evaporator. The crude product was chromatographed on silica gel (mobile phase cyclohexane/ethyl acetate 10:1 to 1:1). This gave 2800 mg (32% of theory) of the product.

LCMS (Method 6): $R_t$=2.13 min. (m/z=283 (M–H)$^-$)
$^1$H-NMR (400 MHz, DMSO-$d_6$): δ=10.53 (br s, 1H), 8.19 (d, 1H), 7.31 (d, 1H), 2.94 (q, 2H), 1.45 (s, 9H), 1.06 (t, 3H).

Example 24A tert-Butyl[6-({2-[(tert-butoxycarbonyl)amino]ethyl}amino)-3-propanoylpyridin-2-yl]carbamate

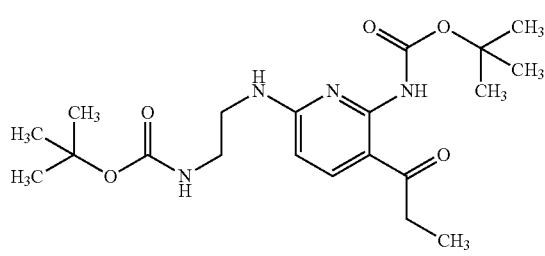 [SMILES: CCC(=O)c1ccc(NCCNC(=O)OC(C)(C)C)nc1NC(=O)OC(C)(C)C]

730 mg (2.4 mmol) of tert-butyl(6-chloro-3-propanoylpyridin-2-yl)carbamate (Example 23A) were initially charged in 7 ml of DMSO, and 512 mg (3.2 mmol) of N-Boc-ethylenediamine and 640 µl (3.7 mmol) of N,N-diisopropylethylamine were added. The reaction mixture was irradiated in the microwave reactor at 90° C. for 45 min. The reaction mixture was taken up in a mixture of ethyl acetate and water. The organic phase was washed with saturated aqueous ammonium chloride solution and then with saturated aqueous sodium bicarbonate solution, dried over magnesium sulfate and concentrated on a rotary evaporator. The reaction mixture was chromatographed on silica gel (mobile phase cyclohexane/ethyl acetate 5:1→1:1). This gave 530 mg (53% of theory) of the product as a solid.

LCMS (Method 6): $R_t$=2.19 min. (m/z=409 (M+H)$^+$).
$^1$H-NMR (400 MHz, DMSO-$d_6$): δ=11.47 (s, 1H), 7.93 (br m, 1H), 7.64 (br m, 1H), 6.82 (br s, 1H), 6.15 (d, 1H), 3.43 (br m, 2H), 3.14 (m, 2H), 2.83 (q, 2H), 2.56 (br s, 4H), 1.47 (s, 9H), 1.32 (s, 9H), 1.03 (t, 3H).

Example 25A

1-{2-Amino-6-[(2-aminoethyl)amino]pyridin-3-yl}propan-1-one hydrochloride

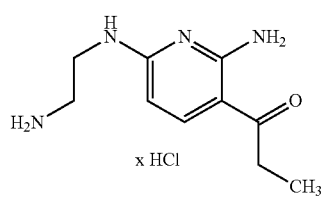

530 mg (1.30 mmol) of tert-butyl[6-({2-[(tert-butoxycarbonyl)amino]ethyl}amino)-3-propanoylpyridin-2-yl]carbamate (Example 24A) were dissolved in 15 ml of a solution of hydrochloric acid in dioxane (4 M), and the mixture was stirred at RT for 20 h. After the reaction had gone to completion, the reaction mixture was diluted with diethyl ether (100 ml), and the precipitate was filtered off, washed with diethyl ether (100 ml) and dried. This gave 290 mg (91% of theory) of the product as a solid.

LCMS (Method 6): $R_t$=1.15 min. (m/z=309 (M+H)$^+$)

Example 26A tert-Butyl 3-({6-[(tert-butoxycarbonyl)amino]-5-propanoylpyridin-2-yl}amino)piperidine-1-carboxylate

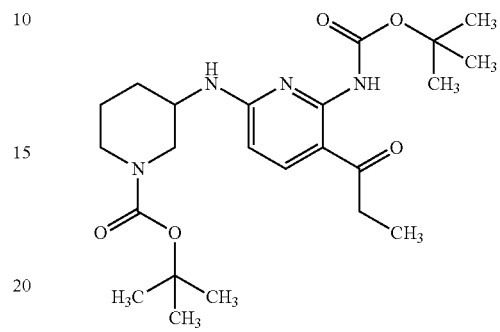

610 mg (3.0 mmol) of tert-butyl 3-aminopiperidine-1-carboxylate, 700 mg (2.3 mmol) of tert-butyl(6-chloro-3-propanoylpyridin-2-yl)carbamate (Example 23A) and 610 µl (3.5 mmol) of diisopropylethylamine were suspended in 7 ml of DMSO and heated in a microwave reactor at 90° C. for 45 min. The reaction mixture was diluted with ethyl acetate (100 ml) and washed with saturated aqueous ammonium chloride solution (3×40 ml), then with saturated aqueous sodium bicarbonate solution (40 ml), and the organic phase was dried over magnesium sulfate, diluted and concentrated. The residue was chromatographed on silica gel (mobile phase: cyclohexane-ethyl acetate 5:1 to 1:1). This gave 380 mg (35% of theory) of the product.

LCMS (Method 6): $R_t$=2.42 min. (m/z=449 (M+H)$^+$)

Example 27A

1-[2-Amino-6-(piperidin-3-ylamino)pyridin-3-yl]propan-1-one hydrochloride

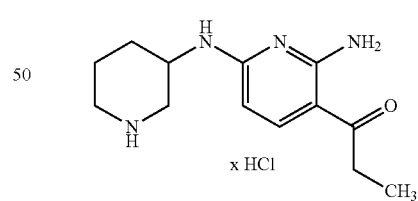

380 mg (0.85 mmol) of tert-butyl 3-({6-[(tert-butoxycarbonyl)amino]-5-propanoylpyridin-2-yl}amino)piperidine-1-carboxylate (Example 26A) were dissolved in 10 ml of a solution of hydrochloric acid in dioxane (4 M), and the mixture was stirred at RT for 20 h. After the reaction had gone to completion, the reaction mixture was diluted with diethyl ether (100 ml), and the recipitate was filtered off and washed with diethyl ether (100 ml) and dried. This gave 170 mg (70% of theory) of the product as a solid.

LCMS (Method 9): $R_t$=0.95 min. (m/z=249 (M+H)$^+$)

Example 28A tert-Butyl 3-[(6-amino-5-nitropyridin-2-yl)amino]piperidine-1-carboxylate

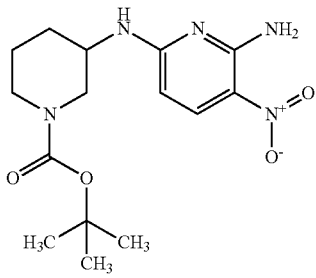 [SMILES: CC(C)(C)OC(=O)N1CCCC(Nc2ccc([N+](=O)[O-])c(N)n2)C1]

500 mg (2.11 mmol) of tert-butyl 3-aminopiperidine-1-carboxylate, 772 mg (4.22 mmol) of 2-amino-6-chloro-3-nitropyridine and 1.05 ml (6.34 mmol) of diisopropylethylamine were suspended in 18 ml of DMSO and heated in a microwave reactor at 120° C. for 45 min. The reaction mixture was purified by preparative RP-HPLC (Method 11). This gave 600 mg (81% of theory) of the product as a solid.

LCMS (Method 6): $R_t$=1.77 min. (m/z=338 (M+H)$^+$)

Example 29A

3-Nitro-$N^6$-(piperidin-3-yl)pyridine-2,6-diamine hydrochloride

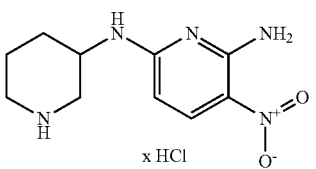 [SMILES: Nc1nc(NC2CCCNC2)ccc1[N+](=O)[O-]]

610 mg (1.62 mmol) of tert-butyl 3-[(6-amino-5-nitropyridin-2-yl)amino]piperidine-1-carboxylate (Example 28A) were dissolved in 40 ml of a solution of hydrochloric acid in dioxane (4 M), and the mixture was stirred at RT for 30 min. After the reaction had gone to completion, the solvent was removed completely. This gave 662 mg of the crude product.

LCMS (Method 4): $R_t$=0.86 min. (m/z=238 (M+H)$^+$)

Example 30A

3-Amino-3-(2,4-dichlorophenyl)acrylonitrile

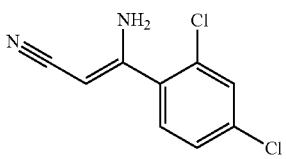 [SMILES: N#C/C=C(\N)c1ccc(Cl)cc1Cl]

Under argon, 90 g (889.46 mmol) of diisopropylamine were initially charged in 1660 ml of THF at −70° C. in a three-necked flask with mechanical stirrer. 124.66 ml of N-butyllithium solution (2.5 M in hexane, 758.66 mmol) were added dropwise at such a rate that the temperature did not exceed −60° C. The mixture was stirred for 10 min, and a solution of 32.22 g (784.82 mmol) of acetonitrile in 340 ml of THF was then slowly added dropwise and the suspension was stirred for 30 min. A solution of 90 g (523.21 mmol) of 2,4-dichlorobenzonitrile in 340 ml of THF was then added dropwise, and the mixture was stirred at −70° C. for 20 min. The mixture was allowed to slowly warm to RT and stirred at RT for a further 16 h. 600 ml of water were added, most of the THF was distilled off and water and dichloromethane were added. The organic phase was washed with saturated aqueous sodium chloride solution. Removal of the solvent gave crystals which were purified by trituration with diethyl ether. This gave 76.5 g (69% of theory) of the product as a solid.

LCMS (Method 5): $R_t$=3.07 min. (m/z=213 (M+H)$^+$)

$^1$H-NMR (400 MHz, DMSO-$d_6$): δ=7.70 (d, 1H), 7.47 (dd, 1H), 7.40 (d, 1H), 7.02 (s, broad, 2H), 3.79 (s, 1H).

Example 31A (2Z)-3-Amino-3-[4-(trifluoromethyl)phenyl]prop-2-enonitrile

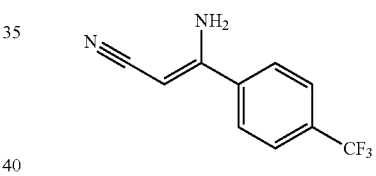

Under argon, 28.1 g (278 mmol) of diisopropylamine were initially charged in 450 ml of THF at −70° C. in a three-necked flask with mechanical stirrer. 148 ml of N-butyllithium solution (1.6 M in hexane, 237 mmol) were added dropwise at such a rate that the temperature did not exceed −60° C. The mixture was stirred for 10 min, and a solution of 12.9 ml (245 mmol) of acetonitrile in 100 ml of THF was then slowly added dropwise and the suspension was stirred for 30 min. A solution of 28 g (164 mmol) of 4-(trifluoromethyl)benzonitrile in 100 ml of THF was added dropwise, and the mixture was stirred at −70° C. for 20 min. The mixture was allowed to slowly warm to RT and stirred at RT for a further 16 h. 150 ml of water were added, most of the THF was distilled off and water and dichloromethane were added. The organic phase was washed with saturated aqueous sodium chloride solution. Removal of the solvent gave crystals which were purified by trituration with diisopropyl ether (once with 40 ml, twice with 20 ml). The crystals were filtered off, washed with petroleum ether and dried. This gave 27 g (78% of theory) of the product as a solid.

LCMS (Method 9): $R_t$=2.05 min. (m/z=213 (M+H)$^+$)

$^1$H-NMR (400 MHz, DMSO-$d_6$): δ=7.79 (s, 4H), 7.98 (br s, 1H), 4.30 (s, 1H).

Example 32A

Ethyl[2-cyano-1-(2,4-dichlorophenyl)ethenyl]carbamate

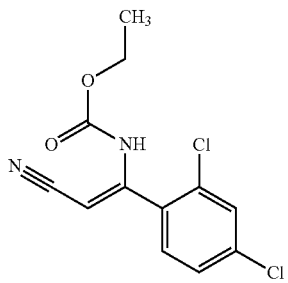 [SMILES: CCOC(=O)N/C(=C\C#N)c1ccc(Cl)cc1Cl]

4.85 g (211 mmol) of sodium were dissolved in ethanol (260 ml), 30.0 g (141 mmol) of 3-amino-3-(2,4-dichlorophenyl)acrylonitrile and 36.59 g (310 mmol) of diethyl carbonate were added and the reaction solution was stirred under reflux for 4 h. Ethyl acetate and water were added to the reaction mixture, and the pH was adjusted to pH=5 with concentrated hydrochloric acid. The organic phase was separated off, dried over magnesium sulfate and concentrated on a rotary evaporator. The residue was chromatographed on silica gel (mobile phase cyclohexane/ethyl acetate 7:1 to 1:1), the product had an $R_f$=0.5 in cyclohexane/ethyl acetate 1:1. This gave 17.1 g (43% of theory) of the product.

LCMS (Method 6): $R_t$=1.87 min. (m/z=285 (M+H)$^+$)

$^1$H-NMR (400 MHz, DMSO-d$_6$): δ=10.35 (s, 1H), 7.79 (d, 1H), 7.54 (m, 2H), 6.16 (s, 1H), 4.13 (q, 2H), 1.22 (t, 3H).

Example 33A

Ethyl{2-cyano-1-[4-(trifluoromethyl)phenyl]ethenyl}carbamate

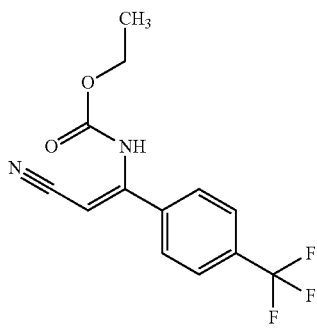 [SMILES: CCOC(=O)N/C(=C\C#N)c1ccc(C(F)(F)F)cc1]

4.88 g (212 mmol) of sodium were dissolved in ethanol (260 ml), 30.0 g (141 mmol) of 3-amino-3-(2,4-dichlorophenyl)acrylonitrile and 36.75 g (311 mmol) of diethyl carbonate were added and the reaction solution was stirred under reflux for 5 h. Ethyl acetate and water were added to the reaction mixture, and the pH was adjusted to pH=5 with 2M hydrochloric acid. The organic phase was separated off, dried over magnesium sulfate and concentrated on a rotary evaporator. The residue was chromatographed on silica gel (mobile phase cyclohexane/ethyl acetate 9:1 to 2:1). This gave 13.3 g (33% of theory) of the product as a mixture of E and Z isomers.

LCMS (Method 6): $R_t$=1.92 min. (m/z=285 (M+H)$^+$)

Example 34A (2Z)-3-Amino-3-(2-chloro-4-fluorophenyl)prop-2-enonitrile

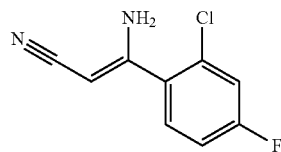 [SMILES: N#C/C=C(\N)c1ccc(F)cc1Cl]

Under argon, 35.3 g (273 mmol) of diisopropylamine were initially charged in 450 ml of THF at −70° C. in a three-necked flask with mechanical stirrer. 145 ml of N-butyl-lithium solution (1.6 M in hexane, 237 mmol) were added dropwise at such a rate that the temperature did not exceed −60° C. The mixture was stirred for 30 min, and a solution of 12.7 ml (241 mmol) of acetonitrile in 100 ml of THF was then slowly added dropwise and the suspension was stirred for 30 min. A solution of 25 g (160.7 mmol) of 2-chloro-4-fluorobenzonitrile in 100 ml of THF was added dropwise, and the mixture was stirred at −70° C. for 20 min. The mixture was allowed to slowly warm to RT and stirred at RT for a further 16 h. 150 ml of water were added, most of the THF was distilled off and water and dichloromethane were added. The organic phase was washed with saturated aqueous sodium chloride solution. Removal of the solvent gave an oil. A solid could be obtained by trituration with diisopropylether and subsequent filtration with suction. Drying under high vacuum gave 12.58 g (36% of theory) of the product. This was a mixture of E and Z isomers which was used without further purification.

LCMS (Method 8): $R_t$ (isomer 1)=0.83 min. (m/z=197 (M+H)$^+$); $R_t$ (isomer 2)=1.02 min. (m/z=197 (M+H)$^+$)

$^1$H-NMR (400 MHz, DMSO-d$_6$): δ=7.52 (dd, 1H), 7.44 (dd, 1H), 7.26 (m, 1H), 6.99 (s, br, 2H), 3.77 (s, 1H).

Example 35A (2Z)-3-Amino-3-(2,4-difluorophenyl)prop-2-enonitrile

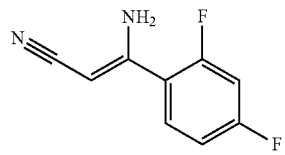

Under argon, 13.3 g (132 mmol) of diisopropylamine were initially charged in 350 ml of THF at −70° C. in a three-necked flask with mechanical stirrer. 70.5 ml of N-butyl-lithium solution (1.6 M in hexane, 112.8 mmol) were added dropwise at such a rate that the temperature did not exceed −60° C. The mixture was stirred for 10 min, and a solution of 6.14 ml (116.7 mmol) of acetonitrile in 37 ml of THF was then slowly added dropwise and the suspension was stirred for 30 min. A solution of 11.04 g (77.8 mmol) of 2,4-difluorobenzonitrile in 73 ml of THF was added dropwise, and the mixture was stirred at −70° C. for 90 min. The mixture was allowed to warm to RT. 470 ml of water were added, most of the THF was distilled off and water and ethyl acetate were added. The organic phase was washed twice with in each case 150 ml of water and then with 110 ml of saturated aqueous sodium chloride solution. Drying of the organic phase with sodium sulfate and removal of the solvent gave a solid. The product could be obtained by trituration with diisopropyl ether and subsequent filtration with suction. Drying under high vacuum gave 7.24 g (51% of theory) of the product. This was a mixture of E and Z isomers that was used without further purification.

LCMS (Method 6): $R_t$ (isomer 1)=1.14 min. (m/z=181 (M+H)$^-$); $R_t$ (isomer 2)=1.45 min. (m/z=181 (M+H)$^+$)

$^1$H-NMR (400 MHz, DMSO-$d_6$): δ=7.48-7.56 (m, 1H), 7.31-7.39 (m, 1H), 7.15 (dt, 1H), 6.94 (s, br, 2H), 3.95 (s, 1H).

Example 36A

Ethyl[(Z)-1-(2-chloro-4-fluorophenyl)-2-cyanoethenyl]carbamate

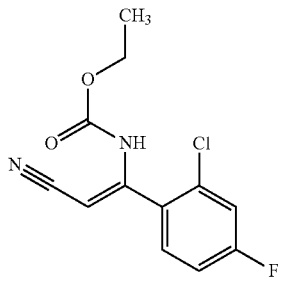 [SMILES: CCOC(=O)N/C(=C\C#N)c1ccc(F)cc1Cl]

At 40° C., 982 mg (42.7 mmol) of sodium were dissolved in ethanol (53 ml). 5.6 g (28.5 mmol) of 3-amino-3-(2-chlor-4-fluorophenyl)prop-2-enonitrile and 7.4 g (62.7 mmol) of diethyl carbonate were added, and the reaction solution was stirred under reflux for 4 h. 200 ml of ethyl acetate and 150 ml of water were added to the reaction mixture, and the pH was adjusted to pH=5 with hydrochloric acid. The organic phase was separated off, dried over magnesium sulfate and concentrated on a rotary evaporator. Removal of the solvent gave 6.77 g (88% of theory) of the product as a mixture of E and Z isomers.

LCMS (Method 8): $R_t$ (isomer 1)=0.99 min. (m/z=269 (M+H)$^+$); $R_t$ (isomer 2)=1.10 min. (m/z=269 (M+H)$^+$)

Example 37A

Ethyl[(Z)-2-cyano-1-(2,4-difluorophenyl)ethenyl]carbamate

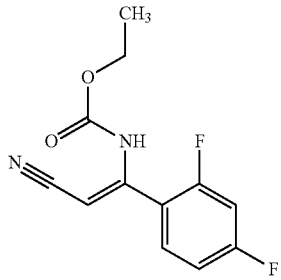 [SMILES: CCOC(=O)N/C(=C\C#N)c1ccc(F)cc1F]

At 40° C., 769 mg (33.44 mmol) of sodium were dissolved in ethanol (41 ml). 4.14 g (22.29 mmol) of 3-amino-3-(2,4-difluorophenyl)prop-2-enonitrile and 5.79 g (49 mmol) of diethyl carbonate were added, and the reaction solution was stirred under reflux for 4 h. 200 ml of ethyl acetate and 150 ml of water were added to the reaction mixture and the pH was adjusted with hydrochloric acid to pH=5. The organic phase was separated off, dried over magnesium sulfate and concentrated on a rotary evaporator. The residue was triturated with diisopropyl ether and the white precipitate was filtered off with suction. More product was obtained by separating the mother liquor by preparative HPLC (Method 11). Drying under high vacuum gave a total of 4.92 g (49% of theory) of the product as a mixture of E and Z isomers which was used without further purification.

LCMS (Method 9): $R_t$ (isomer 1)=1.66 min. (m/z=253 (M+H)$^+$); $R_t$ (isomer 2)=1.87 min. (m/z=253 (M+H)$^+$)

Example 38A 1-(Propan-2-yl)piperidine-4-carbohydrazide

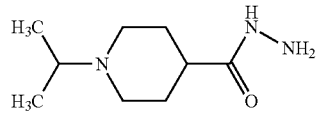

3.60 g (18.1 mmol) of ethyl 1-(1-methylethyl)piperidin-4-carboxylate and 1.00 g (19.9 mmol) of hydrazine hydrate were initially charged in 15 ml of ethanol and stirred at reflux for 16 h. The reaction mixture was cooled to RT and concentrated, and the residue was lyophilized. The crude product was triturated with diethyl ether (25 ml), filtered off and dried. This gave 1.91 g (57% of theory) of the product.

GC/MS (Method 10): $R_t$=5.68 min. (m/z=185 (M$^+$)

$^1$H-NMR (400 MHz, DMSO-$d_6$): δ=8.90 (s, 1H), 4.15 (br, 2H), 2.76 (br d, 2H), 2.64 (quintett, 1H), 2.06-1.95 (m, 3H), 1.63-1.47 (m, 4H), 0.94 (d, 6H).

Example 39A 7-(2,4-Dichlorophenyl)-2-[1-(1-methylethyl)piperidin-4-yl][1,2,4]triazolo[1,5-c]pyrimidin-5(6H)-one

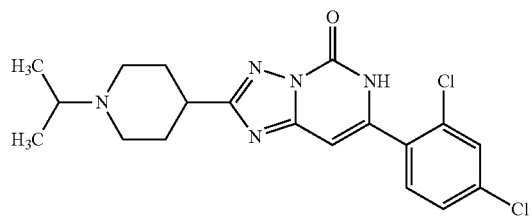 [SMILES: CC(C)N1CCC(c2nc3cc(-c4ccc(Cl)cc4Cl)[nH]c(=O)n3n2)CC1]

In a round-bottom flask fitted with reflux condenser and a drying tube filled with calcium chloride, 500 mg (1.70 mmol) of ethyl[2-cyano-1-(2,4-dichlorophenyl)ethenyl]carbamate and 310 mg (1.70 mmol) of 1-(1-methylethyl)piperidin-4-carbohydrazide (Example 38A) were dissolved in 2 ml of 1-methyl-2-pyrrolidone, and the reaction mixture was stirred at 160° C. for 3 h. The reaction solution was cooled to 100° C., water (20 ml) was added and the mixture was then cooled to RT and stirred for 15 min. The reaction mixture was extracted with dichloromethane (3×50 ml), and the combined organic phases were dried over magnesium sulfate and concentrated. The crude product was chromatographed on basic aluminum oxide (mobile phase dichloromethane/methanol 10:1, then dichloromethane/methanol/17% strength aqueous ammonia solution 15:2:0.2). This gave 2.55 g (78% of theory) of the product.

LCMS (Method 8): $R_t$=0.75 min. (m/z=406 (M+H)$^+$)

$^1$H-NMR (400 MHz, DMSO-d$_6$): δ=12.38 (s, 1H), 10.42 (br s, 1H), 7.86 (s, 1H), 7.63 (s, 2H), 7.66 (d, 1H) 6.86 (s, 1H), 3.46 (m, 3H), 3.22-3.07 (m, 3H), 2.24 (m, 4H), 1.32 (d, 6H).

Example 40A

5-Chloro-7-(2,4-dichlorophenyl)-2-[1-(propan-2-yl)piperidin-4-yl][1,2,4]triazolo[1,5-c]pyrimidine

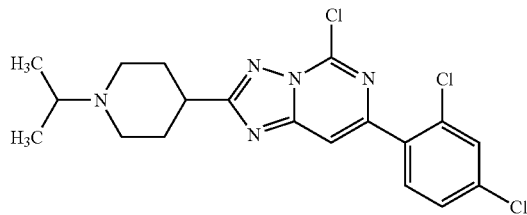 [SMILES: CC(C)N1CCC(c2nc3cc(-c4ccc(Cl)cc4Cl)nc(Cl)n3n2)CC1]

530 mg (1.30 mmol) of 7-(2,4-dichlorophenyl)-2-[1-(1-methylethyl)piperidin-4-yl][1,2,4]-triazolo[1,5-c]pyrimidin-5(6H)-one were initially charged in phosphorus oxychloride (16 ml), and 1.19 g (5.22 mmol) of benzyltriethylammonium chloride were added. The mixture was then stirred at 120° C. for 2.5 h. The reaction mixture was poured onto saturated aqueous sodium bicarbonate solution (150 ml), and solid sodium bicarbonate was added until a pH of 7 had been reached. The mixture was extracted with dichloromethane (3×50 ml), and the combined organic phases were washed with water (50 ml), dried over magnesium sulfate and concentrated. This gave 502 mg (89% of theory) of the product as a solid.

LCMS (Method 6): $R_t$=1.26 min. (m/z=424 (M+H)$^+$)

$^1$H-NMR (400 MHz, DMSO-d$_6$): δ=9.29 (br s, 1H), 8.22 (s, 1H), 7.85 (d, 1H), 7.73 (d, 1H), 7.65 (dd, 1H), 3.52 (m, 3H), 3.49 (m, 1H), 3.20 (m, 2H), 2.34 (m, 2H), 2.14 (m, 2H), 1.31 (d, 6H).

Example 41A tert-Butyl 4-(hydrazinylcarbonyl)piperidine-1-carboxylate

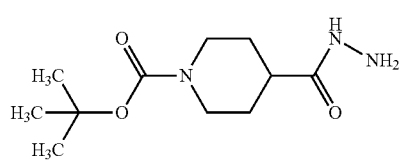

10.0 g (38.9 mmol) of 1-tert-butyl 4-ethyl piperidine-1,4-dicarboxylate were initially charged in 35 ml of ethanol, and 3.8 ml (3.90 g, 78 mmol) of hydrazine hydrate were added with stirring. The mixture was stirred at reflux for 9 h. The reaction mixture was cooled to RT, 1.9 ml (39 mmol) of hydrazine hydrate were added and the reaction solution was stirred at reflux for another 24 h. The solvent was concentrated, ethanol (50 ml) was added and the mixture was concentrated again. Diethyl ether (150 ml) was added, and the mixture was stirred in an ultrasonic bath for 5 min. The product was filtered off and dried. This gave 9.20 g (97% of theory) of the product.

LCMS (Method 6): $R_t$=0.95 min. (m/z=244 (M+H)$^+$)

$^1$H-NMR (400 MHz, DMSO-d$_6$): δ=8.99 (s, 1H), 4.17 (br, 2H), 3.95 (br d, 2H), 2.71 (br, 2H), 2.23 (m, 1H), 1.60 (m, 2H), 1.40 (m, 11H).

Example 42A tert-Butyl 4-[7-(2,4-dichlorophenyl)-5-oxo-5,6-dihydro[1,2,4]triazolo[1,5-c]pyrimidin-2-yl]-piperidine-1-carboxylate

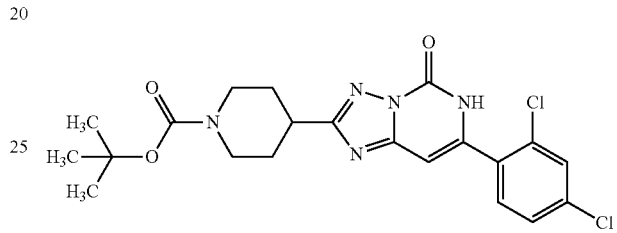

In a round-bottom flask fitted with reflux condenser and a drying tube filled with calcium chloride, 5.86 g (20.6 mmol) of ethyl[2-cyano-1-(2,4-dichlorophenyl)ethenyl]carbamate and 5.00 g (20.6 mmol) of tert-butyl 4-(hydrazinylcarbonyl)piperidine-1-carboxylate were dissolved in 11 ml of 1-methyl-2-pyrrolidone, and the reaction mixture was stirred at 150° C. for 3 h. The reaction solution was cooled to RT, water (150 ml) was added and the mixture was stirred in an ultrasonic bath for another 2 min. The solid was filtered off with suction and dried under high vacuum. This gave 7.23 g (76% of theory) of the product.

LCMS (Method 3): $R_t$=2.36 min. (m/z=464 (M+H)$^+$)

$^1$H-NMR (400 MHz, DMSO-d$_6$): δ=12.35 (br s, 1H), 7.84 (s, 1H), 7.61 (s, 2H), 6.82 (s, 1H), 4.96 (m, 2H), 3.05 (m, 1H), 2.96 (m, 2H), 1.98 (m, 2H), 1.64 (m, 2H), 1.43 (s, 9H).

Example 43A 7-(2,4-Dichlorophenyl)-2-(piperidin-4-yl)[1,2,4]triazolo[1,5-c]pyrimidin-5(6H)-one hydrochloride

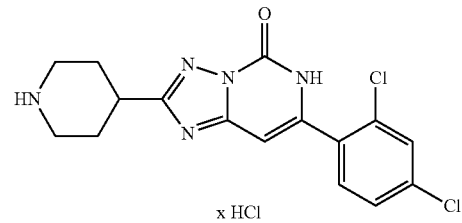 [SMILES: O=c1[nH]c(-c2ccc(Cl)cc2Cl)cc2nc(C3CCNCC3)nn12]

8.47 g (18.2 mmol) of tert-butyl 4-[7-(2,4-dichlorophenyl)-5-oxo-5,6-dihydro[1,2,4]triazolo[1,5-c]-pyrimidin-2-yl]piperidine-1-carboxylate (Example 42A) and hydrogen chloride in dioxane (4M, 90 ml) were stirred at RT for 3 h, the solvent was then concentrated to half of its original volume, diethyl ether (50 ml) was added and the reaction mixture was stirred for another 2 min. The solid was filtered off and dried. This gave 7.22 g (99% of theory) of the product.

LCMS (Method 6): $R_t$=0.80 min. (m/z=364 (M+H)$^+$)

Example 44A 2-(1-Cyclopropylpiperidin-4-yl)-7-(2,4-dichlorophenyl)[1,2,4]triazolo[1,5-c]pyrimidin-5(6H)-one

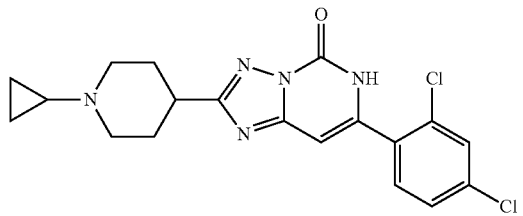 [SMILES: O=c1[nH]c(-c2ccc(Cl)cc2Cl)cc2nc(C3CCN(C4CC4)CC3)nn12]

1.00 g (2.50 mmol) of 7-(2,4-dichlorophenyl)-2-(piperidin-4-yl)[1,2,4]triazolo[1,5-c]pyrimidin-5(6H)-one hydrochloride and 3 Å molecular sieve (1 g) were initially charged in 15 ml of dry methanol and acetic acid (1.43 ml, 25 mmol) of 3.01 ml (2.61 g, 15 mmol) of [(1-ethoxy-1-cyclopropyl)oxy]-trimethylsilane and 690 mg (11 mmol) of sodium cyanoborohydride were then added. The mixture was stirred at reflux overnight. The mixture was cooled to RT and the reaction mixture was filtered. 50 ml of dichloromethane and 50 ml of water were added to the filtrate, and the mixture was extracted. The organic phase was dried over magnesium sulfate and concentrated on a rotary evaporator. This gave 540 mg (53% of theory) of the product.

LCMS (Method 6): $R_t$=0.87 min. (m/z=404 (M+H)$^+$)

$^1$H-NMR (400 MHz, DMSO-d$_6$): δ=12.0 (br, 1H), 7.85 (s, 1H), 7.63 (s, 3H), 6.86 (s, 1H), 6.66 (s, 1H), 3.37 (m, 3H), 3.10 (m, 2H), 2.18 (m, 2H), 2.03 (m, 1H), 1.91 (m, 1H), 0.86 (m, 1H), 0.76 (m, 2H), 0.69 (m, 2H).

Example 45A

5-Chloro-2-(1-cyclopropylpiperidin-4-yl)-7-(2,4-dichlorophenyl)[1,2,4]triazolo[1,5-c]pyrimidine

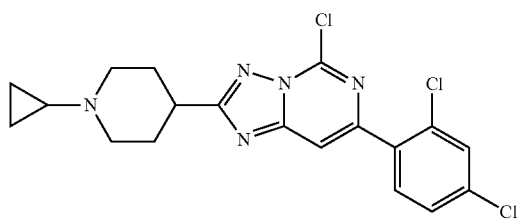 [SMILES: Clc1ccc(-c2cc3nc(C4CCN(C5CC5)CC4)nn3c(Cl)n2)c(Cl)c1]

450 mg (1.11 mmol) of 2-(1-cyclopropylpiperidin-4-yl)-7-(2,4-dichlorophenyl)[1,2,4]triazolo[1,5-c]pyrimidin-5(6H)-one (Example 44A) were initially charged in phosphorus oxychloride (10 ml), 1.01 g (4.45 mmol) of benzyltriethylammonium chloride were added and the mixture was then stirred at 120° C. for 2.5 h. The reaction mixture was poured into saturated aqueous sodium bicarbonate solution (150 ml), and solid sodium bicarbonate was added until a pH of 7 had been reached. The mixture was extracted with dichloromethane (3×50 ml), and the combined organic phases were washed with water (50 ml), dried over magnesium sulfate and concentrated. The reaction mixture was taken up in acetonitrile and purified by preparative HPLC (Method 11). Lyophilization gave 238 mg (50% of theory) of the product.

LCMS (Method 8): $R_t$=1.00 min. (m/z=422 (M+H)$^+$)

$^1$H-NMR (400 MHz, DMSO-d$_6$): δ=10.05 (br, 1H), 8.21 (s, 1H), 7.86 (d, 1H), 7.73 (d, 1H), 7.65 (dd, 1H), 3.64 (m, 2H), 2.83 (m, 1H), 2.33 (m, 2H), 2.17 (m, 2H), 1.12 (m, 2H), 0.84 (m, 2H). 3H are hidden under the signal of water.

Example 46A

2-[1-(Cyclopropylmethyl)piperidin-4-yl]-7-(2,4-dichlorophenyl)[1,2,4]triazolo[1,5-c]pyrimidin-5(6H)-one hydrochloride

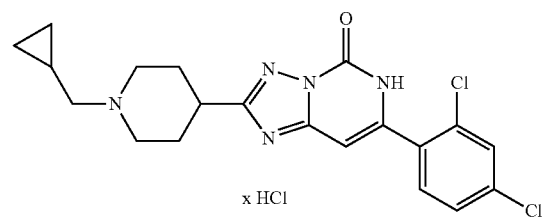 [SMILES: O=c1[nH]c(-c2ccc(Cl)cc2Cl)cc2nc(C3CCN(CC4CC4)CC3)nn12]

1.00 g (2.50 mmol) of 7-(2,4-dichlorophenyl)-2-(piperidin-4-yl)[1,2,4]triazolo[1,5-c]pyrimidin-5(6H)-one hydrochloride were initially charged in DMF (6 ml), and 268 μl (2.75 mmol) of 1-bromomethylcyclopropane and 759 mg (5.49 mmol) of potassium carbonate were added. The reaction mixture was stirred at 80° C. for 16 h, the solution was then filtered and ethyl acetate (100 ml) and water (75 ml) were added. The phases were separated and the aqueous phase was extracted with ethyl acetate (two times 15 ml). The combined organic phases were washed with saturated aqueous sodium chloride solution, dried (magnesium sulfate) and concentrated. The product was taken up in acetonitrile and purified by preparative RP-HPLC (Method 11). This gave 413 mg (39% of theory) of the product.

LCMS (Method 9): $R_t$=1.25 min. (m/z=364 (M−HCl+H)$^+$)

Example 47A

5-Chloro-2-[1-(cyclopropylmethyl)piperidin-4-yl]-7-(2,4-dichlorophenyl)[1,2,4]triazolo[1,5-c]-pyrimidine

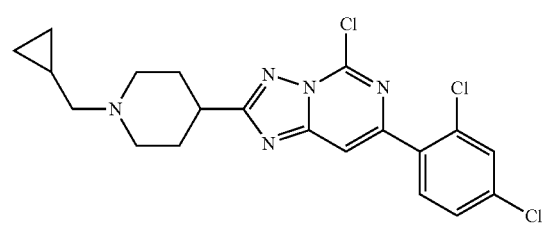 [SMILES: Clc1ccc(-c2cc3nc(C4CCN(CC5CC5)CC4)nn3c(Cl)n2)c(Cl)c1]

356 mg (0.85 mmol) of 2-[1-(cyclopropylmethyl)piperidin-4-yl]-7-(2,4-dichlorophenyl)[1,2,4]-triazolo[1,5-c]pyrimidin-5(6H)-one hydrochloride (Example 46A) were initially charged in phosphorus oxychloride (6 ml), 775 mg (3.40 mmol) of benzyltriethylammonium chloride were added and the mixture was stirred at 120° C. for 2.5 h. The reaction mixture was poured into saturated aqueous sodium bicarbonate solution (150 ml), and solid sodium bicarbonate was added until a pH of 7 had been reached. The mixture was extracted with dichloromethane (3×50 ml), and the combined organic phases were washed with water (50 ml), dried over magnesium sulfate and concentrated. This gave 307 mg (83% of theory) of the product as a solid.

LCMS (Method 6): $R_t$=1.30 min. (m/z=436 (M+H)$^+$)

$^1$H-NMR (400 MHz, DMSO-$d_6$): δ=8.18 (s, 1H), 7.85 (d, 1H), 7.72 (d, 1H), 7.64 (dd, 1H), 3.47 (m, 1H), 3.06 (m, 2H), 2.355-2.0 (m, 6H), 0.87 (m, 2H), 0.49 (m, 2H), 0.40 (m, 1H), 0.13 (m, 2H).

Example 48A 7-(2,4-Dichlorophenyl)-2-(1-methylpiperidin-4-yl)[1,2,4]triazolo[1,5-c]pyrimidin-5(6H)-one

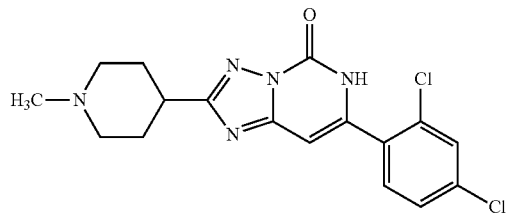 [SMILES: CN1CCC(c2nc3cc(-c4ccc(Cl)cc4Cl)[nH]c(=O)n3n2)CC1]

At 0° C., 500 mg (1.25 mmol) of 7-(2,4-dichlorophenyl)-2-(piperidin-4-yl)[1,2,4]triazolo[1,5-c]pyrimidin-5(6H)-one hydrochloride were initially charged in methanol (4 ml), and 3 Å molecular sieve (50 mg), formalin (210 μl, 7.50 mmol) and sodium cyanoborhydride (470 mg, 7.50 mmol) were added. The mixture was stirred at 0° C. for 1 h and then stirred at RT for another 12 h. The reaction mixture was filtered, and dichloromethane (100 ml) and water (75 ml) were added to the filtrate. The mixture was extracted and the organic phase was dried (magnesium sulfate) and concentrated. This gave 274 mg (58% of theory) of the crude product.

LCMS (Method 8): $R_t$=0.74 min. (m/z=378 (M+H)$^+$)

Example 49A

5-Chloro-7-(2,4-dichlorophenyl)-2-(1-methylpiperidin-4-yl)[1,2,4]triazolo[1,5-c]pyrimidine

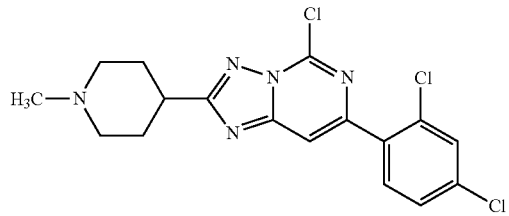 [SMILES: CN1CCC(c2nc3cc(-c4ccc(Cl)cc4Cl)nc(Cl)n3n2)CC1]

270 mg (0.71 mmol) of 7-(2,4-dichlorophenyl)-2-(1-methylpiperidin-4-yl)[1,2,4]triazolo[1,5-c]pyrimidin-5(6H)-one (Example 48A) were initially charged in phosphorus oxychloride (2 ml), 650 mg (2.90 mmol) of benzyltriethylammonium chloride were added and the mixture was then stirred at 120° C. for 3 h. The reaction mixture was poured into saturated aqueous sodium bicarbonate solution (150 ml), and solid sodium bicarbonate was added until a pH of 7 had been reached. The solid was filtered off with suction and dried. This gave 190 mg (65% of theory) of the product as a solid.

LCMS (Method 8): $R_t$=0.98 min. (m/z=396 (M+H)$^+$)

$^1$H-NMR (400 MHz, DMSO-$d_6$): δ=10.47 (br, 1H), 8.21 (s, 1H), 7.84 (d, 1H), 7.72 (d, 1H), 7.64 (dd, 1H), 7.53 (s, 1H), 3.53 (m, 2H), 3.30-3.10 (m, 2H), 2.79 (d, 3H), 2.67 (m, 1H), 2.32 (m, 3H), 2.14 (m, 2H).

Example 50A 7-(2-Chloro-4-fluorophenyl)-2-[1-(propan-2-yl)piperidin-4-yl][1,2,4]triazolo[1,5-c]pyrimidin-5(6H)-one

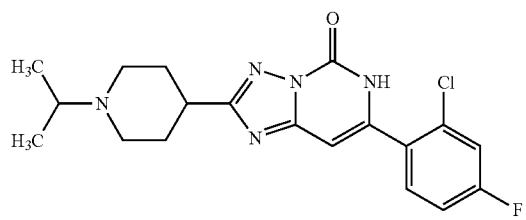 [SMILES: CC(C)N1CCC(c2nc3cc(-c4ccc(F)cc4Cl)[nH]c(=O)n3n2)CC1]

1.5 g (5.14 mmol) of ethyl[(Z)-1-(2-chloro-4-fluorophenyl)-2-cyanoethenyl]carbamate (Example 36A) and 952 mg (5.14 mmol) of 1-(propan-2-yl)piperidine-4-carbohydrazide (Example 38A) were dissolved in 27 ml of N-methylpyrrolidone, and the mixture was stirred under argon at an oil bath temperature of 160° C. in a flask with fitted calcium chloride drying tube for 3 h. The reaction mixture was cooled to RT, water (50 ml) was added and the mixture was stirred for 15 min. The resulting precipitate was filtered off, washed with a little water and then dried under high vacuum. This gave 1.25 g (61% of theory) of the product.

LCMS (Method 8): $R_t$=0.68 min. (m/z=390 (M+H)$^+$)

$^1$H-NMR (400 MHz, DMSO-$d_6$): δ=7.59-7.68 (m, 2H), 7.37 (dt, 1H), 6.70 (s, 1H), 3.30 (s, br, 1H), 2.9-3.1 (m, 2H), 2.77-2.9 (m, 2H), 2.35-2.48 (m, 2H), 2.04 (d, 2H), 1.79 (dd, 2H), 1.04 (d, 6H).

Example 51A 7-(2,4-Difluorophenyl)-2-[1-(propan-2-yl)piperidin-4-yl][1,2,4]triazolo[1,5-c]pyrimidin-5(6H)-one

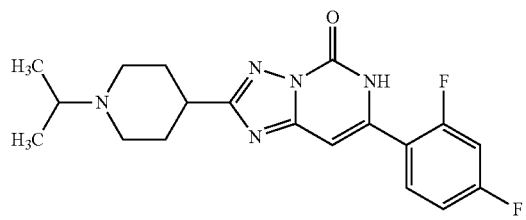 [SMILES: CC(C)N1CCC(c2nc3cc(-c4ccc(F)cc4F)[nH]c(=O)n3n2)CC1]

2.0 g (4.12 mmol) of ethyl[(Z)-2-cyano-1-(2,4-difluorophenyl)ethenyl]carbamate (Example 37A) and 916 mg (4.95 mmol) of 1-(propan-2-yl)piperidine-4-carbohydrazide (Example 38A) were dissolved in 24 ml of N-methylpyrrolidone, and the mixture was stirred under argon at an oil bath temperature of 160° C. in a flask with fitted calcium chloride drying tube for 6 h. The reaction mixture was cooled to RT, water (50 ml) was added and the mixture was stirred for 15 min. The mixture was extracted with ethyl acetate (three times 50 ml each) and the combined organic phases were freed from the solvent. The residue was purified by preparative HPLC (Method 11). This gave 660 mg (41% of theory) of the product.

LCMS (Method 6): $R_t$=0.63 min. (m/z=374 (M+H)$^+$)

$^1$H-NMR (400 MHz, DMSO-d$_6$): δ=7.83 (dd, 1H), 7.41 (dt, 1H), 7.23 (dt, 1H), 6.80 (s, 1H), 3.32 (m, 1H), 2.93-3.1 (m, 3H), 2.81-2.93 (m, 1H), 2.53-2.62 (m, 2H), 2.07 (d, 2H), 1.84 (dd, 2H), 1.08 (d, 6H).

Example 52A

5-Chloro-7-(2-chloro-4-fluorophenyl)-2-[1-(propan-2-yl)piperidin-4-yl][1,2,4]triazolo[1,5-c]-pyrimidine hydrochloride

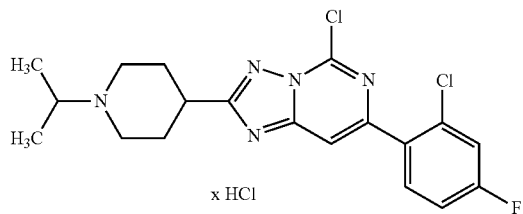 [SMILES: CC(C)N1CCC(c2nc3cc(-c4ccc(F)cc4Cl)nc(Cl)n3n2)CC1]

x HCl 4.5 ml of phosphoryl chloride were added to 1.25 g (3.2 mmol) of 7-(2-chloro-4-fluorophenyl)-2-[1-(propan-2-yl)piperidin-4-yl][1,2,4]triazolo[1,5-c]pyrimidin-5(6H)-one (Example 50A), 1.46 g (6.41 mmol) of benzyltriethylammonium chloride were added and the reaction mixture was stirred at 120° C. for 16 h. The reaction mixture was concentrated and carefully, with vigorous stirring, added to ice. The mixture was stirred for another 10 min. Three times, the aqueous phase was extracted with dichloromethane. The combined organic phases were freed from the solvent and the residue was dried under high vacuum. This gave 715 mg (55% of theory) of the product.

LCMS (Method 3): $R_t$=1.41 min. (m/z=408 (M+H)$^+$)

Example 53A

5-Chloro-7-(2,4-difluorophenyl)-2-[1-(propan-2-yl)piperidin-4-yl][1,2,4]triazolo[1,5-c]pyrimidine hydrochloride

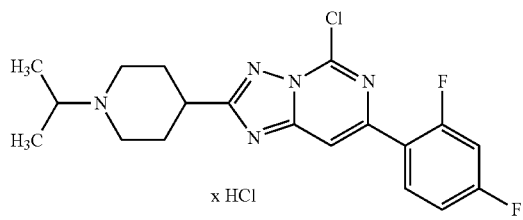 [SMILES: CC(C)N1CCC(c2nc3cc(-c4ccc(F)cc4F)nc(Cl)n3n2)CC1]

x HCl 4.5 ml of phosphoryl chloride were added to 670 mg (1.72 mmol) of 7-(2,4-difluorophenyl)-2-[1-(propan-2-yl)piperidin-4-yl][1,2,4]triazolo[1,5-c]pyrimidin-5(6H)-one (Example 51A), 785 mg (3.45 mmol) of benzyltriethylammonium chloride were added and the reaction mixture was stirred at 120° C. for 7 h. The reaction mixture was concentrated and carefully, with vigorous stirring, added to ice. Three times, the aqueous phase was extracted with dichloromethane. The combined organic phases were freed from the solvent and used without further purification. This gave 590 mg (80% of theory) of the product.

LCMS (Method 3): $R_t$=1.39 min. (m/z=392 (M+H)$^+$)

Example 54A

Ethyl{4-[7-(2,4-dichlorophenyl)-5-oxo-5,6-dihydro[1,2,4]triazolo[1,5-c]pyrimidin-2-yl]piperidin-1-yl}acetate

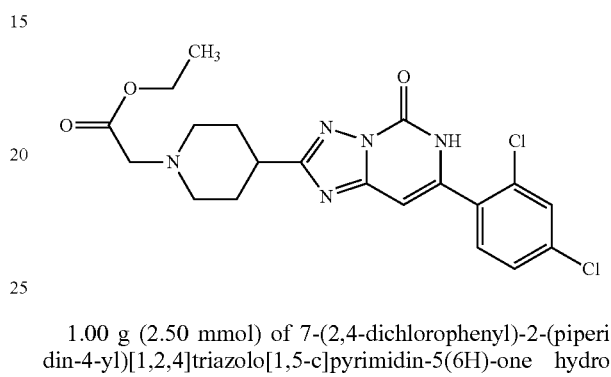

1.00 g (2.50 mmol) of 7-(2,4-dichlorophenyl)-2-(piperidin-4-yl)[1,2,4]triazolo[1,5-c]pyrimidin-5(6H)-one hydrochloride (Example 43A) were in DMF (6 ml), and 332 μl (3 mmol) of ethyl 1-bromoacetate and 862 mg (6.24 mmol) of potassium carbonate were added. The reaction mixture was stirred at 80° C. for 16 h, the solution was then filtered and ethyl acetate and water were added. The phases were separated, and the aqueous phase was extracted with ethyl acetate (two times 15 ml). The combined organic phases were washed with saturated aqueous sodium chloride solution, dried (magnesium sulfate) and concentrated. The product was applied to kieselguhr and chromatographed on silica gel using dichloromethane/methanol (70:30). This gave 505 mg (45% of theory) of the product.

LCMS (Method 8): $R_t$=0.79 min. (m/z=450 (M+H)$^+$)

$^1$H-NMR (400 MHz, DMSO-d$_6$): δ=12.29 (s, br, 1H), 7.84 (s, 1H), 7.62 (s, 2H), 6.82 (s, 1H), 4.09 (q, 2H), 3.32 (s, br, 2H), 2.87-2.94 (m, 2H), 2.75-2.85 (m, 1H), 2.36 (dt, 2H), 1.95-2.02 (m, 2H), 1.73-1.86 (m, 2H), 1.20 (t, 3H).

Example 55A

Ethyl{4-[5-chloro-7-(2,4-dichlorophenyl)[1,2,4]triazolo[1,5-c]pyrimidin-2-yl]piperidin-1-yl}-acetate

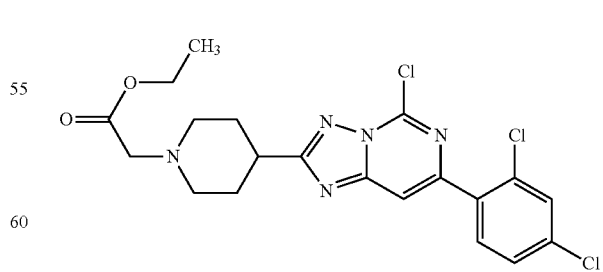

5 ml of phosphoryl chloride were added to 500 mg (1.11 mmol) of ethyl{4-[7-(2,4-dichlorophenyl)-5-oxo-5,6-dihydro [1,2,4]triazolo[1,5-c]-pyrimidin-2-yl]piperidin-1-yl}acetate (Example 54A), 1.01 g (4.44 mmol) of benzyltriethylammonium chloride were added and the reaction mixture was stirred at 120° C. for 2.5 h. The reaction mixture was concentrated and carefully, with vigorous stirring, added to saturated aqueous sodium bicarbonate solution. The pH was adjusted to pH=7 by addition of solid sodium bicarbonate. The aqueous phase was extracted three times with dichloromethane. The combined organic phases were washed once with water, dried with magnesium sulfate and then freed from the solvent. Without further purification, this gave 506 mg (88% of theory) of the product.

LCMS (Method 3): $R_t$=1.59 min. (m/z=468 (M+H)$^+$)

Example 56A

Ethyl(4-{5-[(2-{[6-amino-5-(trifluoroacetyl)pyridin-2-yl]amino}ethyl)amino]-7-(2,4-dichloro-phenyl)[1,2,4]triazolo[1,5-c]pyrimidin-2-yl}piperidin-1-yl)acetate

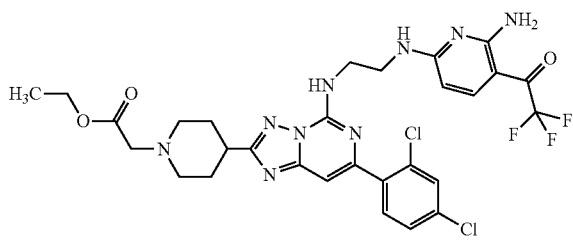 [SMILES: CCOC(=O)CN1CCC(c2nc3cc(-c4ccc(Cl)cc4Cl)nc(NCCNc4ccc(C(=O)C(F)(F)F)c(N)n4)n3n2)CC1]

120 mg (0.23 mmol) of ethyl{4-[5-chlor-7-(2,4-dichlorophenyl)[1,2,4]triazolo[1,5-c]pyrimidin-2-yl]piperidin-1-yl}acetate (Example 55A), 78.7 mg (0.28 mmol) of 1-{2-amino-6-[(2-aminoethyl)-amino]pyridin-3-yl}-2,2,2-trifluoroethanone hydrochloride (Example 13A) and 0.24 ml (1.38 mmol) of N,N-diisopropylethylamine were initially charged in 1 ml of DMSO. The mixture was heated in the microwave at 130° C. for 30 min. This gave, after purification of the crude product by preparative HPLC (Method 11), 141 mg (90% of theory) of the product as a solid.

LCMS (Method 6): $R_t$=1.58 min. (m/z=680 (M+H)$^1$)

Example 57A

Ethyl{4-[5-({2-[(5-cyanopyridin-2-yl)amino]ethyl}amino)-7-(2,4-dichlorophenyl)[1,2,4]-triazolo[1,5-c]pyrimidin-2-yl]piperidin-1-yl}acetate

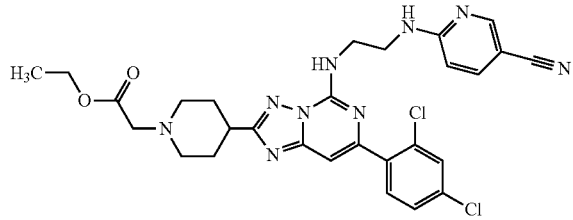 [SMILES: CCOC(=O)CN1CCC(c2nc3cc(-c4ccc(Cl)cc4Cl)nc(NCCNc4ccc(C#N)cn4)n3n2)CC1]

120 mg (0.23 mmol) of ethyl{4-[5-chloro-7-(2,4-dichlorophenyl)[1,2,4]triazolo[1,5-c]pyrimidin-2-yl]piperidin-1-yl}acetate (Example 55A), 54.9 mg (0.28 mmol) of 6-[(2-aminoethyl)amino]-pyridine-3-carbonitrile dihydrochloride (Example 2A) and 0.24 ml (1.38 mmol) of N,N-diisopropylethylamine were initially charged in 2.33 ml of DMSO. The mixture was heated in the microwave at 130° C. for 30 min. This gave, after purification of the crude product by preparative HPLC (Method 11), 113 mg (77% of theory) of the product as a solid.

LCMS (Method 6): $R_t$=1.41 min. (m/z=594 (M+H)$^+$)

Exemplary Embodiments

Example 1

1-(2-Amino-6-{[2-({7-(2,4-dichlorophenyl)-2-[1-(propan-2-yl)piperidin-4-yl][1,2,4]triazolo[1,5-c]-pyrimidin-5-yl}amino)ethyl]amino}pyridin-3-yl)-2,2,2-trifluoroethanone

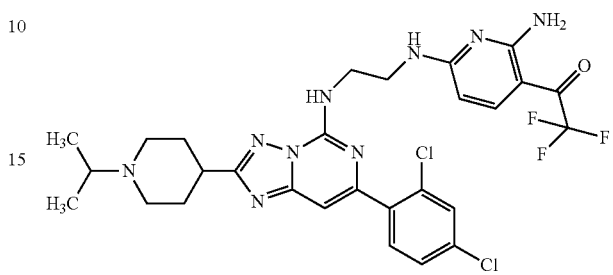

250 mg (0.59 mmol) of 5-chloro-7-(2,4-dichlorophenyl)-2-[1-(propan-2-yl)piperidin-4-yl][1,2,4]-triazolo[1,5-c]pyrimidine hydrochloride (Example 40A), 201 mg (0.71 mmol) of 1-{2-amino-6-[(2-aminoethyl)amino]pyridin-3-yl}-2,2,2-trifluoroethanone hydrochloride (Example 13A) and 0.615 ml (3.5 mmol) of N,N-diisopropylethylamine were initially charged in 4 ml of DMSO. The mixture was heated in the microwave at 130° C. for 30 min. This gave, after purification of the crude product by preparative HPLC (Method 11), 210 mg (56% of theory) of the product as a solid.

LCMS (Method 8): $R_t$=1.15 min. (m/z=636 (M+H)$^+$)

$^1$H-NMR (400 MHz, DMSO-d$_6$): δ=10.64 (br, 1H), 8.37 (t, 1H), 7.66 (s, 1H), 7.59 (d, 1H), 7.50 (d, 1H), 7.41 (dd, 1H), 7.20 (s, 1H), 5.91 (d, 1H), 3.87-3.75 (br m, 4H), 3.46 (m, 4H), 3.28-3.07 (m, 4H), 2.39 (m, 1H), 2.28 (m, 4H), 1.33 (d, 6H).

Example 2

2-Amino-6-{[2-({7-(2,4-dichlorophenyl)-2-[1-(propan-2-yl)piperidin-4-yl][1,2,4]triazolo[1,5-c]-pyrimidin-5-yl}amino)ethyl]amino}pyridine-3-carbonitrile

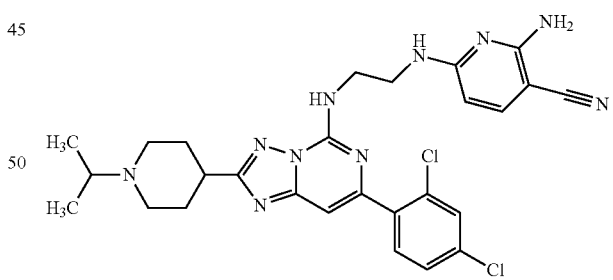

50 mg (0.12 mmol) of 5-chloro-7-(2,4-dichlorophenyl)-2-[1-(propan-2-yl)piperidin-4-yl][1,2,4]triazolo[1,5-c]pyrimidine hydrochloride (Example 40A), 30 mg (0.14 mmol) of 2-amino-6-[(2-aminoethyl)amino]pyridine-3-carbonitrile dihydrochloride (Example 9A) and 0.125 ml (3.5 mmol) of N,N-diisopropylethylamine were initially charged in 1 ml of DMSO. The mixture was heated in the microwave at 130° C. for 30 min. This gave, after purification of the crude product by preparative HPLC (Method 11), 45 mg (68% of theory) of the product as a solid.

LCMS (Method 3): $R_t$=1.63 min. (m/z=565 (M+H)$^+$)

¹H-NMR (400 MHz, DMSO-d₆): δ=10.21 (br, 1H), 8.37 (t, 1H), 7.75 (d, 1H), 7.60 (d, 1H), 7.51 (dd, 1H), 7.38 (br, 1H), 7.20 (s, 1H), 5.82 (br, 1H), 3.74 (m, 2H), 3.64 (m, 2H), 3.47 (m, 4H), 3.16 (m, 4H), 2.41 (m, 1H), 2.27 (m, 4H), 1.32 (d, 6H).

Example 3

6-{[2-({7-(2,4-Dichlorophenyl)-2-[1-(propan-2-yl)piperidin-4-yl][1,2,4]triazolo[1,5-c]pyrimidin-5-yl}amino)ethyl]amino}pyridine-3-carbonitrile

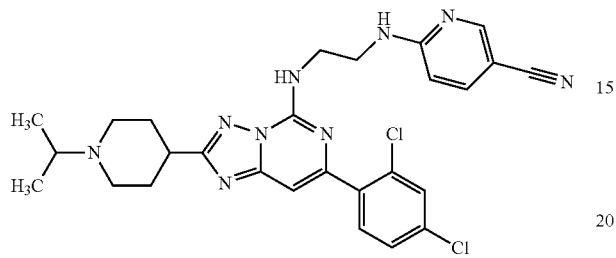

50 mg (0.12 mmol) of 5-chloro-7-(2,4-dichlorophenyl)-2-[1-(propan-2-yl)piperidin-4-yl][1,2,4]-triazolo[1,5-c]pyrimidine hydrochloride (Example 40A), 28 mg (0.14 mmol) of 6-[(2-aminoethyl)-amino]pyridine-3-carbonitrile dihydrochloride (Example 2A) and 0.125 ml (3.5 mmol) of N,N-diisopropylethylamine were initially charged in 1 ml of DMSO. The mixture was heated in the microwave at 130° C. for 30 min. This gave, after purification of the crude product by preparative HPLC (Method 11), 48 mg (74% of theory) of the product as a solid.

LCMS (Method 8): $R_t$=1.06 min. (m/z=550 (M+H)⁺)

¹H-NMR (400 MHz, DMSO-d₆): δ=10.17 (br, 1H), 8.36 (m, 2H), 7.88 (br, 1H), 7.73 (d, 1H), 7.60-7.49 (m, 4H), 7.18 (s, 1H), 6.50 (br, 1H), 3.72 (m, 2H), 3.64 (m, 2H), 3.48 (m, 4H), 3.29-3.11 (m, 4H), 2.41 (m, 1H), 2.26 (m, 4H), 1.32 (d, 6H).

Example 4

1-(2-Amino-6-{[2-({7-(2,4-dichlorophenyl)-2-[1-(propan-2-yl)piperidin-4-yl][1,2,4]triazolo[1,5-c]-pyrimidin-5-yl}amino)ethyl]amino}pyridin-3-yl)propan-1-one

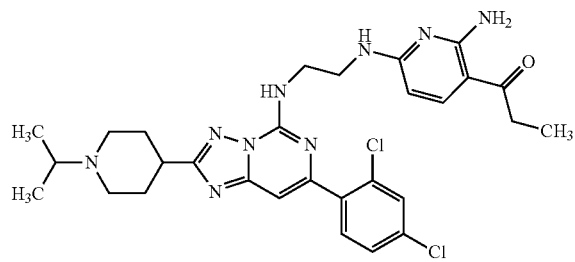 [SMILES: CCC(=O)c1ccc(NCCNc2nc(-c3ccc(Cl)cc3Cl)cc3nc(C4CCN(C(C)C)CC4)nn23)nc1N]

30 mg (0.07 mmol) of 5-chloro-7-(2,4-dichlorophenyl)-2-[1-(propan-2-yl)piperidin-4-yl][1,2,4]-triazolo[1,5-c]pyrimidine hydrochloride (Example 40A), 21 mg (0.09 mmol) of 1-{2-amino-6-[(2-aminoethyl)amino]pyridin-3-yl}propan-1-one hydrochloride (Example 25A) and 75 µl (0.4 mmol) of N,N-diisopropylethylamine were initially charged in 1 ml of DMSO. The mixture was heated in the microwave at 120° C. for 30 min. This gave, after purification of the crude product by preparative HPLC (Method 11), 21 mg (50% of theory) of the product as a solid.

LCMS (Method 6): $R_t$=1.19 min. (m/z=596 (M+H)⁺)

¹H-NMR (400 MHz, DMSO-d₆): δ=10.06 (br, 1H), 8.36 (br, 1H), 7.81 (m, 1H), 7.68 (m, 1H), 7.57 (dd, 1H), 7.44 (br m, 1H), 7.20 (s, 1H), 5.75 (br, 1H), 3.90-3.71 (m, 4H), 3.49 (m, 4H), 3.27-3.12 (m, 4H), 2.74 (m, 2H), 2.40 (m, 1H), 2.33-2.16 (m, 4H), 1.33 (d, 6H), 1.06 (t, 3H).

Example 5

1-{2-Amino-6-[(1-{7-(2,4-dichlorophenyl)-2-[1-(propan-2-yl)piperidin-4-yl][1,2,4]triazolo[1,5-c]-pyrimidin-5-yl}piperidin-3-yl)amino]pyridin-3-yl}-2,2,2-trifluoroethanone

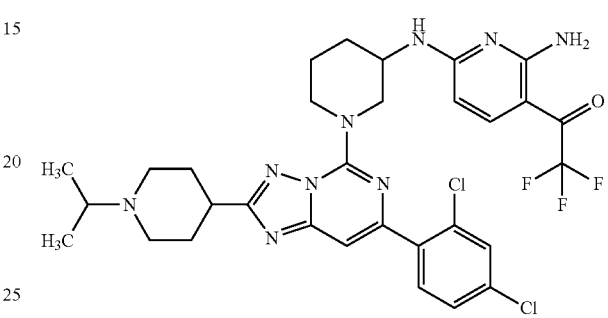

30 mg (0.07 mmol) of 5-chloro-7-(2,4-dichlorophenyl)-2-[1-(propan-2-yl)piperidin-4-yl][1,2,4]-triazolo[1,5-c]pyrimidine, 28 mg (0.09 mmol) of 1-[2-amino-6-(piperidin-3-ylamino)pyridin-3-yl]-2,2,2-trifluoroethanone hydrochloride (Example 22A) and 75 µl (0.4 mmol) of N,N-diisopropylethylamine were initially charged in 1 ml of DMSO. The mixture was heated in the microwave at 120° C. for 30 min. This gave, after purification of the crude product by preparative HPLC (Method 11), 20 mg (42% of theory) of the product as a solid.

LCMS (Method 9): $R_t$=2.16 min. (m/z=676 (M+H)⁺)

¹H-NMR (400 MHz, DMSO-d₆): δ=9.59 (br, 1H), 8.51 (br, 1H), 8.02 (br, 1H), 7.77-7.67 (m, 3H), 7.54-7.47 (m, 2H), 7.38 (s, 1H), 5.95 (d, 1H), 4.36-4.23 (m, 2H), 3.48 (m, 1H) 3.41 (m, 2H), 3.22-3.04 (m, 2H), 2.26 (m, 2H), 2.07 (m, 2H), 1.72 (m, 1H), 1.29 (d, 6H). A number of other signals are hidden under the signal of water.

Example 6

1-{2-Amino-6-[(1-{7-(2,4-difluorophenyl)-2-[1-(propan-2-yl)piperidin-4-yl][1,2,4]triazolo[1,5-c]-pyrimidin-5-yl}piperidin-3-yl)amino]pyridin-3-yl}propan-1-one

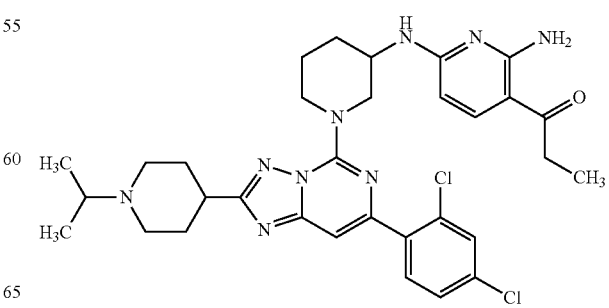

30 mg (0.07 mmol) of 5-chloro-7-(2,4-dichlorophenyl)-2-[1-(propan-2-yl)piperidin-4-yl][1,2,4]-triazolo[1,5-c]pyrimidine, 24 mg (0.09 mmol) of 1-[2-amino-6-(piperidin-3-ylamino)pyridin-3-yl]propan-1-one hydrochloride (Example 27A) and 75 μl (0.4 mmol) of N,N-diisopropylethylamine were initially charged in 1 ml of DMSO. The mixture was heated in the microwave at 120° C. for 30 min. This gave, after purification of the crude product by preparative HPLC (Method 11), 20 mg (42% of theory) of the product as a solid.

LCMS (Method 6): $R_t$=1.35 min. (m/z=636 (M+H)$^+$)

$^1$H-NMR (400 MHz, DMSO-$d_6$): δ=9.84 (br, 1H), 7.90 (br, 1H), 7.74 (m, 1H), 7.70 (d, 1H), 7.53 (m, 1H), 7.38 (s, 1H), 5.96 (br, 1H), 4.45-4.27 (br, 2H), 4.20-4.03 (br, 2H), 3.51-3.38 (m, 4H), 3.10 (m, 4H), 2.79 (m, 2H), 2.29-1.96 (m, 8H), 1.77 (m, 2H), 1.29 (d, 6H), 1.06 (t, 3H).

Example 7

1-(2-Amino-6-{[2-({7-(2,4-difluorophenyl)-2-[1-(propan-2-yl)piperidin-4-yl][1,2,4]triazolo[1,5-c]-pyrimidin-5-yl}amino)ethyl]amino}pyridin-3-yl)-2,2,2-trifluoroethanone hydrochloride

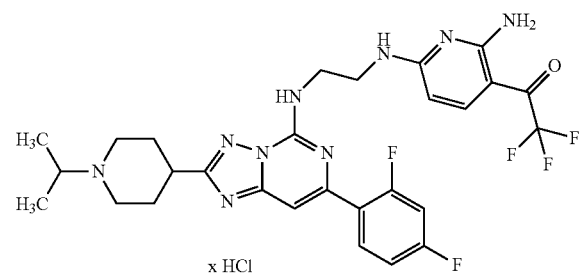 [SMILES: CC(C)N1CCC(c2nc3cc(-c4ccc(F)cc4F)nc(NCCNc4ccc(C(=O)C(F)(F)F)c(N)n4)n3n2)CC1]

x HCl 55 mg (0.14 mmol) of 5-chloro-7-(2,4-difluorophenyl)-2-[1-(propan-2-yl)piperidin-4-yl][1,2,4]-triazolo[1,5-c]pyrimidine hydrochloride (Example 53A), 48.9 mg (0.17 mmol) of 1-{2-amino-6-[(2-aminoethyl)amino]pyridin-3-yl}-2,2,2-trifluoroethanone hydrochloride (Example 13A) and 0.147 ml (0.84 mmol) of N,N-diisopropylethylamine were initially charged in 1 ml of DMSO. The mixture was heated in the microwave at 130° C. for 30 min. This gave, after purification of the crude product by preparative HPLC (Method 11), 21 mg (23% of theory) of the product as a solid.

LCMS (Method 3): $R_t$=1.71 min. (m/z=604 (M+H)$^+$)

$^1$H-NMR (400 MHz, DMSO-$d_6$): δ=10.12 (s, br, 1H), 8.29 (t, 1H), 7.95 (dd, 1H), 7.29-7.43 (m, 1H), 7.28 (s, 1H), 6.99 (t, 1H), 5.81 (d, 1H), 3.87 (m, 2H), 3.69 (m, 2H), 3.42-3.55 (m, 4H), 3.08-3.28 (m, 4H), 2.35-2.41 (m, 2H), 2.13-2.31 (m, 4H), 1.31 (d, 6H).

Example 8

6-[(1-{7-(2,4-Difluorophenyl)-2-[1-(propan-2-yl)piperidin-4-yl][1,2,4]triazolo[1,5-c]pyrimidin-5-yl}piperidin-3-yl)amino]pyridine-3-carbonitrile

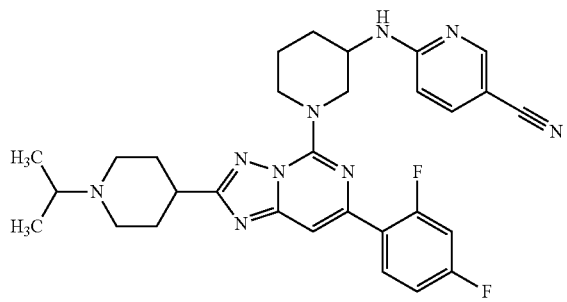

80 mg (0.2 mmol) of 5-chloro-7-(2,4-difluorophenyl)-2-[1-(propan-2-yl)piperidin-4-yl][1,2,4]-triazolo[1,5-c]pyrimidine hydrochloride (Example 53A), 60.9 mg (0.25 mmol) of 6-(piperidin-3-ylamino)pyridine-3-carbonitrile hydrochloride (Example 19A) and 0.21 ml (1.23 mmol) of N,N-diisopropylethylamine were initially charged in 1 ml of DMSO. The mixture was heated in the microwave at 130° C. for 30 min. This gave, after purification of the crude product by preparative HPLC (Method 11), 39 mg (33% of theory) of the product as a solid.

LCMS (Method 9): $R_t$=1.83 min. (m/z=558 (M+H)$^+$)

$^1$H-NMR (400 MHz, DMSO-$d_6$): δ=8.38 (d, 1H), 8.13 (dd, 1H), 7.61 (t, 1H), 7.38-7.45 (m, 2H), 7.23 (dt, 1H), 6.52 (d, 1H), 4.36-4.45 (m, 1H), 4.13-4.28 (m, 2H), 3.87-3.98 (m, 1H), 2.82 (d, 2H), 2.6-2.72 (m, 3H), 2.18-2.28 (m, 2H), 2.03 (m, 2H), 1.88 (m, 2H), 1.6-1.78 (m, 4H), 0.98 (d, 6H).

Example 9

2-Amino-6-[(1-{7-(2,4-difluorophenyl)-2-[1-(propan-2-yl)piperidin-4-yl][1,2,4]triazolo[1,5-c]-pyrimidin-5-yl}piperidin-3-yl)amino]pyridine-3-carbonitrile

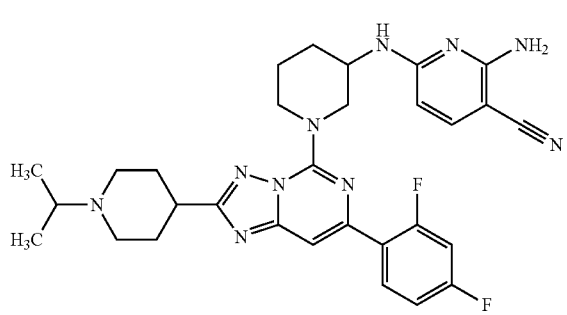 [SMILES: CC(C)N1CCC(c2nc3cc(-c4ccc(F)cc4F)nc(N4CCCC(Nc5ccc(C#N)c(N)n5)C4)n3n2)CC1]

80 mg (0.2 mmol) of 5-chloro-7-(2,4-difluorophenyl)-2-[1-(propan-2-yl)piperidin-4-yl][1,2,4]-triazolo[1,5-c]pyrimidine hydrochloride (Example 53A), 69.1 mg (0.25 mmol) of 2-amino-6-(piperidin-3-ylamino)pyridine-3-carbonitrile hydrochloride (Example 20A) and 0.213 ml (1.23 mmol) of N,N-diisopropylethylamine were initially charged in 1 ml of DMSO. The mixture was heated in the microwave at 130° C.

for 30 min. This gave, after purification of the crude product by preparative HPLC (Method 11), 34 mg (28% of theory) of the product as a solid.

LCMS (Method 9): $R_t$=1.79 min. (m/z=573 (M+H)$^+$)

$^1$H-NMR (400 MHz, DMSO-$d_6$): δ=8.11 (dd, 1H), 7.36-7.45 (m, 2H), 7.19-7.3 (m, 2H), 7.04-7.16 (s, br, 1H), 6.23 (s, 1H), 5.76 (s, br, 1H), 4.08-4.45 (m, br, 3H), 3.78-3.95 (m, br, 2H), 2.79-2.88 (m, 3H), 2.65-2.77 (m, 2H), 2.25 (t, 2H), 1.89-2.04 (m, 4H), 1.6-1.78 (m, 4H), 0.99 (d, 6H).

Example 10

1-{2-Amino-6-[(1-{7-(2,4-difluorophenyl)-2-[1-(propan-2-yl)piperidin-4-yl][1,2,4]triazolo[1,5-c]-pyrimidin-5-yl}piperidin-3-yl)amino]pyridin-3-yl}-2,2,2-trifluoroethanone

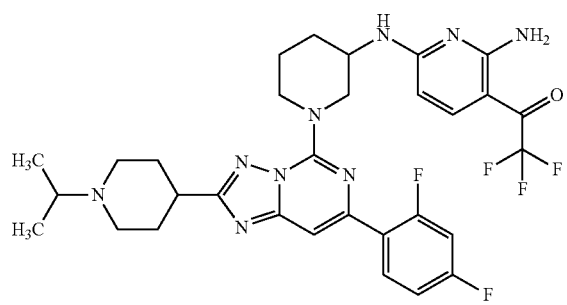 [SMILES: CC(C)N1CCC(c2nc3cc(-c4ccc(F)cc4F)nc(N4CCCC(Nc5ccc(C(=O)C(F)(F)F)c(N)n5)C4)n3n2)CC1]

80 mg (0.2 mmol) of 5-chloro-7-(2,4-difluorophenyl)-2-[1-(propan-2-yl)piperidin-4-yl][1,2,4]-triazolo[1,5-c]pyrimidine, 81.2 mg (0.24 mmol) of 1-[2-amino-6-(piperidin-3-ylamino)pyridin-3-yl]-2,2,2-trifluoroethanone hydrochloride (Example 22A) and 0.213 ml (1.23 mmol) of N,N-diisopropylethylamine were initially charged in 1 ml of DMSO. The mixture was heated in the microwave at 130° C. for 30 min. This gave, after purification of the crude product by preparative HPLC (Method 11), 56 mg (42% of theory) of the product as a solid.

LCMS (Method 3): $R_t$=1.84 min. (m/z=644 (M+H)$^+$)

$^1$H-NMR (400 MHz, DMSO-$d_6$): δ=8.52 (s, br, 1H), 8.12 (dd, 1H), 7.91 (d, 1H), 7.65 (s, br, 1H), 7.36-7.49 (m, 3H), 7.18 (t, 1H), 5.88 (d, 1H), 4.33-4.51 (m, br, 2H), 4.07-4.22 (m, 2H), 3.44-3.57 (m, 1H), 2.7-2.81 (m, 2H), 2.58-2.69 (m, 2H), 2.08-2.2 (m, 2H), 1.99-2.09 (m, 2H), 1.82-1.94 (m, 2H), 1.57-1.78 (m, 4H), 0.94 (d, 6H).

The enantiomer separation of racemic 1-{2-amino-6-[(1-{7-(2,4-difluorophenyl)-2-[1-(propan-2-yl)piperidin-4-yl][1,2,4]triazolo[1,5-c]-pyrimidin-5-yl}piperidin-3-yl)amino]pyridin-3-yl}-2,2,2-trifluoroethanone (Example 10) was carried out under the following conditions:

A sample of Example 10 (46 mg) was dissolved in 2-propanol and chromatographed on a Daicel Chiralpak AS-H, 5 μm, 250 mm×20 mm column (flow rate: 15 ml/min; detection at 220 nm; injection volume: 1000 μl; eluent: isohexane:2-propanol+0.2% diethylamine (70:30), temperature: 40° C.). Two fractions were isolated:

Example Ent-A-10

14 mg of product were isolated in >99% ee.
retention time 4.25 min

Example Ent-B-10

20 mg of product were isolated in >99% ee.
retention time 6.01 min

Example 11

6-{[2-({7-(2-Chloro-4-fluorophenyl)-2-[1-(propan-2-yl)piperidin-4-yl][1,2,4]triazolo[1,5-c]-pyrimidin-5-yl}amino)ethyl]amino}pyridine-3-carbonitrile hydrochloride

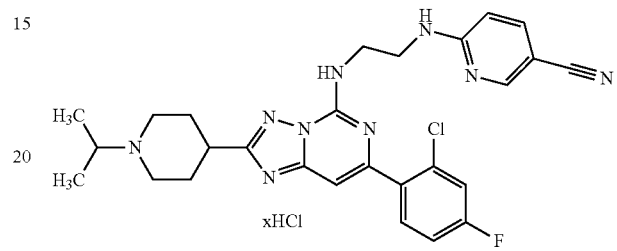

55 mg (0.11 mmol) of 5-chloro-7-(2-chloro-4-fluorophenyl)-2-[1-(propan-2-yl)piperidin-4-yl]-[1,2,4]triazolo[1,5-c]pyrimidine hydrochloride (Example 52A), 27.3 mg (0.14 mmol) of 6-[(2-aminoethyl)amino]pyridine-3-carbonitrile hydrochloride (Example 2A) and 0.12 ml (0.69 mmol) of N,N-diisopropylethylamine were initially charged in 1 ml of DMSO. The mixture was heated in the microwave at 130° C. for 30 min. This gave, after purification of the crude product by preparative HPLC (Method 11), 28 mg (43% of theory) of the product as a solid.

LCMS (Method 8): $R_t$=1.01 min. (m/z=534 (M+H)$^+$)

$^1$H-NMR (400 MHz, DMSO-$d_6$): δ=10.19 (s, br, 1H), 8.3-8.39 (m, 1H), 7.93 (s, br, 1H), 7.51-7.67 (m, 3H), 7.26-7.36 (dt, 1H), 7.14 (s, 1H), 6.50 (s, br, 1H), 3.71 (m, 2H), 3.63 (m, 2H), 3.42-3.53 (m, 2H), 3.3-3.4 (m, 1H), 3.1-3.29 (m, 3H), 2.38-2.43 (m, 1H), 2.18-2.32 (m, 4H), 1.31 (d, 6H).

Example 12

2-Amino-6-[(1-{7-(2-chloro-4-fluorophenyl)-2-[1-(propan-2-yl)piperidin-4-yl][1,2,4]triazolo[1,5-c]-pyrimidin-5-yl}piperidin-3-yl)amino]pyridine-3-carbonitrile

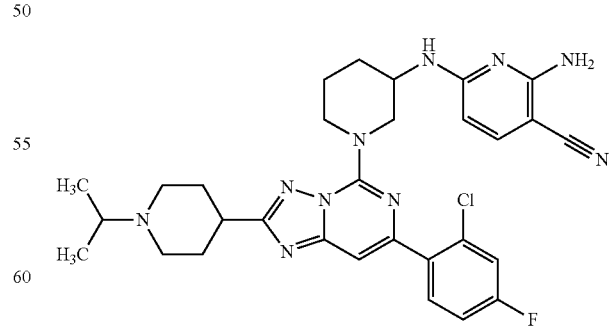

80 mg (0.17 mmol) of 5-chloro-7-(2-chloro-4-fluorophenyl)-2-[1-(propan-2-yl)piperidin-4-yl][1,2,4]triazolo[1,5-c]pyrimidine hydrochloride (Example 52A), 56.3 mg (0.2 mmol) of 2-amino-6-(piperidin-3-ylamino)pyridine-3-carbonitrile hydrochloride (Example 20A) and 0.17 ml (0.99 mmol) of N,N-diisopropylethylamine were initially charged in 1 ml of DMSO. The mixture was heated in the microwave at 130° C. for 30 min. This gave, after purification of the crude product by preparative HPLC (Method 11), 47 mg (44% of theory) of the product as a solid.

LCMS (Method 3): $R_t$=1.66 min. (m/z=589 (M+H)$^+$)

$^1$H-NMR (400 MHz, DMSO-d$_6$): δ=9.87 (s, br, 1H), 7.75 (dd, 1H), 7.58 (dd, 1H), 7.3-7.4 (m, 3H), 5.85 (s, br, 1H), 4.2-4.6 (m, 4H), 4.7-4.9 (m, 2H), 3.4-3.54 (m, 3H), 3.05-3.20 (m, 3H), 2.29-2.36 (m, 1H), 2.17-2.28 (m, 2H), 2.06-2.17 (m, 2H), 1.92-2.06 (m, 2H), 1.62-1.76 (m, 2H), 1.31 (d, 6H).

Example 13

1-{2-Amino-6-[(1-{7-(2-chloro-4-fluorophenyl)-2-[1-(propan-2-yl)piperidin-4-yl][1,2,4]-triazolo[1,5-c]pyrimidin-5-yl}piperidin-3-yl)amino]pyridin-3-yl}-2,2,2-trifluoroethanone

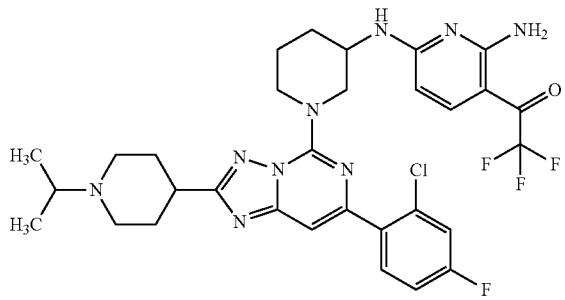

80 mg (0.17 mmol) of 5-chloro-7-(2-chloro-4-fluorophenyl)-2-[1-(propan-2-yl)piperidin-4-yl][1,2,4]triazolo[1,5-c]pyrimidine hydrochloride, 64.9 mg (0.2 mmol) of 1-[2-amino-6-(piperidin-3-ylamino)pyridin-3-yl]-2,2,2-trifluoroethanone hydrochloride (Example 22A) and 0.17 ml (0.99 mmol) of N,N-diisopropylethylamine were initially charged in 1 ml of DMSO. The mixture was heated in the microwave at 130° C. for 30 min. This gave, after purification of the crude product by preparative HPLC (Method 11), 32 mg (28% of theory) of the product as a solid.

LCMS (Method 3): $R_t$=1.84 min. (m/z=660 (M+H)$^+$)

$^1$H-NMR (400 MHz, DMSO-d$_6$): δ=8.50 (s, br, 1H), 7.93 (d, 1H), 7.75 (dd, 1H), 7.64 (s, br, 1H), 7.56 (dd, 1H), 7.46 (d, 1H), 7.27-7.38 (m, 2H), 5.91 (d, 1H), 4.2-4.4 (m, br, 3H), 4.02-4.13 (m, 1H), 3.87-3.97 (m, 1H), 2.7-2.8 (m, 2H), 2.6-2.7 (m, 2H), 2.09-2.2 (m, 2H), 1.95-2.08 (m, 2H), 1.82-1.93 (m, 2H), 1.58-1.77 (m, 4H), 0.94 (d, 6H).

The enantiomer separation of racemic 1-{2-amino-6-[(1-{7-(2-chloro-4-fluorophenyl)-2-[1-(propan-2-yl)piperidin-4-yl][1,2,4]triazolo[1,5-c]pyrimidin-5-yl}piperidin-3-yl)amino]pyridin-3-yl}-2,2,2-trifluoroethanone (Example 13) was carried out under the following conditions:

A sample of Example 13 (22 mg) was dissolved in 1 ml of 2-propanol and chromatographed on a Daicel Chiralpak AS-H, 5 µm, 250 mm×20 mm column (flow rate: 15 ml/min; detection at 220 nm; injection volume: 1000 µl; eluent: isohexane:2-propanol+0.2% diethylamine (70:30), temperature: 40° C.). Two fractions were isolated:

Example Ent-A-13

12 mg of product were isolated in >99% ee.
retention time 4.25 min

Example Ent-B-13

17 mg of product were isolated in >99% ee.
retention time 6.01 min

Example 14

6-[(1-{7-(2-Chloro-4-fluorophenyl)-2-[1-(propan-2-yl)piperidin-4-yl][1,2,4]triazolo[1,5-c]pyrimidin-5-yl}piperidin-3-yl)amino]pyridine-3-carbonitrile

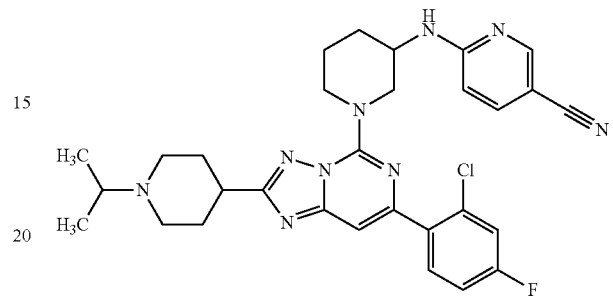

80 mg (0.2 mmol) of 5-chloro-7-(2-chloro-4-fluorophenyl)-2-[1-(propan-2-yl)piperidin-4-yl][1,2,4]triazolo[1,5-c]pyrimidine hydrochloride (Example 52A), 50 mg (0.2 mmol) of 6-(piperidin-3-ylamino)pyridine-3-carbonitrile hydrochloride (Example 19A) and 0.17 ml (0.99 mmol) of N,N-diisopropylethylamine were initially charged in 1 ml of DMSO. The mixture was heated in the microwave at 130° C. for 30 min. This gave, after purification of the crude product by preparative HPLC (Method 11), 39 mg (37% of theory) of the product as a solid.

LCMS (Method 9): $R_t$=1.87 min. (m/z=574 (M+H)$^+$)

$^1$H-NMR (400 MHz, DMSO-d$_6$): δ=9.78 (s, br, 1H), 8.36 (d, 1H), 7.74 (dd, 1H), 7.53-7.67 (m, 3H), 7.3-7.4 (m, 2H), 6.53 (d, 1H), 4.2-4.5 (m, 3H), 4.14 (m, 1H), 3.81 (m, 1H), 3.25-3.4 (m, 2H), 3.08-3.2 (m, 3H), 2.25-2.36 (m, 1H), 1.93-2.24 (m, 5H), 1.63-1.78 (m, 2H), 1.30 (d, 6H).

Example 15

1-(2-Amino-6-{[2-({7-(2-chloro-4-fluorophenyl)-2-[1-(propan-2-yl)piperidin-4-yl][1,2,4]-triazolo[1,5-c]pyrimidin-5-yl}amino)ethyl]amino}pyridin-3-yl)-2,2,2-trifluoroethanone

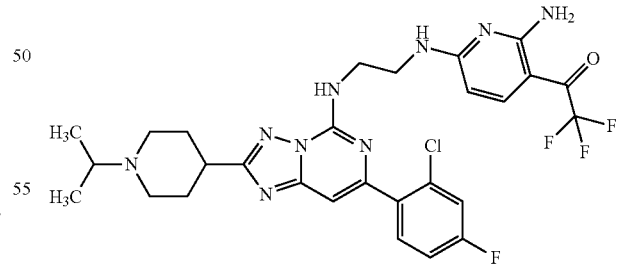

55 mg (0.11 mmol) of 5-chloro-7-(2-chloro-4-fluorophenyl)-2-[1-(propan-2-yl)piperidin-4-yl][1,2,4]triazolo[1,5-c]pyrimidine hydrochloride (Example 52A), 39.9 mg (0.14 mmol) of 1-{2-amino-6-[(2-aminoethyl)amino]pyridin-3-yl}-2,2,2-trifluoroethanone hydrochloride (Example 13A) and 0.12 ml (0.69 mmol) of N,N-diisopropylethylamine were initially charged in 1 ml of DMSO. The mixture was heated in the microwave at 130° C. for 30 min. This gave, after purification of the crude product by preparative HPLC (Method 11), 58 mg (81% of theory) of the product as a solid.

LCMS (Method 3): $R_t$=1.74 min. (m/z=620 (M+H)$^+$)

$^1$H-NMR (400 MHz, DMSO-d$_6$): δ=8.52 (s, br, 1H), 8.24 (t, 1H), 8.09 (t, 1H), 7.63 (dd, 1H), 7.53 (dd, 2H), 7.44 (dd, 1H), 7.31 (d, 1H), 7.22 (dt, 1H), 7.14 (s, 1H), 5.87 (d, 1H), 3.7-3.78 (m, 2H), 3.62-3.70 (m, 2H), 3.2-3.5 (m, 3H), 2.8-2.9 (m, 3H), 2.66-2.75 (m, 1H), 2.21-2.31 (m, 2H), 0.99 (d, 6H).

Example 16

2-Amino-6-[(2-{[2-(1-cyclopropylpiperidin-4-yl)-7-(2,4-dichlorophenyl)[1,2,4]triazolo[1,5-c]-pyrimidin-5-yl]amino}ethyl)amino]pyridine-3-carbonitrile

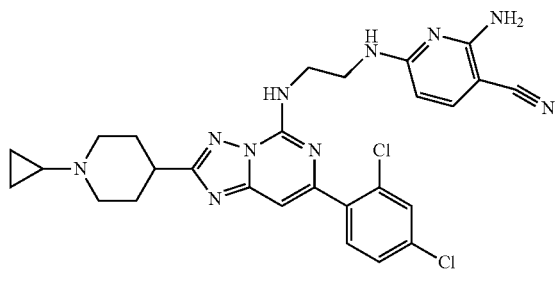 [SMILES: N#Cc1ccc(NCCNc2nc(-c3ccc(Cl)cc3Cl)cc3nc(C4CCN(C5CC5)CC4)nn23)nc1N]

50 mg (0.12 mmol) of 5-chloro-7-(2,4-dichlorophenyl)-2-(1-cyclopropylpiperidin-4-yl)-[1,2,4]-triazolo[1,5-c]pyrimidine hydrochloride (Example 45A), 30 mg (0.14 mmol) of 2-amino-6-[(2-aminoethyl)amino]pyridine-3-carbonitrile dihydrochloride (Example 9A) and 0.125 ml (3.5 mmol) of N,N-diisopropylethylamine were initially charged in 1 ml of DMSO. The mixture was heated in the microwave at 130° C. for 30 min. This gave, after purification of the crude product by preparative HPLC (Method 11), 43 mg (64% of theory) of the product as a solid.

LCMS (Method 8): $R_t$=1.03 min. (m/z=563 (M+H)$^+$)

$^1$H-NMR (400 MHz, DMSO-d$_6$): δ=10.46 (br, 1H), 8.37 (t, 1H), 7.73 (d, 1H), 7.62-7.58 (m, 2H), 7.51 (dd, 1H), 7.36 (m, 1H), 7.20 (s, 1H), 5.83 (br, 1H), 3.72 (m, 4H), 3.61 (m, 2H), 3.45 (m, 1H), 3.39-3.18 (m, 4H), 2.82 (m, 1H), 2.39-2.16 (m, 4H), 1.16 (m, 2H), 0.83 (m, 2H).

Example 17

1-{2-Amino-6-[(2-{[2-(1-cyclopropylpiperidin-4-yl)-7-(2,4-dichlorophenyl)[1,2,4]triazolo[1,5-c]-pyrimidin-5-yl]amino}ethyl)amino]pyridin-3-yl}-2,2,2-trifluoroethanone

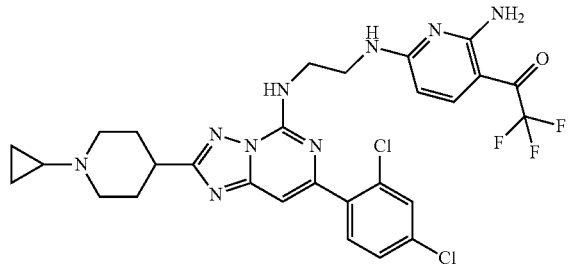 [SMILES: Nc1nc(NCCNc2nc(-c3ccc(Cl)cc3Cl)cc3nc(C4CCN(C5CC5)CC4)nn23)ccc1C(=O)C(F)(F)F]

50 mg (0.12 mmol) of 5-chloro-7-(2,4-dichlorophenyl)-2-(1-cyclopropylpiperidin-4-yl)-[1,2,4]-triazolo[1,5-c]pyrimidine hydrochloride (Example 45A), 92 mg (0.71 mmol) of 1-{2-amino-6-[(2-aminoethyl)amino]pyridin-3-yl}-2,2,2-trifluoroethanone hydrochloride (Example 13A) and 0.125 ml (3.5 mmol) of N,N-diisopropylethylamine were initially charged in 1 ml of DMSO. The mixture was heated in the microwave at 130° C. for 30 min. This gave, after purification of the crude product by preparative HPLC (Method 11), 59 mg (78% of theory) of the product as a solid.

LCMS (Method 8): $R_t$=1.17 min. (m/z=634 (M+H)$^+$)

$^1$H-NMR (400 MHz, DMSO-d$_6$): δ=10.88 (br, 1H), 8.38 (t, 1H), 7.66-7.57 (m, 2H), 7.50 (dd, 1H), 7.40 (dd, 1H), 7.21 (s, 1H), 5.90 (d, 1H), 3.85 (m, 2H), 3.78 (m, 2H), 3.46-3.17 (m, 4H), 2.80 (m, 1H), 2.39 (m, 1H), 2.26 (m, 4H), 1.24 (m, 2H), 0.81 (m, 2H).

Example 18

6-[(2-{[2-(1-Cyclopropylpiperidin-4-yl)-7-(2,4-dichlorophenyl)[1,2,4]triazolo[1,5-c]pyrimidin-5-yl]-amino}ethyl)amino]pyridine-3-carbonitrile

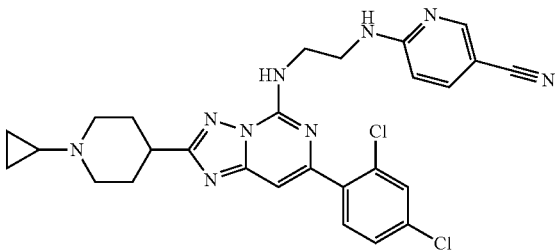 [SMILES: N#Cc1ccc(NCCNc2nc(-c3ccc(Cl)cc3Cl)cc3nc(C4CCN(C5CC5)CC4)nn23)nc1]

21 mg (0.10 mmol) of 5-chloro-7-(2,4-dichlorophenyl)-2-(1-cyclopropylpiperidin-4-yl)[1,2,4]triazolo[1,5-c]pyrimidine hydrochloride (Example 45A), 40 mg (0.10 mmol) of 6-[(2-aminoethyl)-amino]pyridine-3-carbonitrile hydrochloride (Example 2A) and 0.10 ml (0.57 mmol) of N,N-diisopropylethylamine were initially charged in 1 ml of DMSO. The mixture was heated in the microwave at 130° C. for 30 min. This gave, after purification of the crude product by preparative HPLC (Method 11), 32 mg (62% of theory) of the product as a solid.

LCMS (Method 8): $R_t$=1.05 min. (m/z=548 (M+H)$^+$)

$^1$H-NMR (400 MHz, DMSO-d$_6$): δ=10.57 (br, 1H), 8.38 (m, 2H), 7.95 (br, 1H), 7.74 (d, 1H), 7.60-7.49 (m, 3H), 7.17 (s, 1H), 6.51 (br, 1H), 3.74 (m, 2H), 3.62 (m, 4H), 3.44 (m, 1H), 3.31 (m, 2H), 3.22 (m, 1H), 2.82 (m, 1H), 2.35 (m, 1H), 2.24 (m, 4H), 1.18 (m, 2H), 0.84 (m, 2H).

Example 19

1-[2-Amino-6-({1-[2-(1-cyclopropylpiperidin-4-yl)-7-(2,4-dichlorophenyl)[1,2,4]triazolo[1,5-c]-pyrimidin-5-yl]piperidin-3-yl}amino)pyridin-3-yl]propan-1-one

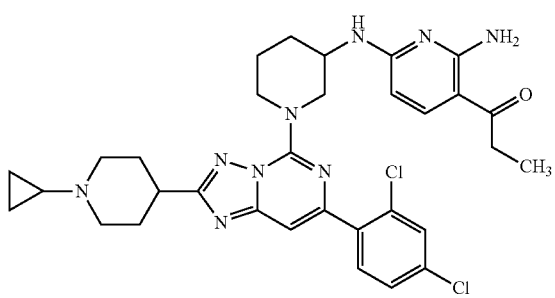 [SMILES: CCC(=O)c1ccc(NC2CCCN(c3nc(-c4ccc(Cl)cc4Cl)cc4nc(C5CCN(C6CC6)CC5)nn34)C2)nc1N]

25 mg (0.06 mmol) of 5-chloro-7-(2,4-dichlorophenyl)-2-(1-cyclopropylpiperidin-4-yl)-[1,2,4]-triazolo[1,5-c]pyrimidine hydrochloride, 20 mg (0.07 mmol) of 1-[2-amino-6-(piperidin-3-ylamino)pyridin-3-yl]propan-1-one hydrochloride (Example 27A) and 65 μl (0.4 mmol) of N,N-diisopropylethylamine were initially charged in 1.25 ml of DMSO. The mixture was heated in the microwave at 120° C. for 30 min. This gave, after purification of the crude product by preparative HPLC (Method 11), 21 mg (56% of theory) of the product as a solid.

LCMS (Method 8): $R_t$=1.12 min. (m/z=634 (M+H)$^+$)

$^1$H-NMR (400 MHz, DMSO-d$_6$): δ=10.07 (br, 1H), 7.88 (br, 1H), 7.74 (br, 1H), 7.69 (d, 1H), 7.54 (br, 1H), 7.37 (s, 1H), 5.94 (br, 1H), 4.42-3.95 (br, 4H), 3.35-3.10 (m, 4H), 2.80 (m, 2H), 2.28-1.95 (m, 6H), 1.74 (m, 2H), 1.08 (m, 5H), 0.81 (m, 2H).

Example 20

2-Amino-6-{[2-({2-[1-(cyclopropylmethyl)piperidin-4-yl]-7-(2,4-dichlorophenyl)[1,2,4]triazolo[1,5-c]pyrimidin-5-yl}amino)ethyl]amino}pyridine-3-carbonitrile

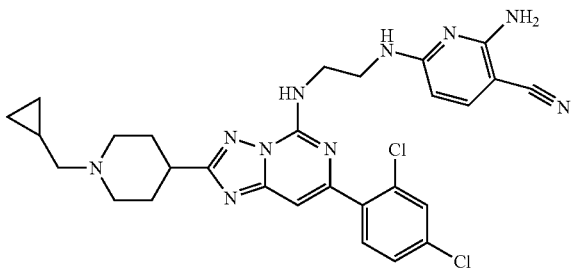 [SMILES: N#Cc1ccc(NCCNc2nc(-c3ccc(Cl)cc3Cl)cc3nc(C4CCN(CC5CC5)CC4)nn23)nc1N]

50 mg (0.10 mmol) of 5-chloro-2-[1-(cyclopropylmethyl)piperidin-4-yl]-7-(2,4-dichlorophenyl)-[1,2,4]triazolo[1,5-c]pyrimidine (Example 47A), 26 mg (0.12 mmol) of 2-amino-6-[(2-aminoethyl)amino]pyridine-3-carbonitrile dihydrochloride (Example 9A) and 0.110 ml (0.6 mmol) of N,N-diisopropylethylamine were initially charged in 1 ml of DMSO. The mixture was heated in the microwave at 130° C. for 30 min. This gave, after purification of the crude product by preparative HPLC (Method 11), 35 mg (59% of theory) of the product as a solid.

LCMS (Method 8): $R_t$=1.06 min. (m/z=577 (M+H)$^+$)

$^1$H-NMR (400 MHz, DMSO-d$_6$): δ=10.18 (br, 1H), 8.36 (t, 1H), 7.74 (d, 1H), 7.61 (d, 1H), 7.52 (d, 1H), 7.34 (m, 1H), 7.20 (s, 1H), 5.82 (br, 1H), 3.49 (m, 1H), 3.15 (m, 3H), 2.98 (m, 2H), 2.36-2.12 (m, 4H), 1.15 (m, 1H), 0.67 (m, 2H), 0.42 (m, 2H). Further H are hidden under the broad signal of water.

Example 21

1-(2-Amino-6-{[2-({2-[1-(cyclopropylmethyl)piperidin-4-yl]-7-(2,4-dichlorophenyl)-[1,2,4]triazolo[1,5-c]pyrimidin-5-yl}amino)ethyl]amino}pyridin-3-yl)-2,2,2-trifluoroethanone

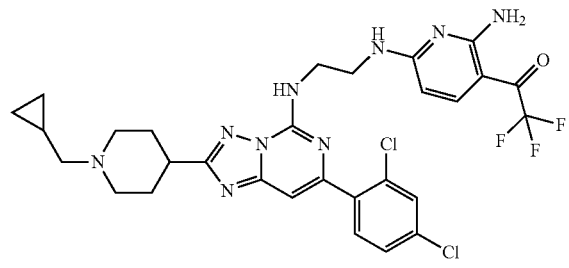 [SMILES: Nc1nc(NCCNc2nc(-c3ccc(Cl)cc3Cl)cc3nc(C4CCN(CC5CC5)CC4)nn23)ccc1C(=O)C(F)(F)F]

50 mg (0.10 mmol) of 5-chloro-2-[1-(cyclopropylmethyl)piperidin-4-yl]-7-(2,4-dichlorophenyl)-[1,2,4]triazolo[1,5-c]pyrimidine (Example 47A), 35 mg (0.12 mmol) of 1-{2-amino-6-[(2-aminoethyl)amino]pyridin-3-yl}-2,2,2-trifluoroethanone hydrochloride (Example 13A) and 0.110 ml (0.6 mmol) of N,N-diisopropylethylamine were initially charged in 1 ml of DMSO. The mixture was heated in the microwave at 130° C. for 30 min. This gave, after purification of the crude product by preparative HPLC (Method 11), 32 mg (48% of theory) of the product as a solid.

LCMS (Method 6): $R_t$=1.52 min. (m/z=648 (M+H)$^1$)

$^1$H-NMR (400 MHz, DMSO-d$_6$): δ=10.43 (br, 1H), 8.67 (br, 1H), 7.68 (d, 1H), 7.61 (d, 1H), 7.47 (d, 1H), 7.43 (dd, 1H), 7.20 (s, 1H), 5.88 (d, 1H), 3.79 (m, 2H), 3.67 (m, 4H), 3.48 (m, 1H), 3.14 (m, 3H), 3.00 (m, 2H), 2.43-2.17 (m, 4H), 1.16 (m, 1H), 0.67 (dd, 2H), 0.43 (dd, 2H).

Example 22

6-{[2-({2-[1-(Cyclopropylmethyl)piperidin-4-yl]-7-(2,4-dichlorophenyl)[1,2,4]triazolo[1,5-c]-pyrimidin-5-yl}amino)ethyl]amino}pyridine-3-carbonitrile

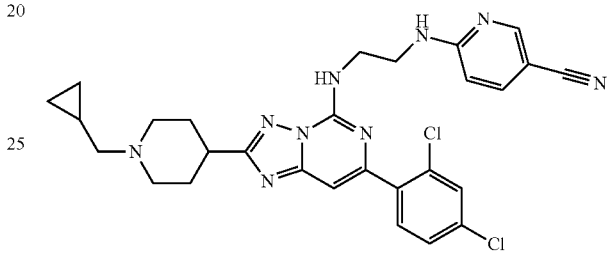

50 mg (0.10 mmol) of 5-chloro-2-[1-(cyclopropylmethyl)piperidin-4-yl]-7-(2,4-dichlorophenyl)-[1,2,4]triazolo[1,5-c]pyrimidine (Example 47A), 25 mg (0.12 mmol) of 6-[(2-aminoethyl)amino]-pyridin-3-carbonitrile hydrochloride (Example 2A) and 0.110 ml (0.6 mmol) of N,N-diisopropylethylamine were initially charged in 1 ml of DMSO. The mixture was heated in the microwave at 130° C. for 30 min. This gave, after purification of the crude product by preparative HPLC (Method 11), 22 mg (38% of theory) of the product as a solid.

LCMS (Method 8): $R_t$=1.11 min. (m/z=562 (M+H)$^+$)

$^1$H-NMR (400 MHz, DMSO-d$_6$): δ=10.22 (br, 1H), 8.35 (m, 2H), 7.84 (br, 1H), 7.74 (d, 1H), 7.55 (m, 3H), 7.17 (s, 1H), 6.50 (br, 1H), 3.74 (m, 2H), 3.65 (m, 4H), 3.48 (m, 1H), 3.15 (m, 3H), 3.01 (m, 2H), 2.44-2.12 (m, 5H), 1.16 (m, 1H), 0.70 (m, 2H), 0.42 (dd, 2H).

Example 23

(4-{5-[(2-{[6-Amino-5-(trifluoroacetyl)pyridin-2-yl]amino}ethyl)amino]-7-(2,4-dichlorophenyl)-[1,2,4]triazolo[1,5-c]pyrimidin-2-yl}piperidin-1-yl)acetic acid

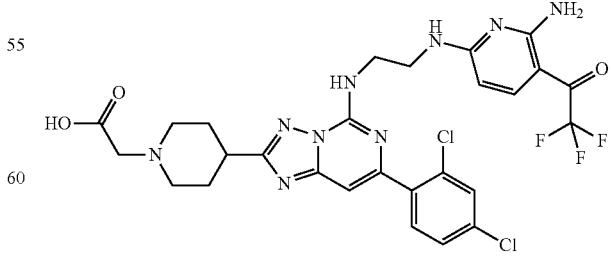

130 mg (0.19 mmol) of ethyl(4-{5-[(2-{[6-amino-5-(trifluoroacetyl)pyridin-2-yl]amino}ethyl)-amino]-7-(2,4-dichlorophenyl)[1,2,4]triazolo[1,5-c]pyrimidin-2- yl}piperidin-1-yl)acetate (Example 56A) were dissolved in 1,2-dimethoxyethane (7.5 ml), water (5 ml) and 31 mg (0.76 mmol) of sodium hydroxide were added and the reaction mixture was stirred at RT for 16 h. The mixture was then concentrated by lyophilization. This gave, after purification of the residue by preparative HPLC (Method 11), 60 mg (48% of theory) of the product as a solid.

LCMS (Method 9): $R_t$=2.13 min. (m/z=652 (M+H)$^+$)

$^1$H-NMR (400 MHz, DMSO-d$_6$): δ=10.32 (br, 1H), 8.71 (br, 1H), 8.35 (br, 1H), 7.69 (s, 1H), 7.62 (d, 1H), 7.49 (d, 1H), 7.43 (d, 1H), 7.21 (s, 1H), 5.90 (d, 1H), 3.80 (m, 2H), 3.69 (m, 4H), 3.47 (m, 1H), 3.33-3.15 (m, 3H), 2.43-2.14 (m, 5H).

Example 24

{4-[5-({2-[(5-Cyanopyridin-2-yl)amino]ethyl}amino)-7-(2,4-dichlorophenyl)[1,2,4]triazolo[1,5-c]pyrimidin-2-yl]piperidin-1-yl}acetic acid

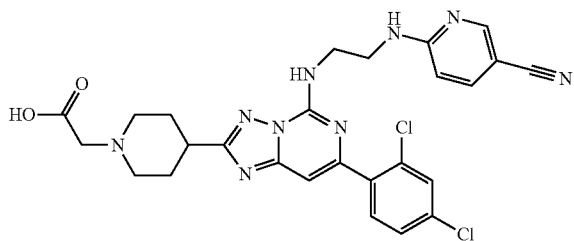 [SMILES: N#Cc1ccc(NCCNc2nc(-c3ccc(Cl)cc3Cl)cc3nc(C4CCN(CC(=O)O)CC4)nn23)nc1]

105 mg (0.18 mmol) of ethyl-{4-[5-({2-[(5-cyanopyridin-2-yl)amino]ethyl}amino)-7-(2,4-dichlorophenyl)[1,2,4]triazolo[1,5-c]pyrimidin-2-yl]piperidin-1-yl}acetate (Example 57A) were dissolved in 1,2-dimethoxyethane (7.5 ml), water (5 ml) and 31 mg (0.76 mmol) of sodium hydroxide were added and the reaction mixture was stirred at RT for 16 h. The mixture was then concentrated by lyophilization. This gave, after purification of the residue by preparative HPLC (Method 11), 65 mg (65% of theory) of the product as a solid.

LCMS (Method 9): $R_t$=1.93 min. (m/z=566 (M+H)$^+$)

$^1$H-NMR (400 MHz, DMSO-d$_6$): δ=10.11 (br, 1H), 8.36 (m, 2H), 7.79 (br, 1H), 7.75s, 1H), 7.60-7.50 (m, 3H), 7.18 (s, 1H), 6.49 (br, 1H), 4.17 (br, 2H), 3.85 (m, 4H), 3.71 (m, 2H), 3.64 (m, 2H), 3.27 (m, 3H), 2.31 (m, 3H), 2.16 (m, 2H).

Example 25

2-Amino-6-[(2-{[7-(2,4-dichlorophenyl)-2-(1-methylpiperidin-4-yl)[1,2,4]triazolo[1,5-c]pyrimidin-5-yl]amino}ethyl)amino]pyridine-3-carbonitrile

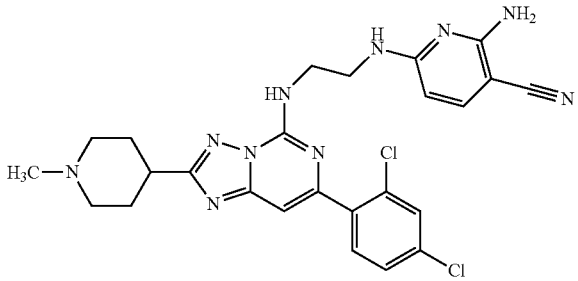 [SMILES: CN1CCC(c2nc3cc(-c4ccc(Cl)cc4Cl)nc(NCCNc4ccc(C#N)c(N)n4)n3n2)CC1]

50 mg (0.12 mmol) of 5-chloro-7-(2,4-dichlorophenyl)-2-(1-methylpiperidin-4-yl)[1,2,4]triazolo-[1,5-c]-pyrimidine hydrochloride (Example 49A), 32 mg (0.15 mmol) of 2-amino-6-[(2-aminoethyl)-amino]pyridine-3-carbonitrile dihydrochloride (Example 9A) and 0.13 ml (0.75 mmol) of N,N-diisopropylethylamine were initially charged in 1.5 ml of DMSO. The mixture was heated in the microwave at 130° C. for 30 min. This gave, after purification of the crude product by preparative HPLC (Method 11), 43 mg (64% of theory) of the product as a solid.

LCMS (Method 8): $R_t$=0.99 min. (m/z=537 (M+H)$^+$)

$^1$H-NMR (400 MHz, DMSO-d$_6$): δ=10.80 (br, 1H), 8.38 (t, 1H), 7.75 (d, 1H), 7.60 (d, 1H), 7.53 (m, 1H), 7.30 (m, 1H), 7.19 (s, 1H), 5.81 (br, 1H), 3.70 (m, 2H), 3.60 (m, 2H), 3.51 (m, 2H), 3.35 (m, 1H), 3.14 (m, 4H), 2.75 (d, 3H), 2.70 (m, 1H), 2.35-2.12 (m, 4H).

Example 26

6-[(2-{[7-(2,4-Dichlorophenyl)-2-(1-methylpiperidin-4-yl)[1,2,4]triazolo[1,5-c]pyrimidin-5-yl]amino}ethyl)amino]pyridine-3-carbonitrile

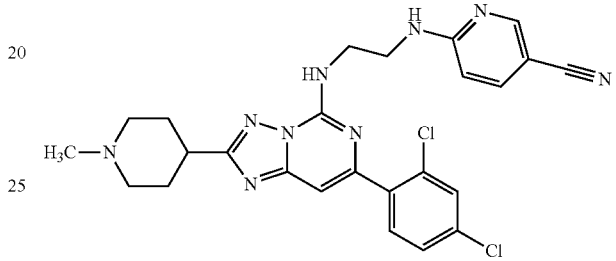

50 mg (0.13 mmol) of 5-chloro-7-(2,4-dichlorophenyl)-2-(1-methylpiperidin-4-yl)[1,2,4]triazolo-[1,5-c]pyrimidine hydrochloride (Example 49A), 30 mg (0.15 mmol) of 6-[(2-aminoethyl)amino]pyridin-3-carbonitrile hydrochloride (Example 2A) and 0.13 ml (0.76 mmol) of N,N-diisopropylethylamine were initially charged in 1.5 ml of DMSO. The mixture was heated in the microwave at 130° C. for 30 min. This gave, after purification of the crude product by preparative HPLC (Method 11), 25 mg (37% of theory) of the product as a solid.

LCMS (Method 3): $R_t$=1.57 min. (m/z=522 (M+H)$^+$)

$^1$H-NMR (400 MHz, DMSO-d$_6$): δ=10.40 (br, 1H), 8.36 (m, 2H), 7.87 (br, 1H), 7.74 (d, 1H), 7.63-7.49 (m, 3H), 7.18 (s, 1H), 6.50 (br, 1H), 3.72 (m, 2H), 3.62 (m, 2H), 3.54 (m, 2H), 3.39 (m, 1H), 3.15 (m, 4H), 2.2.78 (d, 3H), 2.72 (m, 1H), 2.35-2.05 (m, 4H).

Example 27

1-{2-Amino-6-[(2-{[7-(2,4-dichlorophenyl)-2-(1-methylpiperidin-4-yl)[1,2,4]triazolo[1,5-c]-pyrimidin-5-yl]amino}ethyl)amino]pyridin-3-yl}-2,2,2-trifluoroethanone

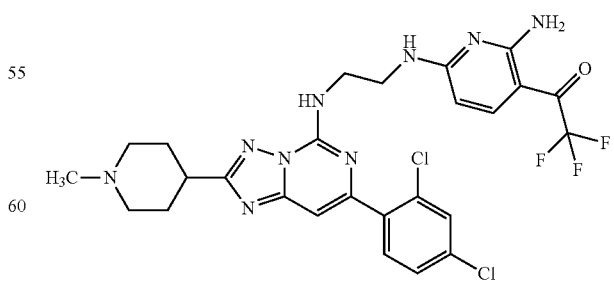

50 mg (0.13 mmol) of 5-chloro-7-(2,4-dichlorophenyl)-2-(1-methylpiperidin-4-yl)[1,2,4]-triazolo[1,5-c]pyrimidine hydrochloride (Example 49A), 43 mg (0.15 mmol) of 1-{2- amino-6-[(2-aminoethyl)-amino]pyridin-3-yl}-2,2,2-trifluoroethanone hydrochloride (Example 13A) and 0.130 ml (0.76 mmol) of N,N-diisopropylethylamine were initially charged in 1.5 ml of DMSO. The mixture was heated in the microwave at 130° C. for 30 min. This gave, after purification of the crude product by preparative HPLC (Method 11), 52 mg (67% of theory) of the product as a solid.

LCMS (Method 8): $R_t$=1.13 min. (m/z=608 (M+H)$^+$)

$^1$H-NMR (400 MHz, DMSO-d$_6$): δ=10.86 (br, 1H), 8.65 (br, 1H), 8.38 (m, 1H), 7.70 (d, 1H), 7.59 (d, 1H), 7.47 (d, 1H), 7.42 (dd, 1H), 7.20 (s, 1H), 5.89 (d, 1H), 3.78 (m, 2H), 3.69 (m, 2H), 3.52 (m, 4H), 3.13 (m, 2H), 2.76 (d, 3H), 2.40 (m, 1H), 2.22 (m, 4H).

B) ASSESSMENT OF THE PHYSIOLOGICAL ACTIVITY

The suitability of the compounds according to the invention for treating hematological disorders can be shown in the following assay systems:

In Vitro Assay

The inhibitory activity of active substances is determined in a biochemical assay. The ingredients required for this purpose are mixed in a black 384-well microtitre plate with transparent base (from Greiner, catalogue number 781092). The requirements in this connection for each well of the 384-well microtitre plate are 5 nM GSK3β (from Upstate, catalogue number 14-306), 40 μM GSK3β substrate GSM (sequence H-RRRPASVPPSPSLSRHS-(pS)-HQRR, from Upstate, catalogue number 2-533), 30 μM nicotinamide adenine dinucleotide NADH (Roche Diagnostics, catalogue number 10107735), 50 μM adenosine triphosphate ATP (from Sigma, catalogue number A7966), 2 mM phosphoenolpyruvate (from Roche, catalogue number 128112), and also about 1 U/ml of pyruvate kinase and about 1 U/ml of lactate dehydrogenase, which are present together in a stock formulation (from Roche, catalogue number 10737291001, suspension with about 450 U/ml of pyruvate kinase activity, about 450 U/ml of lactate dehydrogenase activity in 3.2 mM ammonium sulphate solution pH 6), where 1 unit pyruvate kinase converts, at pH 7.6 and 37° C., 1 μmol of phosphoenolpyruvate into pyruvate per minute, and where 1 unit of lactate dehydrogenase reduces, at pH 7.5 and 37° C., 1 μmol of pyruvate to lactate per minute. The required reaction buffer in which the biochemical reaction takes place consists of 50 mM Trizma hydrochloride Tris-HCl pH: 7.5 (from Sigma, catalogue number T3253), 5 mM magnesium chloride MgCl$_2$ (from Sigma, catalogue number M8266), 0.2 mM DL-dithiothreitol DTT (from Sigma, catalogue number D9779), 2 mM ethylenediaminetetraacetic acid EDTA (from Sigma, catalogue number E6758), 0.01% Triton X-100 (from Sigma, catalogue number T8787) and 0.05% bovine serum albumin BSA (from Sigma, catalogue number B4287).

Active substances are dissolved in dimethyl sulfoxide DMSO (from Sigma, catalog number D8418) in a concentration of 10 mM. Active substances are added in serial concentrations of 10 μM, 1 μM, 0.1 μM, 0.01 μM, 0.001 μM, 0.0001 μM, 0.00001 μM, 0.000001 μM to the mixtures of the biochemical reaction. As control, dimethyl sulfoxide is added instead of substance in a final concentration of 0.1%.

The reaction is incubated at 30° C. for 2 hours and then the resulting fluorescence is measured in a Tecan Safire-XFLUOR4 instrument, version V4.50 (serial number 12901300283) with the specifications: measurement mode—fluorescence measured from below, extinction wavelength 340 nm, emission wavelength 465 nm, slit width extinction 5 nm, slit width emission 5 nm, gain mode 120, delay 0 μs, number of light flashes per measurement 3, and an integration time of 40 μs.

The GSK3β activity is measured in fluorescence units, with the values of uninhibited kinase being set equal to 100% and those of completely inhibited kinase being set equal to 0%. The activity of the active substances is calculated in relation to these 0% and 100%.

Table A shows IC$_{50}$ values which were determined using the assay described above.

TABLE A

| Example No. | IC$_{50}$ [nM] |
|---|---|
| 1 | 15 |
| 5 | 10 |
| 13 | 4 |
| 21 | 20 |
| 23 | 9 |
| Ent-A-13 | 2 |

CD34+ Proliferation Assays for Testing GSK3β Inhibitors

Adult hematopoietic stem cells are characterized by the specific expression of membrane-associated proteins. These surface markers are provided with an appropriate number appropriate for their molecular weight. This class also includes the molecule which is referred to as CD34 and which serves for the identification, characterization and isolation of adult hematopoietic stem cells. These stem cells can moreover be isolated from bone marrow, peripheral blood or umbilical cord blood. These cells have limited viability in in vitro cultures but can be stimulated to proliferation and differentiation by various additions to the culture medium. CD34-positive cells are used here in order to test the influence of substances on the activity of glycogen synthase kinase 3. For this purpose, in a first step, mononuclear cells are isolated from umbilical cord blood by differential centrifugation steps.

For this purpose, umbilical cord blood is diluted 1:4 with phosphate-buffered saline solution. 50 milliliter centrifugation vessels are charged with 17 milliliters of Ficoll (density 1.077, Ficoll Paque Plus; Pharmacia, catalog number 17-1440-02). 30 milliliters of the 1:4 diluted umbilical cord blood are layered thereon and then centrifuged at 400×g at room temperature for 30 minutes. The brakes of the centrifuge are disengaged during this. Owing to the centrifugation, the mononuclear cells collect in the interphase. This is removed with the aid of a 30 milliliter pipette and transferred into a new 50 milliliter centrifugation vessel, and the volume is then made up to 30 ml with phosphate-buffered saline solution. These cells are centrifuged at 300×g with the brake engaged at room temperature for 10 minutes. The supernatant is discarded and the resulting cell pellet is resuspended in 30 milliliters of phosphate-buffered saline solution. These cells are again centrifuged at 200×g with brake engaged at 20° C. for 15 minutes.

To isolate the CD34-positive cells, the enriched mononuclear cells are resuspended in a concentration of 1×10$^8$ cells per 300 microliters of MACS buffer (0.5% endotoxin-free bovine serum albumin in phosphate-buffered saline solution). 100 microliters of FCR blocking reagent (Miltenyi Biotec, catalog number 130-046-702) and 100 microliters of CD34 microbeads (Miltenyi Biotec, catalog number 130-046-702) are added. This suspension is incubated at 4° C. for 30 minutes. The cells are then diluted with 20 times the volume of MACS buffer and centrifuged at 300×g for 10 minutes. The supernatant is discarded and the cells are resuspended in 500 microliters of MACS buffer. The cells treated in this way are loaded onto an LS column (Miltenyi Biotec, catalog number 130-042-401) and purified using a Midi MACS magnet (Miltenyi Biotec, catalog number 130-042-303).

The number of CD34-positive cells is determined by counting the cells using a Neubauer chamber. The purity of the cells is determined by standard protocols using the fluorescent activated cell sorting method (Becton Dickinson, BD FACS™ Sample Prep Assistant SPAII Upgrade Kit, catalog number 337642).

To determine the influence of modulating the GSK3 activity, CD34-positive cells are incubated in a 96-well microtiter plate at 37° C. and 5% carbon dioxide for 7 days and then the proliferation rates are determined on the basis of the cell counts.

For this purpose, 5000 CD34-positive cells are taken up in 100 microliters of IMDM medium (Life Technology, catalog number 12440-046), 10% fetal calf serum (Life Technology, catalog number 10082-139) and 20 nanograms per milliliter of stem cell factor (R&D, catalog number 255-SC-010) in each well of a 96 U-bottom well microtiter plate (Greiner Bio-One, catalog number 650 180). In addition, the cells are also mixed with various concentrations of substances dissolved in dimethyl sulfoxide (Sigma Aldrich, catalog number D5879-1L). This entails 4 wells in each case with the stated cell count of 5000 CD34-positive cells per well being provided with 10 micromol, 4 wells with 5 micromol, 4 wells with 2.5 micromol, 4 wells with 1.25 micromol, 4 wells with 0.625 micromol, 4 wells with 0.3125 micromol, 4 wells with 0.156 micromol, 4 wells with 0.078 micromol and as control 4 wells with 0.1% dimethyl sulfoxide as final concentration.

These cells treated in this way are incubated in a cell culture incubator at 37° C. and 5% carbon dioxide for 7 days. The proliferation rate is determined by renewed counting of the cells using a Neubauer counting chamber, with the cells provided only with the stem cell factor being set as 100% value, and all other values being related to this value.

In Vivo Assay

The investigations of the in vivo effect of the compounds according to the invention take place using 6-week old male C57BL/6 mice (Charles River, Sulzfeld, Germany) weighing 18-22 g. These animals are kept appropriate for the species with 12-hour light and dark cycles under constant climatic conditions and with water and mouse feed ad libitum. The concentrations of chemotherapeutics used are administered to the animals in accordance with the manufacturer's statements by intraperitoneal (i.p.) injections in the caudal third of the abdomen. The same procedure is applied to the substances relevant to the invention. Blood samples are taken from the retrobulbar venous plexus using Pasteur pipettes. The number of neutrophilic granulocytes is determined completely automatically using flow cytometry systems.

CYP Inhibition Test

The ability of substances to inhibit CYP1A2, CYP2C8, CYP2C9, CYP2D6 and CYP3A4 in humans is examined using pooled human liver microsomes as enzyme source in the presence of standard substrates (see below) which form CYP isoform-specific metabolites. The inhibitory effects are studied at six different concentrations of the test compounds (1.5, 3.1, 6.3, 12.5, 25 and 50 µM) and compared to the extent of the CYP isoform-specific metabolite formation of the standard substrates in the absence of test compounds, and the corresponding $IC_{50}$ values are calculated. A standard inhibitor which specifically inhibits a single CYP isoform serves as control of the results obtained.

Procedure:

The incubation of phenacetin, amodiaquine, diclofenac, dextromethorphan or midazolam with human liver microsomes in the presence of in each case six different concentrations of a test compound (as potential inhibitor) is carried out on a workstation (Tecan, Genesis, Crailsheim, Germany). Standard incubation mixtures comprise 1.3 mM NADP, 3.3 mM $MgCl_2 \times 6\,H_2O$, 3.3 mM glucose 6-phosphate, glucose 6-phosphate dehydrogenase (0.4 U/ml) and 100 mM phosphate buffer (pH 7.4) in a total volume of 200 µl. Test compounds are preferably dissolved in acetonitrile. 96-Well plates are incubated for a defined period of time at 37° C. with pooled human liver microsomes. The reactions are stopped by addition of 100 µl of acetonitrile comprising a suitable internal standard. Precipitated proteins are removed by centrifugation, and the supernatants are combined and analysed by LC-MS/MS.

Determination of the Solubility

Reagents Required:

PBS buffer pH 6.5: 61.86 g of sodium chloride p.a. (for example from Merck, Art. No. 1.06404.1000), 39.54 g of sodium dihydrogen phosphate p.a. (for example from Merck, Art. No. 1.06346.1000) and 83.35 g of 1 N sodium hydroxide solution (for example from Bernd Kraft GmbH, Art. No. 01030.4000) are weighed out into a 1 liter measuring flask and made up with water, and the mixture is stirred for about 1 hour. 500 ml of this solution are transferred into a 5 liter measuring flask and made up with water. The pH is adjusted to 6.5 using 1 N sodium hydroxide solution.

Dimethyl sulfoxide (for example from Baker, Art. No. 7157.2500)

Distilled water

Acetonitrile Chromasolv (for example Riedel-de Haen Art. No. 34851)

50% strength formic acid p.a. (for example Fluka Art. No. 09676)

Preparation of the Starting Solution:

At least 1.5 mg of the test substance are weighed out accurately into a Wide Mouth 10 mm Screw V-Vial (from Glastechnik Gräfenroda GmbH, Art. No. 8004-WM-H/V 15µ) with fitting screw cap and septum, dimethyl sulfoxide is added to give a concentration of 50 mg/ml and the mixture is vortexed for 30 minutes.

Preparation of the Calibration Solutions:

The required pipetting steps are carried out in a 1.2 ml Deep Well Plate (DWP) with 96 wells (e.g. HJ-Bioanalytik GmbH Art. No. 850289) using a liquid handling robot. The solvent used is a mixture of acetonitrile Chromasolv/distilled water 8:2.

Preparation of the starting solution for calibration solutions (stock solution): 833 µl of the solvent mixture are added to 10 µl of the initial solution (concentration=600 µg/ml), and the mixture is homogenized. For each test substance, 1:100 dilutions are prepared in separate DWPs, and the dilutions for their part are homogenized. One of the 1:100 dilutions is used for preparing the calibration solutions, the second dilution is used for optimizing the MS/MS parameter.

Calibration solution 5 (600 ng/ml): 270 µl of solvent mixture are added to 30 µl of the stock solution, and the mixture is homogenized.

Calibration solution 4 (60 ng/ml): 270 µl of solvent mixture are added to 30 µl of calibration solution 5, and the mixture is homogenized.

Calibration solution 3 (12 ng/ml): 400 µl of solvent mixture are added to 100 µl of calibration solution 4, and the mixture is homogenized.

Calibration solution 2 (1.2 ng/ml): 270 µl of solvent mixture are added to 30 µl of calibration solution 3, and the mixture is homogenized.

Calibration solution 1 (0.6 ng/ml): 150 µl of solvent mixture are added to 150 µl of calibration solution 2, and the mixture is homogenized.

Preparation of the Sample Solutions:

The required pipetting steps are carried out in a 1.2 ml DWP with 96 wells (e.g. HJ-Bioanalytik GmbH Art. No. 850289) using a liquid handling robot.

1000 µl of PBS buffer pH 6.5 are added to 10.1 µl of the stock solution.

Procedure:

The required pipetting steps are carried out in a 1.2 ml DWP with 96 wells (e.g. HJ-Bioanalytik GmbH Art. No. 850289) using a liquid handling robot.

Using a temperature-adjustable shaker (e.g. from Eppendorf Thermomixer comfort Art. No. 5355 000.011), the sample solutions prepared in this manner are shaken at 20° C. and 1400 rpm for 24 hours. From these solutions, in each case 180 µl are removed and transferred into Beckman polyallomer centrifuge tubes (Art. No. 343621). These solutions are centrifuged at about 223 000×g for 1 hour (e.g. from Beckman Optima L-90K Ultracentrifuge with type 42.2 Ti rotor at 42 000 rpm). From each sample solution, 100 µl of the supernatant are removed and diluted 1:10 and 1:1000 with PBS buffer 6.5.

Analysis:

The samples are analysed by HPLC/MS-MS. Quantification is carried out using a five point calibration curve of the test compound. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 7) sample solution 1:10.

HPLC/MS-MS Method

HPLC: Agilent 1100, quat. pump (G1311A), autosampler CTC HTS PAL, degasser (G1322A) and column thermostat (G1316A); column: Oasis HLB 20 mm×2.1 mm, 25µ; temperature: 40° C.; mobile phase A: water+0.5 ml of formic acid/l; mobile phase B: acetonitrile+0.5 ml of formic acid/l; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS initial splitter 1:20; measurement in the ESI mode.

For each test substance, the instrument parameters are automatically optimized by injection of the stock solution described further above (second 1:100 dilution) using the MassLynx/QuanOptimize software.

C) EXEMPLARY EMBODIMENTS OF PHARMACEUTICAL COMPOSITIONS

The substances according to the invention can be converted into pharmaceutical preparations in the following ways:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. The granules are dried and then mixed with magnesium stearate for 5 min. This mixture is compressed with a conventional tablet press (see above for format of the tablet).

Oral Suspension:

Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound according to the invention.

Production:

The Rhodigel is suspended in ethanol, and the compound of Example 1 is added to the suspension. The water is added while stirring. The mixture is stirred for about 6 h until the swelling of the Rhodigel is complete.

Solution which can be Administered Intravenously:

Composition:

1 mg of the compound of Example 1, 15 g of polyethylene glycol 400 and 250 g of water for injections.

Production:

The compound of Example 1 is dissolved together with polyethylene glycol 400 in the water by stirring. This solution is sterilized by filtration (pore diameter 0.22 µm) and dispensed under aseptic conditions into heat-sterilized infusion bottles. These are closed with infusion stoppers and crimped caps.

The invention claimed is:

1. A compound of the formula $$(I)$$

[Structure with $R^{13}$, $R^1$, N, A, $R^2$, $R^4$, m]

in which

A represents a group of the formula

[Structure with $\#_1$, N, N, N, $\#_2$, $\#_3$]

where $\#_1$ represents the point of attachment to the heterocycle substituted by $R^1$,

2 represents the point of attachment to the carbon atom to which $R^{13}$ is attached,

3 represents the point of attachment to the carbon atom to which $R^4$ is attached, m represents the number 1, 2, 3 or 4, $R^1$ represents hydrogen, $C_1$-$C_6$-alkyl, $C_3$-$C_6$-cycloalkyl, $C_3$-$C_6$-cycloalkylmethyl or hydroxycarbonylmethyl, $R^2$ represents phenyl, where phenyl may be substituted by 1 to 3 substituents, where the substituents are independently of one another selected from the group consisting of hydroxyl, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulfonyl, $C_1$-$C_4$-alkylsulfonylamino, $C_1$-$C_4$-alkylamino sulfonyl, phenyl, pyrrolidinyl, piperidinyl, morpholinyl, piperazinyl, pyrrolidinylmethyl, piperidinylmethyl, morpholinylmethyl and piperazinylmethyl, where phenyl, pyrrolidinyl, piperidinyl, morpholinyl, piperazinyl, pyrrolidinylmethyl, piperidinylmethyl, morpholinylmethyl and piperazinylmethyl may be substituted by 1 to 3 substituents, where the substituents are independently of one another selected from the group consisting of halogen, cyano, trifluoromethyl, trifluoromethoxy and $C_1$-$C_4$-alkyl, $R^4$ represents hydrogen, chlorine or fluorine,
$R^{13}$ represents a group of the formula

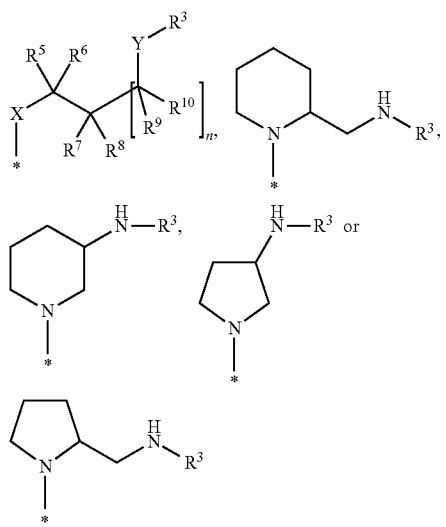

where
* represents the point of attachment to the heterocycle,
n represents the number 0 or 1,
X represents $NR^{11}$, S or O,
  where
    $R^{11}$ represents hydrogen, $C_1$-$C_3$-alkyl or cyclopropyl,
Y represents $NR^{12}$, S or O,
  where
    $R^{12}$ represents hydrogen, $C_1$-$C_3$-alkyl or cyclopropyl,
$R^3$ represents 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl,
  where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are independently of one another selected from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, where alkyl, alkoxy, alkylamino, alkylcarbonyl, alkoxycarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl, $R^5$ represents hydrogen, $C_1$-$C_3$-alkyl or cyclopropyl,
$R^6$ represents hydrogen or $C_1$-$C_3$-alkyl,
$R^7$ represents hydrogen, $C_1$-$C_3$-alkyl or cyclopropyl,
$R^8$ represents hydrogen or $C_1$-$C_3$-alkyl,
$R^9$ represents hydrogen, $C_1$-$C_3$-alkyl or cyclopropyl,
$R^{10}$ represents hydrogen or $C_1$-$C_3$-alkyl,
or one of its salts.

2. The compound as claimed in claim 1, wherein
$R^4$ represents hydrogen or chlorine,
$R^{13}$ represents a group of the formula

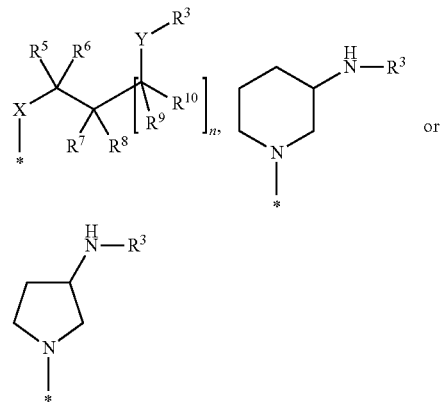

where
* represents the point of attachment to the heterocycle,
n represents the number 0,
X represents $NR^{11}$,
  where
    $R^{11}$ represents hydrogen or methyl,
Y represents $NR^{12}$,
  where
    $R^{12}$ represents hydrogen or methyl,
$R^3$ represents 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl,
  where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are independently of one another selected from the group consisting of halogen, cyano, nitro, amino, trifluoromethyl, trifluoromethoxy, aminocarbonyl, trifluoromethylcarbonyl, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, where alkylamino, alkylcarbonyl, alkoxycarbonyl, alkylaminocarbonyl and cycloalkylcarbonyl may be substituted by one substituent, where the substituent is selected from the group consisting of halogen, cyano, hydroxyl, amino, trifluoromethyl and $C_3$-$C_6$-cycloalkyl, $R^5$ represents hydrogen or methyl,
$R^6$ represents hydrogen,
$R^7$ represents hydrogen or methyl,
$R^8$ represents hydrogen,
$R^9$ represents hydrogen,
$R^{10}$ represents hydrogen,
or one of its salts.

3. The compound as claimed in claim 1, wherein
m represents the number 1, 2 or 3,
$R^1$ represents $C_1$-$C_4$-alkyl, cyclopropyl, cyclopropylmethyl or hydroxycarbonylmethyl,
$R^2$ represents phenyl,
  where phenyl may be substituted by 1 to 3 substituents, where the substituents are independently of one another selected from the group consisting of chlorine, fluorine, trifluoromethyl and methyl,
$R^4$ represents hydrogen,
$R^{13}$ represents a group of the formula

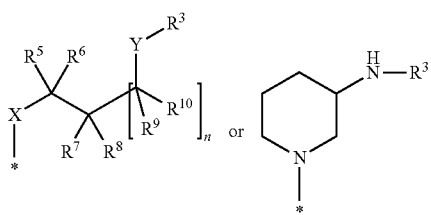

where
* represents the point of attachment to the heterocycle,
n represents the number 0,
X represents $NR^{11}$,
  where
    $R^{11}$ represents hydrogen,
Y represents $NR^{12}$,
  where
    $R^{12}$ represents hydrogen,
$R^3$ represents 2-pyridyl,
  where 2-pyridyl is substituted by 1 or 2 substituents, where the substituents are independently of one another selected from the group consisting of cyano, nitro, amino, trifluoromethylcarbonyl, ethylcarbonyl and methylcarbonyl,
$R^5$ represents hydrogen,
$R^6$ represents hydrogen,
$R^7$ represents hydrogen,
$R^8$ represents hydrogen,
$R^9$ represents hydrogen,
$R^{10}$ represents hydrogen,
or one of its salts.

4. A pharmaceutical composition comprising a compound as claimed in claim 1 and an inert non-toxic pharmaceutically acceptable auxiliary.

5. A pharmaceutical composition comprising a compound as claimed in claim 2 and an inert non-toxic pharmaceutically acceptable auxiliary.

6. A pharmaceutical composition comprising a compound as claimed in claim 3 and an inert non-toxic pharmaceutically acceptable auxiliary.

7. A process for preparing a compound of the formula (I), or one of its salts, as claimed in claim 1, wherein

[A] a compound of the formula

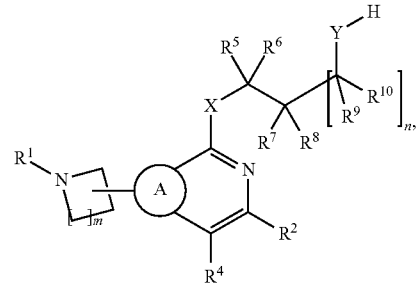

(II)

in which
A, m, X, Y, $R^1$, $R^2$, $R^4$, $R^5$, $R^6$, $R^7$, $R^8$, $R^9$ and $R^{10}$ have the meaning given in claim 1,
is reacted with a compound of the formula $R^3$—$X^1$ (III), in which
$R^3$ has the meaning given in claim 1, and
$X^1$ represents halogen,
or
[B] a compound of the formula

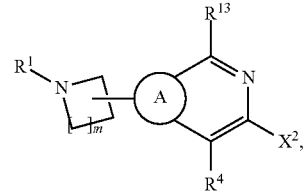

(IV)

in which
A, m, $R^1$, $R^4$ and $R^{13}$ have the meaning given in claim 1, and
$X^2$ represents iodine, bromine, chlorine or trifluoromethanesulfonyl,
is reacted with a compound of the formula

Q-$R^2$ (V), in which
$R^2$ has the meaning given in claim 1, and
Q represents —$B(OH)_2$, a boronic acid ester, or —$BF_3^-K^+$, under Suzuki coupling conditions,
or
[C] a compound of the formula

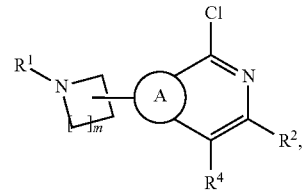

(VI)

in which
A, m, $R^1$, $R^2$ and $R^4$ have the meaning given in claim 1,
is reacted with a compound of the formula

H—$R^{13}$ (IX), in which
$R^{13}$ has the meaning given in claim 1.

* * * * *